United States Patent
Leys et al.

(10) Patent No.: US 9,157,099 B2
(45) Date of Patent: Oct. 13, 2015

(54) METHODS FOR PREPARING A HYDROCARBON

(71) Applicant: SHELL OIL COMPANY, Houston, TX (US)

(72) Inventors: David Leys, Manchester (GB); Karl Alex Peter Payne, Manchester (GB); Nigel Shaun Scrutton, Manchester (GB); David Alexander Parker, Chester (GB); Andrew James Murphy, Chester (GB)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/915,059

(22) Filed: Jun. 11, 2013

(65) Prior Publication Data

US 2013/0330795 A1  Dec. 12, 2013

(30) Foreign Application Priority Data

Jun. 11, 2012  (EP) .................................... 12171463

(51) Int. Cl.
| | | |
|---|---|---|
| *C12P 5/02* | (2006.01) | |
| *C12P 5/00* | (2006.01) | |
| *C12N 9/88* | (2006.01) | |
| *C10L 1/04* | (2006.01) | |
| *C10G 45/58* | (2006.01) | |
| *C10L 1/02* | (2006.01) | |
| *C10G 3/00* | (2006.01) | |

(52) U.S. Cl.
CPC . *C12P 5/026* (2013.01); *C10G 3/42* (2013.01); *C10G 3/50* (2013.01); *C10G 45/58* (2013.01); *C10L 1/02* (2013.01); *C10L 1/04* (2013.01); *C12N 9/88* (2013.01); *C12P 5/005* (2013.01); *C12Y 401/01* (2013.01)

(58) Field of Classification Search
None
See application file for complete search history.

(56) References Cited

U.S. PATENT DOCUMENTS

2011/0165644 A1  7/2011  Marliere

FOREIGN PATENT DOCUMENTS

| EP | 0857789 | 8/1998 |
|---|---|---|
| GB | 2433260 | 6/2007 |

OTHER PUBLICATIONS

GenBank XP664768.1 < http://www.ncbi.nlm.nih.gov/protein/XP_664768.1 > Retrieved Jul. 2014.*
GenBacnk GAA19696.1 < http://www.ncbi.nlm.nih.gov/protein/GAA19696.1 > Retrieved Jul. 2014.*
GenBank YP_002413752.1 < http://www.ncbi.nlm.nih.gov/protein/YP_002413752.1 > Retrieved Jul. 2014.*
GenBank ABI94381.1 < http://www.ncbi.nlm.nih.gov/protein/ABI94381.1 > Retrieved Jul. 2014.*
Stratford et al.; "Decarboxylation of Sorbic Acid by Spoilage Yeasts is Associated with the PAD1 Gene"; Applied and environmental Microbiology; vol. 73, No. 20; pp. 6534-6542; Oct. 2007.
Needleman et al.; A General Method Applicable to the Search for Similarities in the Amino Acid Sequence of Two Proteins'; J. Mol. Biol.; vol. 48; pp. 443-453; 1970.
McKenna et al.; Styrene biosynthesis from glucose by engineered *E. coli*'; Metab. Eng.' vol. 13(5); pp. 544-end of article; Sep. 2011.
Mukai, N, et al.; PAD1 and FDC1 are essential for the decarboxylation of phenylacrylic acids in *Saccharomyces cerevisiae*; Journal of Bioscience and Bioengineering; vol. 109, No. 6; pp. 564-569; 2010.
"Enzyme Nomenclauture"; Nomenclature Committee of the International Union of Biochemistry and Molecular Biology; Including Supplements 6-17; 1992.
Plumridge, Andrew; The decarboxylation of the weak-acid preservative, sorbic acid, is encloded by linked genes in *Aspergillus* spp.; Fungal Genetics and Biology; vol. 47; pp. 683-692; 2010.
Li, Wenli, et al.; "Characterization of the Tautomycetin Biosynthetic Gene Cluster from *Streptomyces* griseochromogenes Provides New Insight into Dialkylamaleic Biosynthesis"; J. Nat. Prod., vol. 72; pp. 450-459; 2009.
European Search Report for European Application 12171463.8 dated Jan. 17, 2013.
Van Der Klis, F., et al., "Oxidative Decarboxylation of Unsaturated Fatty Acids", European Journal of Lipid Science & Technology, vol. 113, No. 5, pp. 562-571, May 5, 2011.
Pel, Herman J. et al."SubName: Full=Putative Uncharacterized Protein AnO3g06590, Ebi Accession No. UNIPROT: A2QHE5 & Genome Sequencing and Analysis of the Versatile Cell Factory *Aspergillus niger* CBS 513:88", Nature Biotechnology, vol. 25, No. 2, pp. 221-231, Feb. 2007.
International Search Report dated Nov. 5, 2013, Application No. PCT/E02013/062038 filed Jun. 11, 2013.

* cited by examiner

*Primary Examiner* — Suzanne M Noakes

(57) ABSTRACT

Method for preparing a mono-unsaturated alkene comprising contacting an aliphatic mono-unsaturated carboxylic acid with an Fdc1 polypeptide comprising an amino acid sequence with at least 21% sequence identity to SEQ ID NO: 1 and a Pad1 polypeptide comprising an amino acid sequence with at least 17% sequence identity to SEQ ID NO: 2.

20 Claims, 6 Drawing Sheets

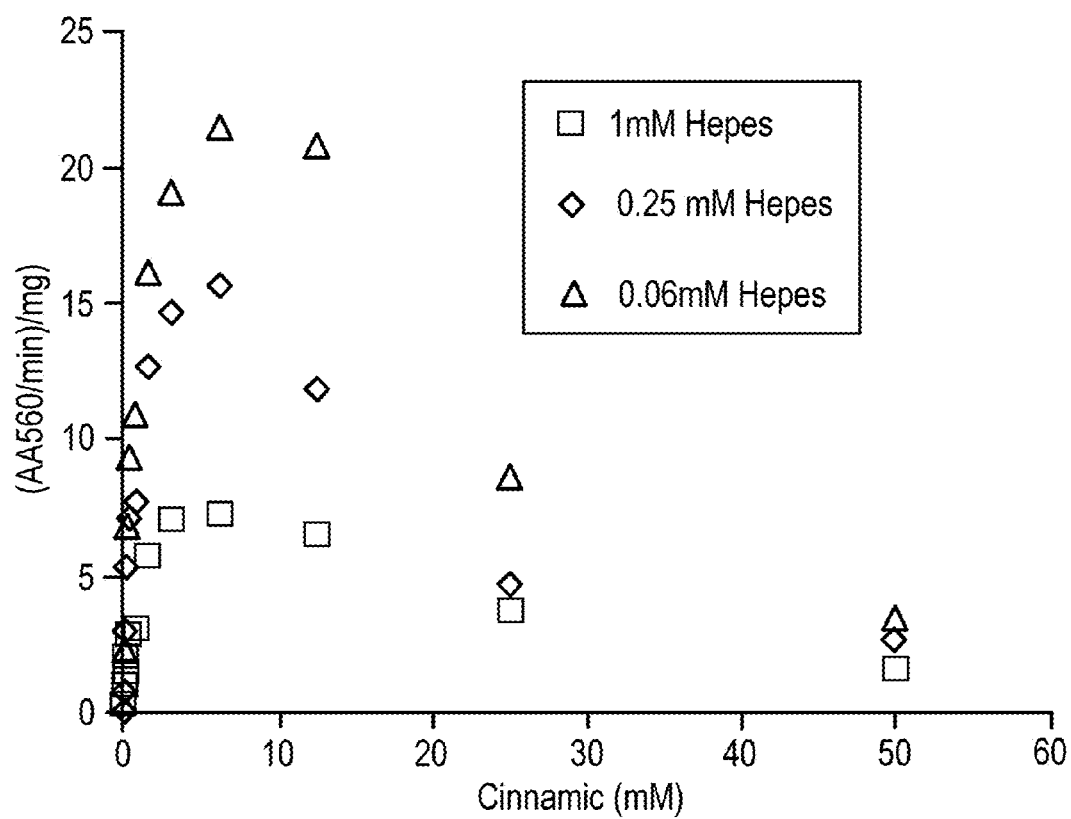

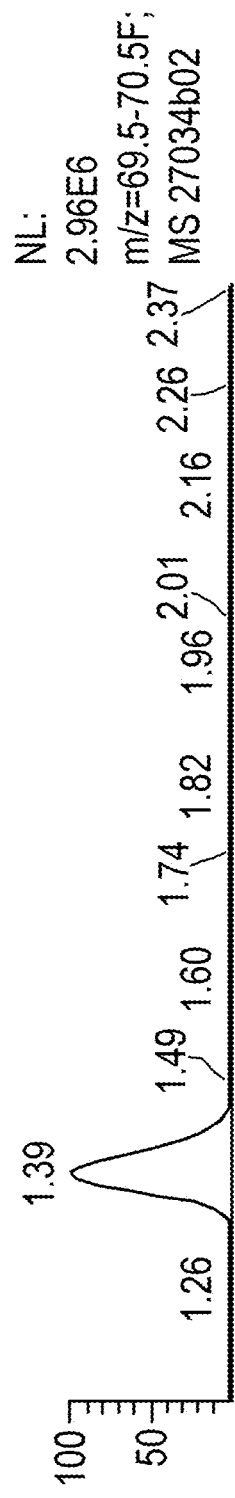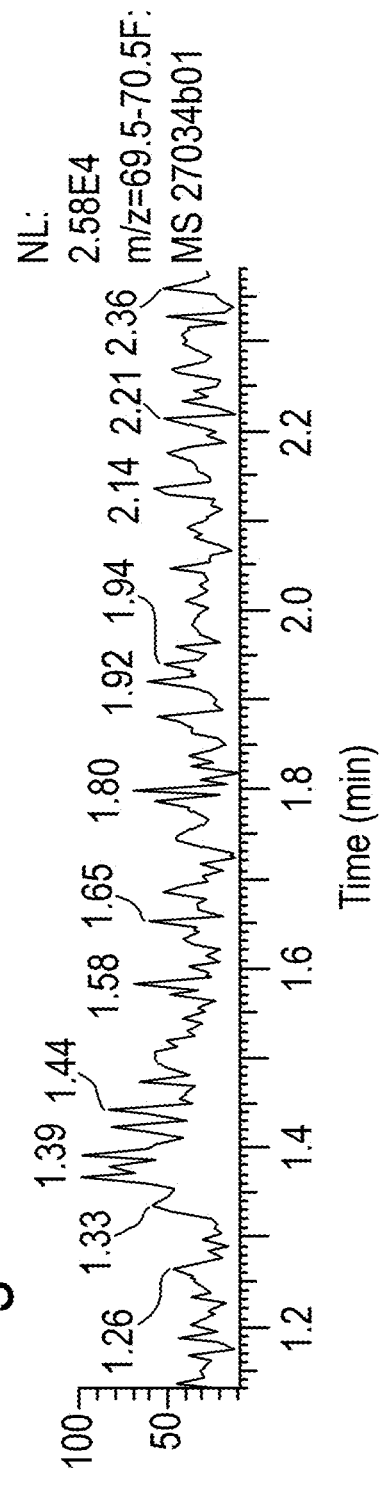

SEQUENCE LISTING

```
<160> NUMBER OF SEQ ID NOS: 59

<210> SEQ ID NO 1
<211> LENGTH: 503
<212> TYPE: PRT
<213> ORGANISM: Saccharomyces cerevisiae

<400> SEQUENCE: 1

Met Arg Lys Leu Asn Pro Ala Leu Glu Phe Arg Asp Phe Ile Gln Val
1               5                   10                  15

Leu Lys Asp Glu Asp Leu Ile Glu Ile Thr Glu Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Glu Lys Glu Pro Leu
            100                 105                 110

Pro Pro Ile Thr Val Pro Val Ser Ser Ala Pro Cys Lys Thr His Ile
        115                 120                 125

Leu Ser Glu Glu Lys Ile His Leu Gln Ser Leu Pro Thr Pro Tyr Leu
    130                 135                 140

His Val Ser Asp Gly Gly Lys Tyr Leu Gln Thr Tyr Gly Met Trp Ile
145                 150                 155                 160
```

```
Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Lys Pro Gln
            180                 185                 190

His Ile Arg Gln Ile Ala Asp Ser Trp Ala Ala Ile Gly Lys Ala Asn
        195                 200                 205

Glu Ile Pro Phe Ala Leu Cys Phe Gly Val Pro Ala Ala Ile Leu
    210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Lys Cys Glu Thr Asn
                245                 250                 255

Asp Leu Met Val Pro Ala Thr Ser Glu Met Val Phe Glu Gly Thr Leu
            260                 265                 270

Ser Leu Thr Asp Thr His Leu Glu Gly Pro Phe Gly Glu Met His Gly
        275                 280                 285

Tyr Val Phe Lys Ser Gln Gly His Pro Cys Pro Leu Tyr Thr Val Lys
    290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Glu Ser Gly Leu Pro Ile Leu Asp Ala
            340                 345                 350

Phe Met Pro Tyr Glu Ala Gln Ala Leu Trp Leu Ile Leu Lys Val Asp
        355                 360                 365

Leu Lys Gly Leu Gln Ala Leu Lys Thr Thr Pro Glu Glu Phe Cys Lys
    370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
                405                 410                 415

Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
        435                 440                 445

Ser Ser Arg Ser Lys Thr Met Lys Gly Gly Lys Cys Val Thr Asn Cys
    450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
                485                 490                 495

Trp Lys Arg Tyr Gly Tyr Lys
                500

<210> SEQ ID NO 2
<211> LENGTH: 242
<212> TYPE: PRT
<213> ORGANISM: Saccharomyces cerevisiae

<400> SEQUENCE: 2

Met Leu Leu Phe Pro Arg Arg Thr Asn Ile Ala Phe Phe Lys Thr Thr
1               5                   10                  15

Gly Ile Phe Ala Asn Phe Pro Leu Leu Gly Arg Thr Ile Thr Thr Ser
```

```
                    20                  25                  30
Pro Ser Phe Leu Thr His Lys Leu Ser Lys Glu Val Thr Arg Ala Ser
            35                  40                  45

Thr Ser Pro Pro Arg Pro Lys Arg Ile Val Val Ala Ile Thr Gly Ala
 50                  55                  60

Thr Gly Val Ala Leu Gly Ile Arg Leu Leu Gln Val Leu Lys Glu Leu
 65                  70                  75                  80

Ser Val Glu Thr His Leu Val Ile Ser Lys Trp Gly Ala Ala Thr Met
                85                  90                  95

Lys Tyr Glu Thr Asp Trp Glu Pro His Asp Val Ala Ala Leu Ala Thr
            100                 105                 110

Lys Thr Tyr Ser Val Arg Asp Val Ser Ala Cys Ile Ser Ser Gly Ser
        115                 120                 125

Phe Gln His Asp Gly Met Ile Val Val Pro Cys Ser Met Lys Ser Leu
    130                 135                 140

Ala Ala Ile Arg Ile Gly Phe Thr Glu Asp Leu Ile Thr Arg Ala Ala
145                 150                 155                 160

Asp Val Ser Ile Lys Glu Asn Arg Lys Leu Leu Leu Val Thr Arg Glu
                165                 170                 175

Thr Pro Leu Ser Ser Ile His Leu Glu Asn Met Leu Ser Leu Cys Arg
            180                 185                 190

Ala Gly Val Ile Ile Phe Pro Pro Val Pro Ala Phe Tyr Thr Arg Pro
        195                 200                 205

Lys Ser Leu His Asp Leu Leu Glu Gln Ser Val Gly Arg Ile Leu Asp
    210                 215                 220

Cys Phe Gly Ile His Ala Asp Thr Phe Pro Arg Trp Glu Gly Ile Lys
225                 230                 235                 240

Ser Lys

<210> SEQ ID NO 3
<211> LENGTH: 1512
<212> TYPE: DNA
<213> ORGANISM: Artificial Sequence
<220> FEATURE:
<223> OTHER INFORMATION: Codon-optimised sequence

<400> SEQUENCE: 3
atgcgcaaac tgaacccggc tctggaattc cgtgatttta ccaagtcct  gaaagacgaa      60 gacgacctga ttgaaattac cgaagaaatt gatccgaacc tggaagttgg cgcaatcatg     120
cgtaaagctt atgaatcaca cctgccggcg ccgctgttta aaatctgaa  aggtgccagt     180 aaagacctgt ttagcattct gggctgcccg gcgggtctgc gttcgaaaga aaaaggcgac     240
catggtcgca ttgcccatca cctgggcctg atccgaaaa  ccacgatcaa agaaattatc     300
gactatctgc tggaatgcaa agaaaaagaa ccgctgccgc gatcaccgt  tccggtcagc     360 tctgcgccgt gtaaaaccca tattctgagc gaagaaaaaa tccacctgca gtctctgccg     420
acgccgtacc tgcacgttag tgatggcggt aaatatctgc agacctacgg catgtggatt     480
ctgcaaaccc cggacaaaaa atggacgaac tggtccatcg cacgtggcat ggtggttgat     540
gacaaacaca ttaccggtct ggtgatcaaa ccgcagcata ttcgccaaat cgcggatagc     600
tgggcggcca ttggcaaagc gaatgaaatc ccgtttgcac tgtgctttgg tgtgccgccg     660
gcagctattc tggttagctc catgccgatc ccggaaggcg ttagcgaatc tgattatgtc     720
ggcgcgattc tgggtgaaag tgttccggtc gtgaaatgtg aaaccaacga cctgatggtc     780
```

| | |
|---|---|
| ccggccacga gtgaaatggt gtttgaaggt accctgtccc tgaccgatac gcatctggaa | 840 |
| ggcccgtttg gtgaaatgca cggctacgtt ttcaaaagcc agggtcatcc gtgcccgctg | 900 |
| tataccgtca aagcaatgtc ataccgtgat aacgctattc tgccggtgtc gaatccgggc | 960 |
| ctgtgtacgg acgaaaccca tacgctgatc ggtagcctgg tggcaaccga agctaaagaa | 1020 |
| ctggcaattg aatctggcct gccgatcctg gatgctttta tgccgtatga agcgcaggcc | 1080 |
| ctgtggctga ttctgaaagt tgacctgaaa ggtctgcaag ccctgaaaac cacgccggaa | 1140 |
| gaattctgca aaaaagtcgg cgatatttat tttcgcacca aagtgggttt catcgttcac | 1200 |
| gaaattatcc tggtggcaga tgacatcgac atcttcaact tcaaagaagt catctgggct | 1260 |
| tacgtgaccc gtcatacgcc ggttgcggat cagatggcct tgatgacgt cacctcattt | 1320 |
| ccgctggcac cgttcgtgtc acaatcatcg cgctcgaaaa cgatgaaagg cggtaaatgc | 1380 |
| gtgaccaact gtattttcg tcagcaatat gaacgctctt ttgattacat cacctgtaat | 1440 |
| ttcgaaaaag gttatccgaa aggtctggtg acaaagtga atgaaaactg gaaacgctat | 1500 |
| ggttacaaat ag | 1512 |

<210> SEQ ID NO 4
<211> LENGTH: 729
<212> TYPE: DNA
<213> ORGANISM: Artificial Sequence
<220> FEATURE:
<223> OTHER INFORMATION: Codon-optimised sequence

<400> SEQUENCE: 4

| | |
|---|---|
| atgctgctgt cccgcgtcg caccaatatc gctttcttca aaaccaccgg tatcttcgcc | 60 |
| aacttcccgc tgctgggtcg caccattacc acgtcaccgt cgtttctgac ccataaactg | 120 |
| agtaaagaag tcacccgtgc gagcacctct ccgccgcgtc cgaaacgtat tgtggttgcg | 180 |
| atcaccggcg ccacgggtgt tgcactgggc attcgcctgc tgcaggtcct gaaagaactg | 240 |
| agcgtggaaa cccatctggt tatctctaaa tggggtgcgg ccaccatgaa atatgaaacg | 300 |
| gattgggaac cgcacgacgt tgcagctctg gccaccaaaa cgtactcagt tcgtgatgtc | 360 |
| tcggcatgca ttagctctgg cagctttcaa cacgacggta tgatcgtcgt gccgtgtagt | 420 |
| atgaaatccc tggcggccat tcgtatcggc ttcaccgaag atctgattac gcgcgcagct | 480 |
| gacgtgtcta tcaaagaaaa ccgtaaactg ctgctggtta cccgcgaaac gccgctgagt | 540 |
| tccattcatc tggaaaatat gctgagcctg tgccgcgctg gcgtcattat cttcccgccg | 600 |
| gtgccggcct tctatacccg tccgaaaagt ctgcacgatc tgctgaaca gtccgtgggt | 660 |
| cgcatcctgg actgtttcgg cattcacgca gacacgtttc gcgctgggga aggtatcaaa | 720 |
| agcaaatag | 729 |

<210> SEQ ID NO 5
<211> LENGTH: 2729
<212> TYPE: DNA
<213> ORGANISM: Saccharomyces cerevisiae

<400> SEQUENCE: 5

| | |
|---|---|
| atgctcctat ttccaagaag aactaatata gccttttttca aaacaacagg cattttttgct | 60 |
| aatttttcctt tgctaggtag aaccattaca acttcaccat ctttccttac acataaactg | 120 |
| tcaaaggaag taaccagggc atcaacttcg cctccaagac caagagaat tgttgtcgca | 180 |
| attactggtg cgactggtgt tgcactggga atcagacttc tacaagtgct aaaagagttg | 240 |
| agcgtagaaa cccatttggt gatttcaaaa tggggtgcag caacaatgaa atatgaaaca | 300 |

-continued

```
gattgggaac cgcatgacgt ggcggccttg gcaaccaaga catactctgt tcgtgatgtt      360
tctgcatgca tttcgtccgg atctttccag catgatggta tgattgttgt gccctgttcc      420
atgaaatcac tagctgctat tagaatcggt tttacagagg atttaattac aagagctgcc      480
gatgtttcga ttaaagagaa tcgtaagtta ctactggtta ctcgggaaac ccctttatct      540
tccatccatc ttgaaaacat gttgtcttta tgcagggcag gtgttataat ttttcctccg      600
gtacctgcgt tttatacaag acccaagagc cttcatgacc tattagaaca aagtgttggc      660
aggatcctag actgctttgg catccacgct gacactttc ctcgttggga aggaataaaa       720
agcaagtaac acttttctg agcattttat tacgttactc aactactaat agagttgatt       780
tgttacttgc taaaatcttt ttatatttct tttagccccg acagaacttg ttgcaaatga      840
atacaaaccg tgaacttccc gatatcattc taattgaacc cagatatta cacatgtact       900 tcttactcat tttcaatgtc agcttaaata tcgtctaaaa caatatttta ctagatacgc      960
agttcaatct tcgcgcatat tttcacgaaa gtccaaattg cgtacgtagt tttatgtcaa     1020
agtgaccgcc gttgtagcgt acttttcct ataagacaag ctcgtgatat caggaatata     1080
tcaggaatgt aaacgaatac cgcatatctt tttgattttt ttcctctgag ttattctatt    1140
cttgacatta ttacatcacc aattcaaaag aattgtcaat ttatatattt aaatgaggaa     1200
gctaaatcca gctttagaat ttagagactt tatccaggtc ttaaaagatg aagatgactt     1260
aatcgaaatt accgaagaga ttgatccaaa tctcgaagta ggtgcaatta tgaggaaggc     1320
ctatgaatcc cacttaccag ccccgttatt taaaaatctc aaaggtgctt cgaaggatct     1380
tttcagcatt ttaggttgcc cagccggttt gagaagtaag gagaaaggag atcatggtag    1440
aattgcccat catctggggc tcgacccaaa acaactatc aaggaaatca tagattattt     1500
gctggagtgt aaggagaagg aacctctccc cccaatcact gttcctgtgt catctgcacc    1560
ttgtaaaaca catatacttt ctgaagaaaa aatacatcta caaagcctgc aacaccata     1620 tctacatgtt tcagacggtg gcaagtactt acaaacgtac ggaatgtgga ttcttcaaac    1680
tccagataaa aaatggacta attggtcaat tgctagaggt atggttgtag atgacaagca    1740
tatcactggt ctggtaatta aaccacaaca tattagacaa attgctgact cttgggcagc    1800
aattggaaaa gcaaatgaaa ttccttcgc gttatgtttt ggcgttcccc cagcagctat     1860
tttagttagt tccatgccaa ttcctgaagg tgtttctgaa tcggattatg ttggcgcaat    1920
cttgggtgag tcggttccag tagtaaaatg tgagaccaac gatttaatgg ttcctgcaac    1980
gagtgagatg gtatttgagg gtactttgtc cttaacagat acacatctgg aaggcccatt    2040
tggtgagatg catggatatg ttttcaaaag ccaaggtcat ccttgtccat tgtacactgt    2100
caaggctatg agttacagag acaatgctat tctacctgtt tcgaacccg gtctttgtac    2160 ggatgagaca cataccttga ttggttcact agtggctact gaggccaagg agctggctat    2220
tgaatctggc ttgccaattc tggatgcctt tatgccttat gaggctcagg ctctttggct    2280
tatcttaaag gtggatttga aagggctgca agcattgaag caacgcctg aagaattttg     2340 taagaaggta ggtgatattt actttaggac aaaagttggt tttatagtcc atgaaataat    2400
tttggtggca gatgatatcg acatatttaa cttcaaagaa gtcatctggg cctacgttac    2460
aagacataca cctgttgcag atcagatggc ttttgatgat gtcacttctt ttcctttggc    2520
tccctttgtt tcgcagtcat ccagaagtaa gactatgaaa ggtggaaagt gcgttactaa    2580
ttgcatattt agacagcaat atgagcgcag ttttgactac ataacttgta attttgaaaa    2640
```

```
gggatatccaa aaaggattag ttgacaaagt aaatgaaaat tggaaaaggt acggatataa    2700
ataattgcca tagactttct acggaagaa                                       2729

<210> SEQ ID NO 6
<211> LENGTH: 1512
<212> TYPE: DNA
<213> ORGANISM: Saccharomyces cerevisiae

<400> SEQUENCE: 6
atgaggaagc taaatccagc tttagaattt agagacttta tccaggtctt aaaagatgaa      60
gatgacttaa tcgaaattac cgaagagatt gatccaaatc tcgaagtagg tgcaattatg     120
aggaaggcct atgaatccca cttaccagcc ccgttattta aaaatctcaa aggtgcttcg     180
aaggatcttt tcagcatttt aggttgccca gccggtttga aagtaagga gaaaggagat     240 catggtagaa ttgcccatca tctggggctc gacccaaaaa caactatcaa ggaaatcata     300
gattatttgc tggagtgtaa ggagaaggaa cctctccccc caatcactgt tcctgtgtca     360
tctgcacctt gtaaaacaca tatactttct gaagaaaaaa tacatctaca aagcctgcca     420
acaccatatc tacatgtttc agacggtggc aagtacttac aaacgtacgg aatgtggatt     480
cttcaaactc cagataaaaa atggactaat tggtcaattg ctagaggtat ggttgtagat     540
gacaagcata tcactggtct ggtaattaaa ccacaacata ttagacaaat tgctgactct     600
tgggcagcaa ttgaaaagc aaatgaaatt cctttcgcgt tatgttttgg cgttccccca     660
gcagctattt tagttagttc catgccaatt cctgaaggtg tttctgaatc ggattatgtt     720
ggcgcaatct gggtgagtc ggttccagta gtaaatgtg agaccaacga tttaatggtt     780
cctgcaacga gtgagatggt atttgagggt actttgtcct taacagatac acatctggaa     840
ggcccatttg gtgagatgca tggatatgtt ttcaaaagcc aaggtcatcc ttgtccattg     900
tacactgtca aggctatgag ttacagagac aatgctattc tacctgtttc gaaccccggt     960
ctttgtacgg atgagacaca taccttgatt ggttcactag tggctactga ggccaaggag    1020
ctggctattg aatctggctt gccaattctg gatgccttta tgccttatga ggctcaggct    1080
ctttggctta tcttaaaggt ggatttgaaa gggctgcaag cattgaagac aacgcctgaa    1140
gaattttgta agaaggtagg tgatatttac tttaggacaa aagttggttt tatagtccat    1200
gaaataattt tggtggcaga tgatatcgac atatttaact tcaaagaagt catctgggcc    1260
tacgttacaa gacatacacc tgttgcagat cagatggctt ttgatgatgt cacttctttt    1320
cctttggctc cctttgtttc gcagtcatcc agaagtaaga ctatgaaagg tggaaagtgc    1380
gttactaatt gcatatttag acagcaatat gagcgcagtt ttgactacat aacttgtaat    1440
tttgaaaagg gatatccaaa aggattagtt gacaaagtaa atgaaaattg gaaaaggtac    1500
ggatataaat aa                                                        1512

<210> SEQ ID NO 7
<211> LENGTH: 729
<212> TYPE: DNA
<213> ORGANISM: Saccharomyces cerevisiae

<400> SEQUENCE: 7
atgctcctat ttccaagaag aactaatata gccttttca aaacaacagg cattttgct      60 aattttcctt tgctaggtag aaccattaca acttcaccat ctttccttac acataaactg    120
tcaaaggaag taaccagggc atcaacttcg cctccaaagc caaagagaat tgttgtcgca    180
attactggtg cgactggtgt tgcactggga atcagacttc tacaagtgct aaaagagttg    240
```

```
agcgtagaaa cccatttggt gatttcaaaa tggggtgcag caacaatgaa atatgaaaca      300
gattgggaac cgcatgacgt ggcggccttg gcaaccaaga catactctgt tcgtgatgtt      360
tctgcatgca tttcgtccgg atctttccag catgatggta tgattgttgt gccctgttcc      420
atgaaatcac tagctgctat tagaatcggt tttacagagg atttaattac aagagctgcc      480
gatgtttcga ttaaagagaa tcgtaagtta ctactggtta ctcgggaaac ccctttatct      540
tccatccatc ttgaaaacat gttgtcttta tgcagggcag gtgttataat ttttcctccg      600
gtacctgcgt tttatacaag acccaagagc cttcatgacc tattagaaca aagtgttggc      660
aggatcctag actgctttgg catccacgct gacactttc ctcgttggga aggaataaaa       720
agcaagtaa                                                              729
```

<210> SEQ ID NO 8
<211> LENGTH: 40
<212> TYPE: DNA
<213> ORGANISM: Artificial Sequence
<220> FEATURE:
<223> OTHER INFORMATION: Amplification primer

<400> SEQUENCE: 8

```
ggatccgaat tcgagctcga tgctgctgtt cccgcgtcgc                             40
```

<210> SEQ ID NO 9
<211> LENGTH: 46
<212> TYPE: DNA
<213> ORGANISM: Artificial Sequence
<220> FEATURE:
<223> OTHER INFORMATION: Amplification primer

<400> SEQUENCE: 9

```
ttctgttcga cttaagctat ttgcttttga taccttccca gcgcgg                      46
```

<210> SEQ ID NO 10
<211> LENGTH: 39
<212> TYPE: DNA
<213> ORGANISM: Artificial Sequence
<220> FEATURE:
<223> OTHER INFORMATION: Amplification primer

<400> SEQUENCE: 10

```
gaaggagata tacatatgct gctgttcccg cgtcgcacc                              39
```

<210> SEQ ID NO 11
<211> LENGTH: 46
<212> TYPE: DNA
<213> ORGANISM: Artificial Sequence
<220> FEATURE:
<223> OTHER INFORMATION: Amplification primer

<400> SEQUENCE: 11

```
ctttaccaga ctcgagctat ttgcttttga taccttccca gcgcgg                      46
```

<210> SEQ ID NO 12
<211> LENGTH: 43
<212> TYPE: DNA
<213> ORGANISM: Artificial Sequence
<220> FEATURE:
<223> OTHER INFORMATION: Amplification primer

<400> SEQUENCE: 12

```
caggatccga attcgagctc gatgcgcaaa ctgaacccgg ctc                         43
```

<210> SEQ ID NO 13
<211> LENGTH: 43
<212> TYPE: DNA
<213> ORGANISM: Artificial Sequence
<220> FEATURE:
<223> OTHER INFORMATION: Amplification primer

<400> SEQUENCE: 13
ttctgttcga cttaagctat tgtaaccat agcgtttcca gtt                43

<210> SEQ ID NO 14
<211> LENGTH: 38
<212> TYPE: DNA
<213> ORGANISM: Artificial Sequence
<220> FEATURE:
<223> OTHER INFORMATION: Amplification primer

<400> SEQUENCE: 14
tcgaaggtag gcatatgctg ctgttcccgc gtcgcacc                    38

<210> SEQ ID NO 15
<211> LENGTH: 46
<212> TYPE: DNA
<213> ORGANISM: Artificial Sequence
<220> FEATURE:
<223> OTHER INFORMATION: Amplification primer

<400> SEQUENCE: 15
attcggatcc ctcgagctat ttgcttttga taccttccca gcgcgg          46

<210> SEQ ID NO 16
<211> LENGTH: 503
<212> TYPE: PRT
<213> ORGANISM: Saccharomyces cerevisiae

<400> SEQUENCE: 16

```
Met Arg Lys Leu Asn Pro Ala Leu Glu Phe Arg Asp Phe Ile Gln Val
1               5                   10                  15

Leu Lys Asp Glu Asp Leu Ile Glu Ile Thr Glu Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Glu Lys Glu Pro Leu
            100                 105                 110

Pro Pro Ile Thr Val Pro Val Ser Ser Ala Pro Cys Lys Thr His Ile
        115                 120                 125

Leu Ser Glu Glu Lys Ile His Leu Gln Ser Leu Pro Thr Pro Tyr Leu
    130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Lys Pro Gln
            180                 185                 190
```

```
His Ile Arg Gln Ile Ala Asp Ser Trp Ala Ile Gly Lys Ala Asn
            195                 200                 205

Glu Ile Pro Phe Ala Leu Cys Phe Gly Val Pro Ala Ala Ile Leu
210                 215                 220

Ile Ser Ser Met Pro Ile Pro Glu Gly Val Ser Glu Ser Asp Tyr Val
225                 230                 235                 240

Gly Ala Ile Leu Gly Glu Ser Val Pro Val Lys Cys Glu Thr Asn
                245                 250                 255

Asp Leu Met Val Pro Ala Thr Ser Glu Met Val Phe Glu Gly Thr Leu
                260                 265                 270

Ser Leu Thr Asp Thr His Leu Glu Gly Pro Phe Gly Met His Gly
            275                 280                 285

Tyr Val Phe Lys Ser Gln Gly His Pro Cys Pro Leu Tyr Thr Val Lys
290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Glu Ser Gly Leu Pro Ile Leu Asp Ala
            340                 345                 350

Phe Met Pro Tyr Glu Ala Gln Ala Leu Trp Leu Ile Leu Lys Val Asp
            355                 360                 365

Leu Lys Gly Leu Gln Ala Leu Lys Thr Thr Pro Glu Glu Phe Cys Lys
370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
                405                 410                 415

Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
            435                 440                 445

Ser Ser Arg Ser Lys Thr Met Lys Gly Gly Lys Cys Val Thr Asn Cys
450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
                485                 490                 495

Trp Lys Arg Tyr Gly Tyr Lys
            500

<210> SEQ ID NO 17
<211> LENGTH: 503
<212> TYPE: PRT
<213> ORGANISM: Saccharomyces cerevisiae
<220> FEATURE:
<221> NAME/KEY: misc_feature
<222> LOCATION: (277)..(277)
<223> OTHER INFORMATION: Xaa can be any naturally occurring amino acid

<400> SEQUENCE: 17

Met Arg Lys Leu Asn Pro Ala Leu Glu Phe Arg Asp Phe Ile Gln Val
1               5                   10                  15

Leu Lys Asp Glu Asp Asp Leu Ile Glu Ile Thr Glu Glu Ile Asp Pro
            20                  25                  30
```

-continued

Asn Leu Glu Val Gly Ala Ile Met Arg Lys Ala Tyr Glu Ser His Leu
         35                  40                  45

Pro Ala Pro Leu Phe Lys Asn Leu Lys Gly Ala Ser Lys Asp Leu Phe
 50                  55                  60

Ser Ile Leu Gly Cys Pro Ala Gly Leu Arg Ser Lys Glu Lys Gly Asp
 65                  70                  75                  80

His Gly Arg Ile Ala His His Leu Gly Leu Asp Pro Lys Thr Thr Ile
                 85                  90                  95

Lys Glu Ile Ile Asp Tyr Leu Leu Glu Cys Lys Glu Lys Glu Pro Leu
                100                 105                 110

Pro Pro Ile Thr Val Pro Val Ser Ser Ala Pro Cys Lys Thr His Ile
             115                 120                 125

Leu Ser Glu Glu Lys Ile His Leu Gln Ser Leu Pro Thr Pro Tyr Leu
130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Asp Asp Lys His Ile Thr Gly Leu Val Ile Lys Pro Gln
             180                 185                 190

His Ile Arg Gln Ile Ala Asp Ser Trp Ala Ala Ile Gly Lys Ala Asn
             195                 200                 205

Glu Ile Pro Phe Ala Leu Cys Phe Gly Val Pro Pro Ala Ala Ile Leu
    210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Val Lys Cys Glu Thr Asn
                245                 250                 255

Asp Leu Met Val Pro Ala Thr Ser Glu Met Val Phe Glu Gly Thr Leu
             260                 265                 270

Ser Leu Thr Asp Xaa His Leu Glu Gly Pro Phe Gly Glu Met His Gly
         275                 280                 285

Tyr Val Phe Lys Ser Gln Gly His Pro Cys Pro Leu Tyr Thr Val Lys
    290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Glu Ser Gly Leu Pro Ile Leu Asp Ala
             340                 345                 350

Phe Met Pro Tyr Glu Ala Gln Ala Leu Trp Leu Ile Leu Lys Val Asp
         355                 360                 365

Leu Lys Gly Leu Gln Ala Leu Lys Thr Thr Pro Glu Glu Phe Cys Lys
    370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
                405                 410                 415

Val Ile Trp Ala Tyr Val Thr Arg His Thr Pro Val Ala Asp Gln Met
             420                 425                 430

Ala Phe Asp Asp Val Thr Ser Phe Pro Leu Ala Pro Phe Val Ser Gln
         435                 440                 445

Ser Ser Arg Ser Lys Thr Met Lys Gly Gly Lys Cys Val Thr Asn Cys

```
                450             455             460
Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
                485                 490                 495

Trp Lys Arg Tyr Gly Tyr Lys
                500

<210> SEQ ID NO 18
<211> LENGTH: 503
<212> TYPE: PRT
<213> ORGANISM: Saccharomyces cerevisiae

<400> SEQUENCE: 18

Met Arg Lys Leu Asn Pro Ala Leu Glu Phe Arg Asp Phe Ile Gln Val
1               5                   10                  15

Leu Lys Asp Glu Asp Leu Ile Glu Ile Thr Glu Glu Ile Asp Pro
                20                  25                  30

Asn Leu Glu Val Gly Ala Ile Met Arg Lys Ala Tyr Glu Ser His Leu
                35                  40                  45

Pro Ala Pro Leu Phe Lys Asn Leu Lys Gly Ala Ser Lys Asp Leu Phe
50                  55                  60

Ser Ile Leu Gly Cys Pro Ala Gly Leu Arg Ser Lys Glu Lys Gly Asp
65                  70                  75                  80

His Gly Arg Ile Ala His Leu Gly Leu Asp Pro Lys Thr Thr Ile
                85                  90                  95

Lys Glu Ile Ile Asp Tyr Leu Leu Glu Cys Lys Glu Lys Glu Pro Leu
                100                 105                 110

Pro Pro Ile Thr Val Pro Val Ser Ser Ala Pro Cys Lys Thr His Ile
                115                 120                 125

Leu Ser Glu Glu Lys Ile His Leu Gln Ser Leu Pro Thr Pro Tyr Leu
                130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Lys Pro Gln
                180                 185                 190

His Ile Arg Gln Ile Ala Asp Ser Trp Ala Ala Ile Gly Lys Ala Asn
                195                 200                 205

Glu Ile Pro Phe Ala Leu Cys Phe Gly Val Pro Ala Ala Ile Leu
                210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Lys Cys Glu Thr Asn
                245                 250                 255

Asp Leu Met Val Pro Ala Thr Ser Glu Met Val Phe Glu Gly Thr Leu
                260                 265                 270

Ser Leu Thr Asp Thr His Leu Glu Gly Pro Phe Gly Glu Met His Gly
                275                 280                 285

Tyr Val Phe Lys Ser Gln Gly His Ala Cys Pro Leu Tyr Thr Val Lys
                290                 295                 300

Ala Met Ser Tyr Arg Asp Asn Ala Ile Leu Pro Val Ser Asn Pro Gly
305                 310                 315                 320
```

```
Leu Cys Thr Asp Glu Thr His Thr Leu Ile Gly Ser Leu Val Ala Thr
            325                 330                 335

Glu Ala Lys Glu Leu Ala Ile Glu Ser Gly Leu Pro Ile Leu Asp Ala
        340                 345                 350

Phe Met Pro Tyr Glu Ala Gln Ala Leu Trp Leu Ile Leu Lys Val Asp
            355                 360                 365

Leu Lys Gly Leu Gln Ala Leu Lys Thr Thr Pro Glu Glu Phe Cys Lys
        370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
                405                 410                 415

Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
        435                 440                 445

Ser Ser Arg Ser Lys Thr Met Lys Gly Lys Cys Val Thr Asn Cys
    450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
                485                 490                 495

Trp Lys Arg Tyr Gly Tyr Lys
            500
```

<210> SEQ ID NO 19
<211> LENGTH: 503
<212> TYPE: PRT
<213> ORGANISM: Saccharomyces cerevisiae
<220> FEATURE:
<221> NAME/KEY: misc_feature
<222> LOCATION: (292)..(292)
<223> OTHER INFORMATION: Xaa can be any naturally occurring amino acid

<400> SEQUENCE: 19

```
Met Arg Lys Leu Asn Pro Ala Leu Glu Phe Arg Asp Phe Ile Gln Val
1               5                   10                  15

Leu Lys Asp Glu Asp Leu Ile Glu Ile Thr Glu Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Glu Lys Glu Pro Leu
            100                 105                 110

Pro Pro Ile Thr Val Pro Val Ser Ser Ala Pro Cys Lys Thr His Ile
        115                 120                 125

Leu Ser Glu Glu Lys Ile His Leu Gln Ser Leu Pro Thr Pro Tyr Leu
    130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
```

```
            165                 170                 175
Met Val Asp Asp Lys His Ile Thr Gly Leu Val Ile Lys Pro Gln
        180                 185                 190

His Ile Arg Gln Ile Ala Asp Ser Trp Ala Ala Ile Gly Lys Ala Asn
    195                 200                 205

Glu Ile Pro Phe Ala Leu Cys Phe Gly Val Pro Ala Ala Ile Leu
    210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Lys Cys Glu Thr Asn
                245                 250                 255

Asp Leu Met Val Pro Ala Thr Ser Glu Met Val Phe Glu Gly Thr Leu
                260                 265                 270

Ser Leu Thr Asp Thr His Leu Glu Gly Pro Phe Gly Glu Met His Gly
                275                 280                 285

Tyr Val Phe Xaa Ser Gln Gly His Pro Cys Pro Leu Tyr Thr Val Lys
            290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Glu Ser Gly Leu Pro Ile Leu Asp Ala
            340                 345                 350

Phe Met Pro Tyr Glu Ala Gln Ala Leu Trp Leu Ile Leu Lys Val Asp
            355                 360                 365

Leu Lys Gly Leu Gln Ala Leu Lys Thr Thr Pro Glu Glu Phe Cys Lys
370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
                405                 410                 415

Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
        435                 440                 445

Ser Ser Arg Ser Lys Thr Met Lys Gly Gly Lys Cys Val Thr Asn Cys
450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
                485                 490                 495

Trp Lys Arg Tyr Gly Tyr Lys
            500

<210> SEQ ID NO 20
<211> LENGTH: 503
<212> TYPE: PRT
<213> ORGANISM: Saccharomyces cerevisiae

<400> SEQUENCE: 20

Met Ser Ala Leu Asn Pro Ala Leu Gln Phe Arg Asp Phe Ile Gln Val
1               5                   10                  15

Leu Lys Asp Glu Asp Leu Ile Glu Ile Thr Lys Gly Val Asp Pro
            20                  25                  30
```

Asn Leu Glu Val Gly Ala Ile Met Arg Lys Ala Tyr Glu Ser Lys Leu
         35                  40                  45

Pro Ala Pro Leu Phe Lys Asn Ile Lys Gly Ala Ser Lys Asp Leu Phe
 50                  55                  60

Asn Ile Leu Gly Cys Pro Ala Gly Leu Arg Asn Lys Lys Lys Gly Asp
65                  70                  75                  80

His Gly Arg Ile Ala His His Leu Gly Leu Asp Pro Lys Thr Thr Ile
                 85                  90                  95

Lys Glu Ile Ile Asp Tyr Leu Leu Glu Cys Lys Asn Lys Lys Pro Leu
                100                 105                 110

Pro Pro Ser Ser Ile Ser Ala Ser Ser Ala Pro Cys Lys Ala His Val
             115                 120                 125

Leu Ser Glu Glu Glu Ile His Leu Glu Ser Leu Pro Thr Pro Tyr Leu
        130                 135                 140

His Thr Ser Asp Gly Gly Asn Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Lys Pro Gln
                180                 185                 190

His Ile Arg Gln Ile Ala Asp Ala Trp Gly Ala Ile Gly Lys Gly Asn
            195                 200                 205

Lys Ile Pro Phe Ala Leu Cys Phe Gly Val Pro Pro Ala Ala Ile Leu
        210                 215                 220

Val Ser Ser Met Pro Ile Pro Glu Gly Val Ser Glu Ser Asp Tyr Val
225                 230                 235                 240

Gly Ala Ile Leu Gly Lys Pro Val Pro Val Val Lys Cys Glu Thr Asn
                245                 250                 255

Asp Leu Met Val Pro Ala Thr Ser Glu Ile Val Phe Glu Gly Thr Leu
                260                 265                 270

Ser Leu Thr Asp Thr His Ala Glu Gly Pro Phe Gly Glu Met His Gly
        275                 280                 285

Tyr Val Phe Gly Gly Gln Gly His Pro Cys Pro Leu Tyr Thr Val Lys
        290                 295                 300

Ala Met Thr His Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Lys Ser Gly Leu Pro Val Leu Asp Ala
            340                 345                 350

Phe Thr Pro Tyr Glu Ala Gln Ala Leu Trp Leu Val Leu Lys Val Asp
        355                 360                 365

Leu Lys Arg Leu Gln Ala Leu Lys Thr Thr Pro Glu Glu Phe Ser Lys
        370                 375                 380

Lys Val Gly Asp Ile Tyr Phe Arg Thr Lys Val Gly Phe Ile Ile His
385                 390                 395                 400

Glu Ile Val Leu Val Ala Asp Asp Ile Asp Ile Phe Asn Phe Lys Glu
                405                 410                 415

Val Phe Trp Ala Tyr Val Thr Arg His Thr Pro Val Ala Asp Gln Thr
                420                 425                 430

Ala Phe Asp Asp Val Thr Ser Phe Pro Leu Ala Pro Phe Val Ser Gln
            435                 440                 445

Ser Pro Arg Ser Lys Thr Met Lys Gly Gly Lys Cys Val Thr Asn Cys

```
                450             455             460
Ile Phe Arg Gln Gln Tyr Glu Arg Asp Phe Asp Tyr Val Thr Cys Ser
465                 470                 475                 480

Phe Glu Lys Gly Tyr Ser Lys Glu Leu Val Asp Arg Ile Asn Glu Asn
                485                 490                 495

Trp Arg Glu Tyr Gly Tyr Lys
            500

<210> SEQ ID NO 21
<211> LENGTH: 346
<212> TYPE: PRT
<213> ORGANISM: Saccharomyces cerevisiae

<400> SEQUENCE: 21

Met Trp Ile Leu Gln Thr Pro Asp Lys Lys Trp Thr Asn Trp Ser Ile
1               5                   10                  15

Ala Arg Gly Met Val Asp Asp Lys His Ile Thr Gly Leu Val Ile
                20                  25                  30

Lys Pro Gln His Ile Arg Gln Ile Ala Asp Ser Trp Ala Ala Ile Gly
            35                  40                  45

Lys Ala Asn Glu Ile Pro Phe Ala Leu Cys Phe Gly Val Pro Pro Ala
        50                  55                  60

Ala Ile Leu Val Ser Ser Met Pro Ile Pro Glu Gly Val Ser Glu Ser
65                  70                  75                  80

Asp Tyr Val Gly Ala Ile Leu Gly Glu Ser Val Pro Val Val Lys Cys
                85                  90                  95

Glu Thr Asn Asp Leu Met Val Pro Ala Thr Ser Glu Met Val Phe Glu
            100                 105                 110

Gly Thr Leu Ser Leu Thr Asp Thr His Leu Glu Gly Pro Phe Gly Glu
        115                 120                 125

Met His Gly Tyr Val Phe Lys Ser Gln Gly His Pro Cys Pro Leu Tyr
    130                 135                 140

Thr Val Lys Ala Met Ser Tyr Arg Asp Asn Ala Ile Leu Pro Val Ser
145                 150                 155                 160

Asn Pro Gly Leu Cys Thr Asp Glu Thr His Thr Leu Ile Gly Ser Leu
                165                 170                 175

Val Ala Thr Glu Ala Lys Glu Leu Ala Ile Glu Ser Gly Leu Pro Ile
            180                 185                 190

Leu Asp Ala Phe Met Pro Tyr Glu Ala Gln Ala Leu Trp Leu Ile Leu
        195                 200                 205

Lys Val Asp Leu Lys Gly Leu Gln Ala Leu Lys Thr Thr Pro Glu Glu
    210                 215                 220

Phe Cys Lys Lys Val Gly Asp Ile Tyr Phe Arg Thr Lys Val Gly Phe
225                 230                 235                 240

Ile Val His Glu Ile Ile Leu Val Ala Asp Asp Ile Asp Ile Phe Asn
                245                 250                 255

Phe Lys Glu Val Ile Trp Ala Tyr Val Thr Arg His Thr Pro Val Ala
            260                 265                 270

Asp Gln Met Ala Phe Asp Val Thr Ser Phe Pro Leu Ala Pro Phe
        275                 280                 285

Val Ser Gln Ser Ser Arg Ser Lys Thr Met Lys Gly Lys Cys Val
    290                 295                 300

Thr Asn Cys Ile Phe Arg Gln Gln Tyr Glu Arg Ser Phe Asp Tyr Ile
305                 310                 315                 320
```

```
Thr Cys Asn Phe Glu Lys Gly Tyr Pro Lys Gly Leu Val Asp Lys Val
            325                 330                 335

Asn Asp Asn Trp Lys Arg Tyr Gly Tyr Lys
        340                 345

<210> SEQ ID NO 22
<211> LENGTH: 513
<212> TYPE: PRT
<213> ORGANISM: Debaryomyces hansenii

<400> SEQUENCE: 22

Met Ser Asn Leu Arg Pro Glu Leu Arg Phe Arg Asp Phe Leu Gln Val
1               5                   10                  15

Leu Lys Asn Glu Asn Asp Leu Val Glu Ile Thr His Glu Cys Asp Pro
            20                  25                  30

Asn Leu Glu Val Gly Ala Ile Met Arg Lys Val Tyr Glu Glu Lys Leu
        35                  40                  45

Pro Val Pro Leu Phe Lys Asn Leu Lys Lys Asp Pro Lys Asn Pro Asp
    50                  55                  60

Pro Ser Asn Leu Phe Asn Ile Val Gly Cys Leu Gly Gly Leu Arg Asp
65                  70                  75                  80

Ala Lys Lys Asp Asn Asp His Ala Arg Ile Ala Leu His Leu Gly Leu
                85                  90                  95

Asp Ser Gln Thr Pro Met Thr Lys Ile Ile Asp Tyr Leu Ile Glu Ala
            100                 105                 110

Asn Thr Lys Lys Pro Leu Pro Pro Val Leu Leu Glu Asp Ala Ser Gly
        115                 120                 125

Ala Pro Cys Lys Lys Asn Lys Ile Ser Gly Asp Val Ile Arg Leu Asn
    130                 135                 140

Ala Leu Pro Ala Pro Thr Leu His His Gly Asp Gly Lys Tyr Ile
145                 150                 155                 160

Gln Thr Tyr Gly Met Phe Val Leu Gln Thr Ala Asp Lys Thr Trp Thr
                165                 170                 175

Asn Trp Ser Ile Ala Arg Gly Met Ile Tyr Asp Asp Lys His Leu Thr
            180                 185                 190

Gly Leu Val Met Asn Pro Gln His Ile Arg Arg Val Ala Asp Thr Trp
        195                 200                 205

Ala Glu Ile Gly Met Gly Asp Ser Val Pro Phe Ala Leu Cys Phe Gly
    210                 215                 220

Val Pro Pro Ala Ser Ile Leu Val Ser Ser Met Pro Ile Pro Asp Gly
225                 230                 235                 240

Ala Thr Glu Ala Asp Tyr Ile Gly Ala Leu Val Gly Glu Pro Leu Ser
                245                 250                 255

Val Val Lys Cys Glu Thr Asn Asp Leu His Val Pro Ala Asp Ser Glu
            260                 265                 270

Met Val Phe Glu Gly Thr Leu Asn Leu Asn Lys Met Val Glu Glu Gly
        275                 280                 285

Pro Phe Gly Glu Met His Gly Tyr Cys Phe Pro Gly His Gly His Pro
    290                 295                 300

Cys Pro Leu Tyr Thr Val Asp Thr Ile Thr Tyr Arg Asp Asp Ala Ile
305                 310                 315                 320

Leu Pro Val Ser Asn Pro Gly Leu Cys Thr Asp Glu Thr His Thr Leu
                325                 330                 335

Ile Gly Gly Leu Val Ser Ala Glu Cys Lys Gln Met Ala Leu Glu His
            340                 345                 350
```

```
Pro Lys Leu Lys Ser Val Ile Met Glu Ala Phe Thr Pro His Glu Gly
            355                 360                 365

Val Ala Leu Trp Leu Ala Leu Lys Val Asn Thr Lys Glu Leu Ala Lys
        370                 375                 380

Leu Asn Thr Asn Ser Glu Asp Phe Cys Lys Leu Ile Gly Asp Tyr Tyr
385                 390                 395                 400

Tyr Ser Ser Lys Pro Gly Phe Ile Leu Gln Glu Ile Val Leu Gly
                405                 410                 415

Asp Asp Val Asp Ile Phe Asp Phe Arg Lys Leu Phe Trp Ala Tyr Ala
                420                 425                 430

Thr Arg His Thr Pro Gly Asp Asp Gln Tyr Met Phe Asn Asp Tyr Arg
            435                 440                 445

Ala Phe Pro Leu Ala Pro Phe Ile Gly Gln Gly Pro Arg Ile Lys Thr
        450                 455                 460

Leu Lys Gly Gly Asn Cys Val Thr Asp Cys Leu Phe Pro Lys Gln Tyr
465                 470                 475                 480

Glu Pro Glu Gly Val Asp Phe Val Thr Cys Asp Phe Asp Gly Tyr Asp
                485                 490                 495

Glu Ala Ile Lys Glu Lys Val Arg Lys Asn Trp Ser Ala Tyr Gly Tyr
                500                 505                 510

Lys

<210> SEQ ID NO 23
<211> LENGTH: 511
<212> TYPE: PRT
<213> ORGANISM: Zygosaccharomyces rouxii

<400> SEQUENCE: 23

Met Ala Pro Lys Leu Thr Pro Val Leu Lys Phe Arg Asp Phe Leu Glu
1               5                   10                  15

Ala Leu Arg Arg Glu Gly Asp Leu Val Glu Ile Phe Gln Glu Val Asp
            20                  25                  30

Pro His Leu Glu Val Gly Ala Ile Met Arg Lys Val Tyr Glu Asn Lys
        35                  40                  45

Leu Pro Val Pro Leu Phe Lys Asn Leu Lys Gln Pro Lys Gly Asn Val
    50                  55                  60

Asp Pro Asp Asn Leu Phe Asp Ile Ala Gly Cys Ile Gly Gly Leu Arg
65                  70                  75                  80

Ala Phe Gly Asn Asp His Ala Arg Ile Ala His His Leu Gly Leu Ser
                85                  90                  95

Ser Asp Thr Gly Met Lys Glu Ile Ile Asp His Leu Leu Glu Ala Lys
            100                 105                 110

Lys Arg Lys Pro Ile Pro Pro Val Lys Val Asn Arg Asp Ser Ala Pro
        115                 120                 125

Cys Lys Glu Asn Ile Leu Lys Gly Asp Gln Ile Asn Leu Glu Gln Leu
    130                 135                 140

Pro Ala Pro Tyr Leu His Asp Glu Asp Gly Gly Lys Tyr Leu Gln Thr
145                 150                 155                 160

Tyr Gly Met Phe Val Leu Gln Thr Pro Asp Lys Ser Trp Thr Asn Trp
                165                 170                 175

Ser Ile Ala Arg Ala Met Ile His Asp Glu Lys His Leu Thr Gly Leu
            180                 185                 190

Val Met Asn Pro Gln His Ile Arg Arg Val Ala Asp Gln Trp Lys Thr
        195                 200                 205
```

Val Gly Lys Glu Asn Ala Val Pro Phe Ala Leu Cys Phe Gly Val Pro
    210                 215                 220

Pro Ala Ser Ile Leu Val Ser Ser Met Pro Ile Pro Glu Gly Val Ser
225                 230                 235                 240

Glu Ala Asp Tyr Ile Gly Ser Val Val Gly Glu Pro Ile Gln Val Val
                245                 250                 255

Gln Ala Glu Thr Asn Gln Leu Glu Val Pro Ala Glu Ser Glu Ile Val
            260                 265                 270

Leu Glu Gly Thr Leu Asn Leu Asp His Met Val Pro Glu Gly Pro Phe
        275                 280                 285

Gly Glu Met His Gly Tyr Val Phe Pro Gly Thr Gly His Pro Cys Pro
    290                 295                 300

Thr Tyr Thr Val Glu Thr Ile Ser Tyr Arg Asn Asn Ala Ile Leu Pro
305                 310                 315                 320

Val Ser Asn Pro Gly Leu Cys Thr Asp Glu Thr His Thr Leu Ile Gly
                325                 330                 335

Ser Leu Val Ala Ala Glu Ala Lys Gln Ile Cys Leu Asn His Pro Val
            340                 345                 350

Leu Ser Lys Ile Val Met Asp Ala Phe Met Pro Tyr Glu Ser Gln Val
        355                 360                 365

Leu Trp Leu Ala Phe Lys Ile Asn Val Lys Glu Leu Val Lys Leu Asn
    370                 375                 380

Thr Asp Ser Lys Ser Leu Ala Asp Leu Phe Ala Lys Glu Ile Tyr Gly
385                 390                 395                 400

Asn Lys Val Gly Met Thr Thr Gln Glu Ile Ile Leu Val Gly Asp Asp
                405                 410                 415

Ile Asp Ile Phe Asn Phe Lys Lys Leu Met Trp Ala Tyr Val Thr Arg
            420                 425                 430

His Thr Pro Gly Asp Asp Gln Tyr Phe Tyr Asp Glu Phe Val Ala Phe
        435                 440                 445

Pro Leu Ala Pro Phe Ile Ser Gln Gly Pro Arg Ile Lys Thr Lys Arg
    450                 455                 460

Gly Gly Asn Cys Val Thr Asp Cys Leu Phe Pro Ile Gln Tyr Arg Asp
465                 470                 475                 480

Pro Asn Phe Arg Phe Val Thr Cys Asp Phe Asp Ser Tyr Asp Ser Ala
                485                 490                 495

Ile Arg Asp Lys Ile Asn Gln Asn Trp Ser Asn Tyr Gly Tyr Gln
            500                 505                 510

<210> SEQ ID NO 24
<211> LENGTH: 513
<212> TYPE: PRT
<213> ORGANISM: Candida dubliniensis

<400> SEQUENCE: 24

Met Ser Leu Asn Pro Ala Leu Lys Phe Arg Asp Phe Ile Gln Val Leu
1               5                   10                  15

Lys Asn Glu Gly Asp Leu Ile Glu Ile Asp Thr Glu Val Asp Pro Asn
            20                  25                  30

Leu Glu Val Gly Ala Ile Thr Arg Lys Ala Tyr Glu Asn Lys Leu Ala
        35                  40                  45

Ala Pro Leu Phe Asn Asn Leu Lys Gln Asp Pro Glu Asn Ile Asp Pro
    50                  55                  60

Lys Asn Leu Phe Arg Ile Leu Gly Cys Pro Gly Gly Leu Arg Gly Phe

-continued

```
                65                  70                  75                  80
Gly Asn Asp His Ala Arg Ile Ala Leu His Leu Gly Leu Asp Ser Gln
                    85                  90                  95
Thr Pro Met Lys Glu Ile Ile Asp Phe Leu Val Ala Asn Arg Asn Pro
                    100                 105                 110
Lys Lys Tyr Ile Pro Pro Val Leu Val Pro Asn Asp Gln Ser Pro His
                    115                 120                 125
Lys Lys His His Leu Thr Lys Glu Gln Ile Asp Leu Thr Lys Leu Pro
                    130                 135                 140
Val Pro Leu Leu His His Gly Asp Gly Gly Lys Phe Ile Gln Thr Tyr
145                 150                 155                 160
Gly Met Trp Val Leu Gln Thr Pro Asp Lys Ser Trp Thr Asn Trp Ser
                    165                 170                 175
Ile Ala Arg Gly Met Val His Asp Ser Lys Ser Ile Thr Gly Leu Val
                    180                 185                 190
Ile Asn Pro Gln His Val Lys Gln Val Ser Asp Ala Trp Val Ala Ala
                    195                 200                 205
Gly Lys Gly Asp Lys Ile Pro Phe Ala Leu Cys Phe Gly Val Pro Pro
                    210                 215                 220
Ala Ala Ile Leu Val Ser Ser Met Pro Ile Pro Asp Gly Ala Thr Glu
225                 230                 235                 240
Ala Glu Tyr Ile Gly Gly Leu Cys Asn Gln Ala Val Pro Val Val Lys
                    245                 250                 255
Cys Glu Thr Asn Asp Leu Glu Val Pro Ala Asp Cys Glu Met Val Phe
                    260                 265                 270
Glu Gly Tyr Leu Asp Arg Asp Thr Leu Val Arg Glu Gly Pro Phe Gly
                    275                 280                 285
Glu Met His Gly Tyr Cys Phe Pro Lys Asp His Thr Gln Pro Leu
                    290                 295                 300
Tyr Arg Val Asn His Ile Ser Tyr Arg Asp Gln Ala Ile Met Pro Ile
305                 310                 315                 320
Ser Asn Pro Gly Leu Cys Thr Asp Glu Thr His Thr Leu Ile Gly Gly
                    325                 330                 335
Leu Val Ser Ala Glu Thr Lys Tyr Leu Ile Ser Gln His Pro Val Leu
                    340                 345                 350
Ser Lys Ile Val Glu Asp Val Phe Thr Pro Tyr Glu Ala Gln Ala Leu
                    355                 360                 365
Trp Leu Ala Val Lys Ile Asn Thr His Glu Leu Val Lys Leu Lys Thr
                    370                 375                 380
Asn Ala Lys Glu Leu Ser Asn Leu Val Gly Asp Phe Leu Phe Arg Ser
385                 390                 395                 400
Lys Glu Cys Tyr Lys Val Cys Ser Ile Leu His Glu Ile Ile Leu Val
                    405                 410                 415
Gly Asp Asp Ile Asp Ile Phe Asp Phe Lys Gln Leu Ile Trp Ala Tyr
                    420                 425                 430
Thr Thr Arg His Thr Pro Val Gln Asp Gln Leu Tyr Phe Asp Asp Val
                    435                 440                 445
Lys Pro Phe Ala Leu Ala Pro Phe Ala Ser Gln Gly Pro Leu Ile Lys
                    450                 455                 460
Thr Arg Gln Gly Gly Lys Cys Val Thr Thr Cys Ile Phe Pro Lys Gln
465                 470                 475                 480
Phe Thr Asp Pro Asp Phe Glu Phe Val Thr Cys Asn Phe Asn Gly Tyr
                    485                 490                 495
```

```
Pro Glu Glu Val Lys Asn Lys Ile Ser Gln Asn Trp Asp Lys Tyr Tyr
            500                 505                 510
Lys
```

<210> SEQ ID NO 25
<211> LENGTH: 513
<212> TYPE: PRT
<213> ORGANISM: Candida albicans

<400> SEQUENCE: 25

```
Met Ser Leu Asn Pro Ala Leu Lys Phe Arg Asp Phe Ile Gln Val Leu
1               5                   10                  15

Lys Asn Glu Gly Asp Leu Val Glu Ile Asp Thr Glu Val Asp Pro Asn
            20                  25                  30

Leu Glu Val Gly Ala Ile Thr Arg Lys Ala Tyr Glu Asn Lys Leu Ala
        35                  40                  45

Ala Pro Leu Phe Asn Asn Leu Lys Gln Asp Pro Gly Asn Val Asp Pro
    50                  55                  60

Lys Asn Leu Phe Arg Ile Leu Gly Cys Pro Gly Gly Leu Arg Gly Phe
65                  70                  75                  80

Gly Asn Asp His Ala Arg Ile Ala Leu His Leu Gly Leu Asp Ser Gln
                85                  90                  95

Thr Pro Met Lys Glu Ile Ile Asp Phe Leu Val Ala Asn Arg Asn Pro
            100                 105                 110

Lys Lys Phe Ile Pro Pro Val Leu Val Pro Asn Glu Lys Ser Pro His
        115                 120                 125

Lys Lys His His Leu Thr His Glu Gln Ile Asp Leu Thr Lys Leu Pro
130                 135                 140

Val Pro Leu Leu His His Gly Asp Gly Lys Phe Ile Gln Thr Tyr
145                 150                 155                 160

Gly Met Trp Val Leu Gln Thr Pro Asp Lys Ser Trp Thr Asn Trp Ser
                165                 170                 175

Ile Ala Arg Gly Met Val His Asp Ser Lys Ser Ile Thr Gly Leu Val
            180                 185                 190

Ile Asn Pro Gln His Val Lys Gln Val Ser Asp Ala Trp Val Ala Ala
        195                 200                 205

Gly Lys Gly Asp Lys Ile Pro Phe Ala Leu Cys Phe Gly Val Pro Pro
    210                 215                 220

Ala Ala Ile Leu Val Ser Ser Met Pro Ile Pro Asp Gly Ala Thr Glu
225                 230                 235                 240

Ala Glu Tyr Ile Gly Gly Leu Cys Asn Gln Ala Val Pro Val Val Lys
                245                 250                 255

Cys Glu Thr Asn Asp Leu Glu Val Pro Ala Asp Cys Glu Met Val Phe
            260                 265                 270

Glu Gly Tyr Leu Asp Arg Asp Thr Leu Val Thr Glu Gly Pro Phe Gly
        275                 280                 285

Glu Met His Gly Tyr Cys Phe Pro Gln Asp His His Thr Gln Pro Leu
    290                 295                 300

Tyr Arg Val Asn His Ile Ser Tyr Arg Asp Glu Ala Ile Met Pro Ile
305                 310                 315                 320

Ser Asn Pro Gly Leu Cys Thr Asp Glu Thr His Thr Leu Ile Gly Gly
                325                 330                 335

Leu Val Ser Ala Glu Thr Lys Tyr Leu Ile Ser Gln His Leu Val Leu
            340                 345                 350
```

```
Ser Lys Ile Val Glu Asp Val Phe Thr Pro Tyr Gln Ala Gln Ala Leu
        355                 360                 365

Trp Leu Ala Val Lys Ile Asn Ile Gln Glu Leu Ile Lys Leu Lys Thr
370                 375                 380

Asn Ala Lys Glu Leu Ser Asn Leu Val Gly Asp Phe Leu Phe Lys Ser
385                 390                 395                 400

Lys Glu Cys Tyr Lys Val Cys Ser Ile Leu His Glu Val Ile Leu Val
                405                 410                 415

Gly Asp Asp Ile Asp Ile Phe Asp Phe Lys Gln Leu Ile Trp Ala Tyr
                420                 425                 430

Thr Thr Arg His Thr Pro Val Gln Asp Gln Val Tyr Phe Asp Asp Val
            435                 440                 445

Lys Pro Phe Pro Leu Ala Pro Phe Ile Ser Gln Gly Pro Leu Ile Lys
        450                 455                 460

Thr Arg Gln Gly Gly Lys Cys Val Thr Ser Cys Ile Phe Pro Lys Gln
465                 470                 475                 480

Phe Thr Asp Pro Asp Phe Lys Phe Val Thr Cys Asn Phe Asn Gly Tyr
                485                 490                 495

Pro Glu Glu Val Lys Asn Lys Val Phe Gln Asn Trp Glu Lys Tyr Tyr
            500                 505                 510

Lys
```

<210> SEQ ID NO 26
<211> LENGTH: 500
<212> TYPE: PRT
<213> ORGANISM: Aspergillus niger

<400> SEQUENCE: 26

```
Met Ser Ala Gln Pro Ala His Leu Cys Phe Arg Ser Phe Val Glu Ala
1               5                   10                  15

Leu Lys Val Asp Asn Asp Leu Val Glu Ile Asn Thr Pro Ile Asp Pro
            20                  25                  30

Asn Leu Glu Ala Ala Ala Ile Thr Arg Arg Val Cys Glu Thr Asn Asp
        35                  40                  45

Lys Ala Pro Leu Phe Asn Asn Leu Ile Gly Met Lys Asn Gly Leu Phe
50                  55                  60

Arg Ile Leu Gly Ala Pro Gly Ser Leu Arg Lys Ser Ser Ala Asp Arg
65                  70                  75                  80

Tyr Gly Arg Leu Ala Arg His Leu Ala Leu Pro Pro Thr Ala Ser Met
                85                  90                  95

Arg Glu Ile Leu Asp Lys Met Leu Ser Ala Ser Asp Met Pro Pro Ile
                100                 105                 110

Pro Pro Thr Ile Val Pro Thr Gly Pro Cys Lys Glu Asn Ser Leu Asp
            115                 120                 125

Asp Ser Glu Phe Asp Leu Thr Glu Leu Pro Val Pro Leu Ile His Lys
        130                 135                 140

Ser Asp Gly Gly Lys Tyr Ile Gln Thr Tyr Gly Met His Ile Val Gln
145                 150                 155                 160

Ser Pro Asp Gly Thr Trp Thr Asn Trp Ser Ile Ala Arg Ala Met Val
                165                 170                 175

His Asp Lys Asn His Leu Thr Gly Leu Val Ile Pro Gln His Ile
                180                 185                 190

Trp Gln Ile His Gln Met Trp Lys Lys Glu Gly Arg Ser Asp Val Pro
            195                 200                 205
```

```
Trp Ala Leu Ala Phe Gly Val Pro Pro Ala Ile Met Ala Ser Ser
    210                 215                 220

Met Pro Ile Pro Asp Gly Val Thr Glu Ala Gly Tyr Val Gly Ala Met
225                 230                 235                 240

Thr Gly Ser Ser Leu Glu Leu Val Lys Cys Asp Thr Asn Asp Leu Tyr
                245                 250                 255

Val Pro Ala Thr Ser Glu Ile Val Leu Glu Gly Thr Leu Ser Ile Ser
            260                 265                 270

Glu Thr Gly Pro Glu Gly Pro Phe Gly Glu Met His Gly Tyr Ile Phe
    275                 280                 285

Pro Gly Asp Thr His Leu Gly Ala Lys Tyr Lys Val Asn Arg Ile Thr
290                 295                 300

Tyr Arg Asn Asn Ala Ile Met Pro Met Ser Ser Cys Gly Arg Leu Thr
305                 310                 315                 320

Asp Glu Thr His Thr Met Ile Gly Ser Leu Ala Ala Ala Glu Ile Arg
                325                 330                 335

Lys Leu Cys Gln Gln Asn Asp Leu Pro Ile Thr Asp Ala Phe Ala Pro
            340                 345                 350

Phe Glu Ser Gln Val Thr Trp Val Ala Leu Arg Val Asp Thr Glu Lys
    355                 360                 365

Leu Arg Ala Met Lys Thr Thr Ser Glu Gly Phe Arg Lys Arg Val Gly
370                 375                 380

Asp Val Val Phe Asn His Lys Ala Gly Tyr Thr Ile His Arg Leu Val
385                 390                 395                 400

Leu Val Gly Asp Asp Ile Asp Val Tyr Glu Gly Lys Asp Val Leu Trp
                405                 410                 415

Ala Phe Ser Thr Arg Cys Arg Pro Gly Met Asp Glu Thr Leu Phe Glu
            420                 425                 430

Asp Val Arg Gly Phe Pro Leu Ile Pro Tyr Met Gly His Gly Asn Gly
    435                 440                 445

Pro Ala His Arg Gly Gly Lys Val Val Ser Asp Ala Leu Met Pro Thr
450                 455                 460

Glu Tyr Thr Thr Gly Arg Asn Trp Glu Ala Ala Asp Phe Asn Gln Ser
465                 470                 475                 480

Tyr Pro Glu Asp Leu Lys Gln Lys Val Leu Asp Asn Trp Thr Lys Met
                485                 490                 495

Gly Phe Ser Asn
            500

<210> SEQ ID NO 27
<211> LENGTH: 242
<212> TYPE: PRT
<213> ORGANISM: Saccharomyces cerevisiae

<400> SEQUENCE: 27

Met Leu Leu Phe Pro Arg Arg Thr Asn Ile Ala Phe Phe Lys Thr Thr
1               5                   10                  15

Gly Ile Phe Ala Asn Phe Pro Leu Leu Gly Arg Thr Ile Thr Thr Ser
            20                  25                  30

Pro Ser Phe Leu Thr His Lys Leu Ser Lys Glu Val Thr Arg Ala Ser
        35                  40                  45

Thr Ser Pro Pro Arg Pro Lys Arg Ile Val Val Ala Ile Thr Gly Ala
    50                  55                  60

Thr Gly Val Ala Leu Gly Ile Arg Leu Leu Gln Leu Leu Lys Glu Leu
```

```
65                  70                  75                  80
Ser Val Glu Thr His Leu Val Ile Ser Lys Trp Gly Ala Ala Thr Met
                85                  90                  95

Lys Tyr Glu Thr Asp Trp Glu Pro His Asp Val Ala Ala Leu Ala Thr
                100                 105                 110

Lys Thr Tyr Ser Val Arg Asp Val Ser Ala Cys Ile Ser Ser Gly Ser
                115                 120                 125

Phe Gln His Asp Gly Met Ile Val Val Pro Cys Ser Met Lys Ser Leu
            130                 135                 140

Ala Ala Ile Arg Ile Gly Phe Thr Glu Asp Leu Ile Thr Arg Ala Ala
145                 150                 155                 160

Asp Val Ser Ile Lys Glu Asn Arg Lys Leu Leu Val Thr Arg Glu
                165                 170                 175

Thr Pro Leu Ser Ser Ile His Leu Glu Asn Met Leu Ser Leu Cys Arg
            180                 185                 190

Ala Gly Val Ile Ile Phe Pro Pro Val Pro Ala Phe Tyr Thr Arg Pro
            195                 200                 205

Lys Ser Leu His Asp Leu Leu Glu Gln Ser Val Gly Arg Ile Leu Asp
            210                 215                 220

Cys Phe Gly Ile His Ala Asp Thr Phe Pro Arg Trp Glu Gly Ile Lys
225                 230                 235                 240

Ser Lys

<210> SEQ ID NO 28
<211> LENGTH: 242
<212> TYPE: PRT
<213> ORGANISM: Saccharomyces cerevisiae

<400> SEQUENCE: 28

Met Leu Leu Phe Pro Arg Arg Thr Asn Ile Ala Phe Phe Lys Thr Thr
1               5                   10                  15

Gly Ile Phe Ala Asn Phe Pro Leu Leu Gly Arg Thr Ile Thr Thr Ser
                20                  25                  30

Pro Ser Phe Leu Thr Tyr Lys Leu Ser Lys Glu Val Thr Arg Val Ser
            35                  40                  45

Thr Ser Pro Pro Arg Pro Lys Arg Ile Val Val Ala Ile Thr Gly Ala
50                  55                  60

Thr Gly Val Ala Leu Gly Ile Arg Leu Leu Gln Val Leu Lys Glu Leu
65                  70                  75                  80

Ser Val Glu Thr His Leu Val Ile Ser Lys Trp Gly Ala Ala Thr Met
                85                  90                  95

Lys Tyr Glu Thr Asp Trp Glu Pro His Asp Val Ala Ala Leu Ala Thr
                100                 105                 110

Lys Thr Tyr Ser Val Arg Asp Val Ser Ala Cys Ile Ser Ser Gly Ser
                115                 120                 125

Phe Gln His Asp Gly Met Ile Val Val Pro Cys Ser Met Lys Ser Leu
            130                 135                 140

Ala Ala Ile Arg Ile Gly Phe Thr Glu Asp Leu Ile Thr Arg Ala Ala
145                 150                 155                 160

Asp Val Ser Ile Lys Glu Asn Arg Lys Leu Leu Val Thr Arg Glu
                165                 170                 175

Thr Pro Leu Ser Ser Ile His Leu Glu Asn Met Leu Ser Leu Cys Arg
            180                 185                 190

Ala Gly Val Ile Ile Phe Pro Pro Val Pro Ala Phe Tyr Thr Arg Pro
```

```
                195                 200                 205
Lys Ser Leu His Asp Leu Leu Glu Gln Ser Val Gly Arg Ile Leu Asp
        210                 215                 220

Cys Phe Gly Ile His Ala Asp Thr Phe Pro Arg Trp Glu Gly Ile Lys
225                 230                 235                 240

Ser Lys

<210> SEQ ID NO 29
<211> LENGTH: 242
<212> TYPE: PRT
<213> ORGANISM: Saccharomyces cerevisiae

<400> SEQUENCE: 29

Met Leu Leu Phe Pro Arg Arg Thr Asn Ile Ala Phe Phe Lys Thr Thr
1               5                   10                  15

Gly Ile Phe Ala Asn Phe Pro Leu Leu Gly Arg Thr Ile Thr Thr Ser
            20                  25                  30

Pro Ser Phe Leu Thr Tyr Lys Leu Ser Lys Glu Val Thr Arg Val Ser
        35                  40                  45

Thr Ser Pro Pro Arg Pro Lys Arg Ile Ile Val Ala Ile Thr Gly Ala
50                  55                  60

Thr Gly Val Ala Leu Gly Ile Arg Leu Leu Gln Val Leu Lys Glu Leu
65                  70                  75                  80

Ser Val Glu Thr His Leu Val Ile Ser Lys Trp Gly Ala Ala Thr Met
                85                  90                  95

Lys Tyr Glu Thr Asp Trp Glu Pro His Asp Val Ala Ala Leu Ala Thr
            100                 105                 110

Lys Thr Tyr Ser Val Arg Asp Val Ser Ala Cys Ile Ser Ser Gly Ser
        115                 120                 125

Phe Gln His Asp Gly Met Ile Val Pro Cys Ser Met Lys Ser Leu
130                 135                 140

Ala Ala Ile Arg Ile Gly Phe Thr Glu Asp Leu Ile Thr Arg Ala Ala
145                 150                 155                 160

Asp Val Ser Ile Lys Glu Asn Arg Lys Leu Leu Leu Val Thr Arg Glu
                165                 170                 175

Thr Pro Leu Ser Ser Ile His Leu Glu Asn Met Leu Ser Leu Cys Arg
            180                 185                 190

Ala Gly Val Ile Ile Phe Pro Pro Val Pro Ala Phe Tyr Thr Arg Pro
        195                 200                 205

Lys Ser Leu His Asp Leu Leu Glu Gln Ser Val Gly Arg Ile Leu Asp
210                 215                 220

Cys Phe Gly Ile His Ala Asp Thr Phe Pro Arg Trp Glu Gly Ile Lys
225                 230                 235                 240

Ser Lys

<210> SEQ ID NO 30
<211> LENGTH: 242
<212> TYPE: PRT
<213> ORGANISM: Saccharomyces cerevisiae

<400> SEQUENCE: 30

Met Leu Leu Phe Pro Arg Arg Thr Asn Ile Ala Phe Phe Lys Thr Thr
1               5                   10                  15

Gly Ile Phe Ala Asn Phe Pro Leu Leu Gly Arg Thr Ile Thr Thr Ser
            20                  25                  30
```

```
Pro Ser Phe Leu Thr Tyr Lys Leu Ser Lys Glu Val Thr Arg Val Ser
            35                  40                  45

Thr Ser Pro Pro Arg Pro Lys Arg Ile Val Val Ala Ile Thr Gly Ala
 50                      55                  60

Thr Gly Val Ala Leu Gly Ile Arg Leu Leu Gln Val Leu Lys Glu Leu
 65                  70                  75                  80

Ser Val Glu Thr His Leu Val Ile Ser Lys Trp Gly Ala Ala Thr Met
                    85                  90                  95

Lys Tyr Glu Thr Asp Trp Glu Pro His Asp Val Ala Ala Leu Ala Thr
                100                 105                 110

Lys Thr Tyr Ser Val Arg Asp Val Ser Ala Cys Ile Ser Ser Gly Ser
                115                 120                 125

Phe Gln His Asp Gly Met Ile Val Val Pro Cys Ser Met Lys Ser Leu
        130                 135                 140

Ala Ala Ile Arg Ile Gly Phe Thr Glu Asp Leu Ile Thr Arg Ala Ala
145                 150                 155                 160

Asp Val Ser Ile Lys Glu Asn Arg Lys Leu Leu Val Thr Arg Glu
                165                 170                 175

Thr Pro Leu Ser Ser Ile His Val Glu Asn Met Leu Ser Leu Cys Arg
                180                 185                 190

Ala Gly Val Ile Ile Phe Pro Pro Val Pro Ala Phe Tyr Thr Arg Pro
            195                 200                 205

Lys Ser Leu His Asp Leu Leu Glu Gln Ser Val Gly Arg Ile Leu Asp
                210                 215                 220

Cys Phe Gly Ile His Ala Asp Thr Phe Pro Arg Trp Glu Gly Ile Lys
225                 230                 235                 240

Ser Lys

<210> SEQ ID NO 31
<211> LENGTH: 242
<212> TYPE: PRT
<213> ORGANISM: Saccharomyces cerevisiae

<400> SEQUENCE: 31

Met Leu Leu Phe Pro Arg Arg Thr Asn Ile Ala Phe Phe Lys Thr Thr
 1               5                  10                  15

Gly Ile Phe Ala Asn Phe Pro Leu Leu Gly Arg Thr Ile Thr Thr Ser
            20                  25                  30

Pro Ser Phe Leu Thr Tyr Lys Leu Ser Lys Glu Val Thr Arg Val Ser
            35                  40                  45

Thr Ser Pro Pro Arg Pro Lys Arg Ile Val Val Ala Ile Thr Gly Ala
 50                      55                  60

Thr Gly Val Ala Leu Gly Ile Arg Leu Leu Gln Val Leu Lys Glu Leu
 65                  70                  75                  80

Ser Val Glu Thr His Leu Val Ile Ser Lys Trp Gly Ala Ala Thr Met
                    85                  90                  95

Lys Tyr Glu Thr Asp Trp Glu Pro His Asp Val Ala Ala Leu Ala Thr
                100                 105                 110

Lys Thr Tyr Ser Val Arg Asp Val Ser Ala Cys Ile Ser Ser Gly Ser
                115                 120                 125

Phe Gln His Asp Gly Met Ile Val Val Pro Cys Ser Met Lys Ser Leu
        130                 135                 140

Ala Ala Ile Arg Ile Gly Phe Thr Glu Asp Leu Ile Thr Arg Ala Ala
145                 150                 155                 160
```

Asp Val Ser Ile Lys Glu Asn Arg Lys Leu Leu Val Thr Arg Glu
            165                 170                 175

Thr Pro Leu Ser Ser Ile His Val Glu Asn Met Leu Ser Leu Cys Arg
        180                 185                 190

Ala Gly Val Ile Ile Phe Pro Pro Val Pro Ala Phe Tyr Thr Arg Pro
        195                 200                 205

Lys Ser Leu His Gly Leu Leu Glu Gln Ser Val Gly Arg Ile Leu Asp
        210                 215                 220

Cys Phe Gly Ile His Ala Asp Thr Phe Pro Arg Trp Glu Gly Ile Lys
225                 230                 235                 240

Ser Lys

<210> SEQ ID NO 32
<211> LENGTH: 242
<212> TYPE: PRT
<213> ORGANISM: Saccharomyces cerevisiae

<400> SEQUENCE: 32

Met Phe Lys Leu Pro Ser Lys Val Asn Leu Ala Ser Phe Lys Gly Lys
1               5                   10                  15

Gly His Leu Ala Lys Phe Pro Leu Arg Ser Arg Ser Ile Ser Asn Ser
            20                  25                  30

Ser Leu Pro Leu Ser Tyr Met Thr Pro Lys Glu Val Ser Asn Val Ser
        35                  40                  45

Ala Ser Pro Pro Arg Pro Lys Arg Ile Val Val Ala Ile Thr Gly Ala
    50                  55                  60

Thr Gly Val Ala Leu Gly Ile Lys Leu Leu Gln Ile Leu Lys Glu Leu
65                  70                  75                  80

Ser Val Glu Thr His Leu Ile Ile Ser Lys Trp Gly Ala Ala Thr Met
                85                  90                  95

Lys Tyr Glu Thr Asp Trp Glu Pro His Asp Val Ala Ala Leu Ala Ser
            100                 105                 110

Lys Thr Tyr Ser Val Arg Asp Val Ser Ala Cys Ile Ser Ser Gly Ser
        115                 120                 125

Phe Gln His Asp Gly Met Ile Val Ala Pro Cys Ser Met Lys Thr Leu
    130                 135                 140

Ala Ala Ile Arg Ile Gly Phe Thr Glu Asp Leu Ile Thr Arg Ala Ala
145                 150                 155                 160

Asp Val Ser Ile Lys Glu Asn Arg Lys Leu Leu Val Thr Arg Glu
            165                 170                 175

Thr Pro Leu Ser Ala Ile His Leu Glu Asn Met Leu Phe Leu Arg Arg
        180                 185                 190

Thr Gly Val Ile Ile Phe Pro Pro Val Pro Ala Tyr Tyr Thr Lys Pro
    195                 200                 205

Lys Ser Met Asn Asp Leu Leu Glu Gln Ser Ala Gly Arg Ile Leu Asp
        210                 215                 220

Cys Phe Gly Ile His Ala Asp Thr Phe Pro Arg Trp Glu Gly Ile Lys
225                 230                 235                 240

Ile Lys

<210> SEQ ID NO 33
<211> LENGTH: 230
<212> TYPE: PRT
<213> ORGANISM: Saccharomyces cerevisiae
<220> FEATURE:
<221> NAME/KEY: misc_feature
<222> LOCATION: (213)..(213)
<223> OTHER INFORMATION: Xaa can be any naturally occurring amino acid

<400> SEQUENCE: 33

```
Met Leu Leu Phe Pro Arg Arg Thr Asn Ile Ala Phe Phe Lys Thr Thr
1               5                   10                  15

Gly Ile Phe Ala Asn Phe Pro Leu Leu Gly Arg Thr Ile Thr Thr Ser
                20                  25                  30

Pro Ser Phe Leu Thr Tyr Lys Leu Ser Lys Glu Val Thr Arg Val Ser
            35                  40                  45

Thr Ser Pro Pro Arg Pro Lys Arg Ile Val Val Ala Ile Thr Gly Ala
    50                  55                  60

Thr Gly Val Ala Leu Gly Ile Arg Leu Leu Gln Val Leu Lys Glu Leu
65                  70                  75                  80

Ser Val Glu Thr His Leu Val Ile Ser Lys Trp Gly Ala Ala Thr Met
                85                  90                  95

Lys Tyr Glu Thr Asp Trp Glu Pro His Asp Val Ala Ala Leu Ala Thr
            100                 105                 110

Lys Thr Tyr Ser Val Arg Asp Val Ser Ala Cys Ile Ser Ser Gly Ser
        115                 120                 125

Phe Gln His Asp Gly Met Ile Val Val Pro Cys Ser Met Lys Ser Leu
130                 135                 140

Ala Ala Ile Arg Ile Gly Phe Thr Glu Asp Leu Ile Thr Arg Ala Ala
145                 150                 155                 160

Asp Val Ser Ile Lys Glu Asn Arg Lys Leu Leu Val Thr Arg Glu
                165                 170                 175

Thr Pro Leu Ser Ser Ile His Val Glu Asn Met Leu Ser Leu Cys Arg
            180                 185                 190

Ala Gly Val Ile Ile Phe Pro Pro Val Pro Ala Phe Leu Tyr Lys Thr
        195                 200                 205

Gln Glu Pro Ser Xaa Pro Ile Arg Thr Lys Cys Trp Gln Asp Pro Arg
210                 215                 220

Leu Leu Trp His Pro Arg
225                 230
```

<210> SEQ ID NO 34
<211> LENGTH: 248
<212> TYPE: PRT
<213> ORGANISM: Debaryomyces hansenii

<400> SEQUENCE: 34

```
Met Lys Ser Ser Ser Met Gly His Arg Ser Ile Arg Ile Ser Asn Tyr
1               5                   10                  15

Met Phe Arg Pro Phe Ser Ile Ser Ser Thr Ile Arg Asn Lys Asn Pro
                20                  25                  30

Ile Ser Asp Tyr Glu Gln Val Ser Asn Asp Ile Tyr Gln Asn Gln Ser
            35                  40                  45

Thr Gly Leu Tyr Leu Thr Arg Pro Lys Arg Ile Val Val Ala Ile Thr
    50                  55                  60

Gly Ala Thr Gly Ile Ala Ile Gly Val Arg Val Leu Glu Leu Leu Lys
65                  70                  75                  80

Gln Cys Lys Val Glu Thr His Leu Ile Met Ser Lys Trp Gly Met Ala
                85                  90                  95

Thr Met Lys Tyr Glu Thr Asp Tyr His Met Asp Asp Ile Met Ala Leu
            100                 105                 110
```

```
Ala Ser Lys Val Tyr Thr Ala Arg Asp Val Ser Ala Pro Ile Ser Ser
            115                 120                 125

Gly Ser Phe Gln His Asp Gly Met Ile Val Val Pro Cys Ser Met Lys
130                 135                 140

Thr Leu Ala Gly Ile Arg Met Gly Phe Thr Glu Asp Leu Ile Val Arg
145                 150                 155                 160

Ala Ala Asp Val Thr Leu Lys Glu Arg Arg Lys Leu Leu Leu Val Thr
                165                 170                 175

Arg Glu Thr Pro Leu Ser Asp Ile His Leu Asp Asn Met Leu Tyr Leu
            180                 185                 190

Ser Arg Met Gly Thr Ile Ile Phe Pro Pro Val Pro Ala Phe Tyr Thr
            195                 200                 205

Lys Pro Arg Thr Val Glu Asp Ile Ile Glu Gln Ser Ser Gly Arg Val
210                 215                 220

Leu Asp Cys Phe Gly Ile Asp Thr Asn Thr Phe Pro Arg Trp Glu Gly
225                 230                 235                 240

Val Lys Asp Thr Lys Thr Leu Lys
                245

<210> SEQ ID NO 35
<211> LENGTH: 247
<212> TYPE: PRT
<213> ORGANISM: Zygosaccharomyces rouxii

<400> SEQUENCE: 35

Met Leu Gly Met Gln Phe Phe Ser Arg Ala Leu Cys Val Gly Gly His
1               5                   10                  15

Val Arg Ser Phe Cys Phe Ser Gln Val Arg Gly Pro Val Lys Leu Arg
            20                  25                  30

Ser Phe Gly Thr Asn Leu Ala Lys Arg Asn Ser Ser Ser Ser Ser Leu
        35                  40                  45

Thr Glu Lys Gln Val Cys Asn Gly Thr Val Ala Pro Lys Pro Lys Arg
50                  55                  60

Ile Val Val Ser Ile Thr Gly Ala Thr Gly Ile Ala Leu Gly Val Arg
65                  70                  75                  80

Ile Leu Gln Ile Leu Lys Glu Leu Asn Val Glu Thr His Leu Ile Ile
                85                  90                  95

Ser Lys Trp Gly Met Ala Thr Met Lys Tyr Glu Thr Asp Phe Thr Leu
            100                 105                 110

Glu Asp Leu Arg Ser Ile Ala Thr His Thr Tyr Pro Ala Lys Asn Val
            115                 120                 125

Ala Ala Ala Val Ser Ser Gly Ser Phe Leu His Asp Gly Met Ile Val
130                 135                 140

Val Pro Cys Ser Met Lys Thr Leu Ala Ala Ile Arg Cys Gly Tyr Thr
145                 150                 155                 160

Glu Asp Leu Ile Val Arg Ala Ala Asp Val Thr Leu Lys Glu Lys Arg
                165                 170                 175

Lys Leu Leu Val Val Pro Arg Glu Thr Pro Leu Ser Glu Ile His Leu
            180                 185                 190

Glu Asn Met Leu Ser Leu Ala Arg Met Gly Val Ile Ile Phe Pro Pro
            195                 200                 205

Val Pro Ala Phe Tyr Thr Lys Pro Thr Ser Leu Asp Asp Ile Ile Glu
210                 215                 220

Gln Ser Cys Gly Arg Ile Leu Asp Cys Phe Gly Ile His Thr Asn Asn
225                 230                 235                 240
```

-continued

```
Phe Ser Arg Trp Asp Gly Phe
                245

<210> SEQ ID NO 36
<211> LENGTH: 229
<212> TYPE: PRT
<213> ORGANISM: Candida dubliniensis

<400> SEQUENCE: 36

Met Ile Ala Arg Val Cys Leu Lys Arg Pro Asn Ala Leu Pro Ile Phe
1               5                   10                  15

Ser Ile Ser Ser Arg Lys Tyr Ser Ile Asp Tyr Glu Lys Val Asn Asn
            20                  25                  30

Ser Val Tyr Asn Asn Val Ile Ile Pro Lys Arg Ile Val Leu Ala Ile
        35                  40                  45

Thr Gly Ala Thr Gly Thr Gln Ile Gly Val Arg Leu Leu Glu Ile Leu
    50                  55                  60

Lys Glu Leu Gly Val Glu Thr His Leu Val Met Ser Trp Gly Ile
65                  70                  75                  80

Ala Thr Leu Lys Tyr Glu Thr Asp Tyr Gln Val Asp Tyr Val Thr Ser
                85                  90                  95

Leu Ala Thr Lys Thr Tyr Ser Ala Arg Asp Val Thr Ala Pro Ile Ser
            100                 105                 110

Ser Gly Ser Phe Val His Asp Gly Met Ile Val Ala Pro Cys Ser Met
        115                 120                 125

Lys Ser Leu Ser Ala Ile Arg Thr Gly Phe Thr Glu Asp Leu Ile Val
    130                 135                 140

Arg Ala Ala Asp Val Ser Leu Lys Glu Arg Arg Lys Leu Leu Leu Val
145                 150                 155                 160

Ala Arg Glu Thr Pro Leu Ser Asp Ile His Leu Asp Asn Met Leu Tyr
                165                 170                 175

Leu Ser Arg Met Gly Val Ile Ile Phe Pro Pro Val Pro Ala Phe Tyr
            180                 185                 190

Thr Lys Pro Lys Thr Val Asp Asp Ile Ile Glu Gln Thr Cys Gly Arg
        195                 200                 205

Ile Leu Asp Asn Phe Gly Ile Asn Ile Asp Thr Phe Glu Arg Trp Asp
    210                 215                 220

Gly Ile Asn His Lys
225

<210> SEQ ID NO 37
<211> LENGTH: 229
<212> TYPE: PRT
<213> ORGANISM: Candida albicans

<400> SEQUENCE: 37

Met Ile Ala Arg Asp Cys Leu Arg Arg Gln Asn Val Leu Pro Ile Phe
1               5                   10                  15

Gln Ile Pro Ser Arg Lys Tyr Ser Ile Asn Tyr Glu Lys Val Asn Asn
            20                  25                  30

Ser Ile Tyr Asn Asn Val Ile Lys Pro Lys Arg Ile Val Leu Ala Ile
        35                  40                  45

Thr Gly Ala Thr Gly Thr Gln Ile Gly Val Arg Leu Leu Glu Ile Leu
    50                  55                  60

Lys Glu Leu Gly Val Glu Thr His Leu Val Met Ser Trp Gly Ile
65                  70                  75                  80
```

```
Ala Thr Leu Lys Tyr Glu Thr Asp Tyr Gln Val Asp Tyr Val Thr Ser
                85                  90                  95
Leu Ala Thr Lys Thr Tyr Ser Ala Arg Asp Val Thr Ala Pro Ile Ser
            100                 105                 110
Ser Gly Ser Phe Val His Asp Gly Met Ile Val Ala Pro Cys Ser Met
        115                 120                 125
Lys Ser Leu Ser Ala Ile Arg Thr Gly Phe Thr Glu Asp Leu Ile Val
    130                 135                 140
Arg Ala Ala Asp Val Ser Leu Lys Glu Arg Arg Lys Leu Leu Leu Val
145                 150                 155                 160
Ala Arg Glu Thr Pro Leu Ser Asp Ile His Leu Asp Asn Met Leu Tyr
                165                 170                 175
Leu Ser Arg Met Gly Val Thr Ile Phe Pro Pro Val Pro Ala Phe Tyr
            180                 185                 190
Thr Lys Pro Lys Thr Ile Asp Asp Ile Val Glu Gln Thr Cys Gly Arg
        195                 200                 205
Ile Leu Asp Asn Phe Gly Ile Asn Ile Asp Thr Phe Glu Arg Trp Asp
    210                 215                 220
Gly Ile Asn His Arg
225

<210> SEQ ID NO 38
<211> LENGTH: 1512
<212> TYPE: DNA
<213> ORGANISM: Saccharomyces cerevisiae

<400> SEQUENCE: 38
atgaggaagc taaatccagc tttagaattt agagactttta tccaggtctt aaaagatgaa      60
gatgacttaa tcgaaattac cgaagagatt gatccaaatc tcgaagtagg tgcaattatg     120
aggaaggcct atgaatccca cttaccagcc ccgttattta aaaatctcaa aggtgcttcg     180
aaggatcttt tcagcatttt aggttgccca gccggtttaa gaagtaagga gaaaggagat     240
catggtagaa ttgcccatca tctgggggctc gacccaaaaa caactatcaa ggaaatcata     300
gattatttgc tggagtgtaa ggagaaggaa cctctccctc caatcactgt tcctgtgtca     360
tctgcacctt gtaaaacaca tatactttct gaagaaaaaa tacatctaca aagcctgcca     420
acaccatatc tacatgtttc agacggtggc aagtacttac aaacgtacgg aatgtggatt     480
cttcaaactc cagataaaaa atggactaat tggtcaattg ctagaggtat ggttgtagat     540
gacaagcata tcactggtct ggtaattaaa ccacaacata ttagacaaat tgctgactct     600
tgggcagcaa ttggaaaagc aaatgaaatt cctttcgcgt tatgttttgg cgttccccca     660
gcagctattt taattagttc catgccaatt cctgaaggtg tttctgaatc ggattatgtt     720
ggcgcaatct gggtgagtc ggttccagta gtaaaatgtg agaccaacga tttaatggtt     780
cctgcaacga gtgagatggt atttgagggt actttgtcct taacagatac acatctggaa     840
ggcccatttg gtgagatgca tggatatgtt ttcaaaagcc aaggtcatcc ttgtccattg     900
tacactgtca aggctatgag ttacagagac aatgctattc tacctgtttc gaaccccggt     960
ctttgtacgg atgagacaca taccttgatt ggttcactag tggctactga ggccaaggag    1020
ctggctattg aatctggctt gccaattctg gatgccttta tgccttatga ggctcaggct    1080
ctttggctta tcttaaaggt ggatttgaaa gggctgcaag cattgaagac aacgcctgaa    1140
gaatttgtaa gaaggtagg tgatatttac tttaggacaa aagttggttt tatagtccat    1200
```

```
gaaataattt tggtggcaga tgatatcgac atatttaact tcaaagaagt catctgggcc      1260
tacgttacaa gacatacacc tgttgcagat cagatggctt ttgatgatgt cacttctttt      1320
cctttggctc cctttgtttc gcagtcatcc agaagtaaga ctatgaaagg tggaaagtgc      1380
gttactaatt gcatatttag acagcaatat gagcgcagtt ttgactacat aacttgtaat      1440
tttgaaaagg gatatccaaa aggattagtt gacaaagtaa atgaaaattg gaaaagatac      1500
ggatataaat aa                                                         1512

<210> SEQ ID NO 39
<211> LENGTH: 1512
<212> TYPE: DNA
<213> ORGANISM: Saccharomyces cerevisiae

<400> SEQUENCE: 39
atgaggaagc taaatccagc tttagaattt agagacttta tccaggtctt aaaagatgaa       60
gatgacttaa tcgaaattac cgaagagatt gatccaaatc tcgaagtagg tgcaattatg      120
aggaaggcct atgaatccca cttaccagcc ccgttattta aaaatctcaa aggtgcttcg      180
aaggatcttt tcagcatttt aggttgccca gccggtttaa gaagtaagga aaaggagat       240 catggtagaa ttgcccatca tctggggctc gacccaaaaa caactatcaa ggaaatcata      300
gattatttgc tggagtgtaa ggagaaggaa cctctcccyc aatcactgt tcctgtgtca       360 tctgcacctt gtaaaacaca tatactttct gaagaaaaaa tacatctaca aagcctgcca      420
acaccatatc tacatgtttc agacggtggc aagtacttac aaacgtacgg aatgtggatt      480
cttcaaactc cagataaaaa atggactaat tggtcaattg ctagaggtat ggttgtagat      540
gacaagcata tcactggtct ggtaattaaa ccacaacata ttagacaaat tgctgactct      600
tgggcagcaa ttggaaaagc aaatgaaatt cccttcgcgt tatgtttggg cgttccccca      660
gcagctattt tagttagttc catgccaatt cctgaaggtg tttctgaatc ggattatgtt      720
ggcgcaatct gggtgagtc ggttccagta gtaaaatgtg agaccaacga tttaatggtt      780
cctgcaacga gtgagatggt atttgagggt actttgtcct taacagatrc acatctggaa      840 ggcccattg gtgagatgca tggatatgtt ttcaaaagcc aaggtcatcc ttgtccattg      900
tacactgtca aggctatgag ttacagagac aatgctattc tacctgtttc gaaccccggt      960
ctttgtacgg atgagacaca taccttgatt ggttcactag tggctactga ggccaaggag     1020
ctggctattg aatctggctt gccaattctg gatgccttta tgccttatga ggctcaggct     1080
ctttggctta tyttaaaggt ggatttgaaa gggctgcaag cattgaagac aacgcctgaa     1140
gaattttgta agaaggtagg tgatatttac tttaggacaa agttggtttt tatagtccat     1200
gaaataattt tggtggcaga tgatatcgac atatttaact tcaaagaagt catctgggcc     1260
tacgttacaa gacatacacc tgttgcagat cagatggctt ttgatgatgt cacttctttt     1320
cctttggctc cctttgtttc gcagtcatcc agaagtaaga ctatgaaagg tggaaagtgc     1380
gttactaatt gcatatttag acagcaatat gagcgcagtt ttgactacat aacttgtaat     1440
tttgaaaagg gatatccaaa aggattagtt gacaaagtaa atgaaaattg gaaaaggtac     1500
ggatataaat aa                                                        1512

<210> SEQ ID NO 40
<211> LENGTH: 1512
<212> TYPE: DNA
<213> ORGANISM: Saccharomyces cerevisiae

<400> SEQUENCE: 40
```

```
atgaggaagc taaatccagc tttagaattt agagacttta tccaggtctt aaaagatgaa      60
gatgacttaa tcgaaattac cgaagagatt gatccaaatc tcgaagtagg tgcaattatg     120
aggaaggcct atgaatccca cttaccagcc ccgttattta aaaatctcaa aggtgcttcg     180
aaggatcttt tcagcatttt aggttgccca gccggtttaa gaagtaagga gaaggagat      240
catggtagaa ttgcccatca tctggggctc gacccaaaaa caactatcaa ggaaatcata     300
gattatttgc tggagtgtaa ggagaaggaa cctctccccc aatcactgt tcctgtgtca      360
tctgcacctt gtaaaacaca tatactttct gaagaaaaaa tacatctaca aagcctgcca     420
acaccatatc tacatgtttc agacggtggc aagtacttac aaacgtacgg aatgtggatt     480
cttcaaactc cagataaaaa atggactaat tggtcaattg ctagaggtat ggttgtagat     540
gacaagcata tcactggtct ggtaattaaa ccacaacata ttagacaaat tgctgactct     600
tgggcagcaa ttggaaaagc aaatgaaatt cctttcgcgt tatgttttgg cgttccccca     660
gcagctattt tagttagttc catgccaatt cctgaaggtg tttctgaatc ggattatgtt     720
ggcgcaatct tgggtgagtc ggttccagta gtaaaatgtg agaccaacga tttaatggtt     780
cctgcaacga gtgagatggt atttgagggt actttgtcct taacagatac acatctggaa     840
ggcccatttg gtgagatgca tggatatgtt ttcaaaagcc aaggtcatgc ttgtccattg     900
tacactgtca aggctatgag ttacagagac aatgctattt tacctgtttc gaaccccggt     960
ctttgtacgg atgagacaca taccttgatt ggttcactag tggctactga ggccaaggag    1020
ctggctattg aatctggctt gccaattctg gatgccttta tgccttatga ggctcaggct    1080
ctttggctta tcttaaaggt ggatttgaaa gggctgcaag cattgaagac aacgcctgaa    1140
gaatttgta agaaggtagg tgatatttac tttaggacaa agttggttt tatagtccat     1200
gaaataattt tggtggcaga tgatatcgac atatttaact tcaaagaagt catctgggcc    1260
tatgttacaa gacatacacc tgttgcagat cagatggctt ttgatgatgt cacttctttt    1320
cctttggctc cctttgtttc gcagtcatcc agaagtaaga ctatgaaagg tggaaagtgc    1380
gttactaatt gcatatttag acagcaatat gagcgcagtt ttgactacat aacttgtaat    1440
tttgaaaagg gatatccaaa aggattagtt gacaaagtaa atgaaaattg gaaaaggtac    1500
ggatataaat aa                                                        1512
```

<210> SEQ ID NO 41  
<211> LENGTH: 1512  
<212> TYPE: DNA  
<213> ORGANISM: Saccharomyces cerevisiae

<400> SEQUENCE: 41

```
atgaggaagc taaatccagc tttagaattt agagacttta tccaggtctt aaaagatgaa      60
gatgacttaa tcgaaattac cgaagagatt gatccaaatc tcgaagtagg tgcaattatg     120
aggaaggcct atgaatccca cttaccagcc ccgttattta aaaatctcaa aggtgcttcg     180
aaggatcttt tcagcatttt aggttgccca gccggtttaa gaagtaagga gaaggagat      240
catggtagaa ttgcccatca tctggggctc gacccaaaaa caactatcaa ggaaatcata     300
gattatttgc tggagtgtaa ggagaaggaa cctctccctc aatcactgt tcctgtgtca      360
tctgcacctt gtaaaacaca tatactttct gaagaaaaaa tacayctaca aagcctgcca     420
acaccatatc tacatgtttc agacggtggc aagtacttac aaacgtacgg aatgtggatt     480
cttcaaactc cagataaaaa atggactaat tggtcaattg ctagaggtat ggttgtagat     540
```

```
gacaagcata tcactggtct ggtaattaaa ccacaacata ttagacaaat tgctgactct    600
tgggcagcaa ttggaaaagc aaatgaaatt ccyttcgcgt tatgttttgg cgttccccca    660
gcagctattt tagttagttc catgccaatt cctgaaggtg tttctgaatc ggattatgtt    720
ggcgcaatct tgggtgagtc ggttccagta gtaaaatgtg agaccaacga tttaatggtt    780
cctgcaacga gtgagatggt atttgagggt actttgtcct aacagatac acatctggaa     840 ggcccatttg gtgagatgca tggatatgtt ttcaamagcc aaggtcatcc ttgtccattg    900
tacactgtca aggctatgag ttacagagac aatgctattc tacctgtttc gaaccccggt    960
ctttgtacgg atgagacaca taccttgatt ggttcactag tggctactga ggccaaggag   1020
ctggctattg aatctggctt gccaattctg gatgcctta tgccttatga ggctcaggct    1080
ctttggctta tcttaaaggt ggatttgaaa gggctgcaag cattgaagac aacgcctgaa   1140
gaattttgta agaaggtagg tgatatttac tttaggacaa aagttggttt tatagtccat   1200
gaaataattt tggtggcaga tgatatcgac atatttaact tcaaagaagt catctgggcc   1260
tacgttacaa gacatacacc tgttgcagat cagatggctt ttgatgatgt cacttctttt   1320
cctttggctc cctttgtttc gcagtcatcc agaagtaaga ctatgaaagg tggaaagtgc   1380
gttactaatt gcatatttag acagcaatat gagcgcagtt ttgactacat aacttgtaat   1440
tttgaaaagg gatatccaaa aggattagtt gacaaagtaa atgaaaattg gaaaaggtac   1500
ggatataaat aa                                                       1512

<210> SEQ ID NO 42
<211> LENGTH: 1512
<212> TYPE: DNA
<213> ORGANISM: Saccharomyces cerevisiae

<400> SEQUENCE: 42
atgagtgcgc taaatccagc actacagttc agagacttca tccaggttct caaagatgaa     60
gatgacttaa ttgaaattac caaagaagtt gatccaaatc tagaggtagg tgcaattatg    120
agaaaagcat atgaatccaa attgccagct ccattattca aaaatatcaa aggcgcttca    180
aaagatcttt tcaatatttt aggttgtcca gccggtttga aaacaaaaa gaaaggtgat     240 catggtagaa ttgctcatca tctcggactc gacccaaaga cgacgatcaa ggaaatcatc    300
gactatttgc tggaatgtaa gaataagaaa ccgttgcccc catctagcat ctctgcttct    360
tccgctcctt gcaaggcaca tgtcctctct gaagaagaaa tacatctgga gagtttgcca    420
acgccatatc tacatacttc cgacggtgga aactacttgc aaacgtacgg aatgtggatt    480
cttcaaactc cagataaaaa atggactaac tggtcaattg ctaggggtat ggtcgtcgat    540
gacaagcata ttacaggttt agtaataaaa ccacagcaca ttagacaaat tgcgacgcc     600 tgggggcaa ttggcaaagg aaataagatt cctttcgcac tgtgttttgg tgttcccct     660 gcagctattc tagtcagttc catgccaatt cctgaaggtg tgtccgaatc ggattatgtc    720
ggtgcaattt tgggcaagcc agtgccagta gtaaaatgcg aaactaacga tttaatggtt    780
cctgcaacta gtgaaattgt ttttgagggc actttatcct aacagacac ccatgcagaa     840 ggtccattcg gtgaaatgca tggatatgtt tttggaggtc aaggtcatcc atgcccttg     900 tatactgtca aggcaatgac tcacagagac aacgctattc tacctgtatc aaatccaggc    960
ctttgtacag acgaaacaca cacattaatt ggttcactgg tggctactga agctaaggag   1020
cttgcaatta aatctggtct accagttctc gatgctttca cgccatatga agctcaagct   1080
ctatggcttg tcttgaaggt ggacttgaaa cggctgcaag cactgaaaac tacccccgag   1140
```

```
gaattctcta agaaggttgg tgacatctac tttagaacga aagttggttt tatcattcat    1200
gagattgttt tggtcgcaga tgacatcgac atatttaact tcaaagaagt tttttgggcc    1260
tatgtcacga gacacactcc agttgctgac cagactgctt ttgacgatgt gacttccttt    1320
cctttggctc cctttgtttc acagtcacct agaagcaaga ctatgaaagg tggaaagtgt    1380
gttaccaatt gcatcttcag acagcaatat gaacgcgatt ttgattacgt tacttgcagc    1440
tttgaaaagg gatattcgaa ggagttggtc gatagaataa atgaaaattg gagggagtat    1500
ggctacaaat aa                                                        1512

<210> SEQ ID NO 43
<211> LENGTH: 1041
<212> TYPE: DNA
<213> ORGANISM: Saccharomyces cerevisiae

<400> SEQUENCE: 43
atgtggattc ttcaaactcc agataaaaaa tggactaatt ggtcaattgc tagaggtatg      60
gttgtagatg acaagcatat cactggtctg gtaattaaac cacaacatat tagacaaatt     120
gctgactctt gggcagcaat tggaaaagca aatgaaattc ctttcgcgtt atgttttggc     180
gttcccccag cagctatttt agttagttcc atgccaattc ctgaaggtgt ttctgaatcg     240
gattatgttg gcgcaatctt gggtgagtcg gttccagtag taaatgtgaa gaccaacgat     300
ttaatggttc ctgcaacgag tgagatggta tttgagggta cttttgtcctt aacagataca    360 catctggaag gcccatttgg tgagatgcat ggatatgttt tcaaaagcca aggtcatcct     420
tgtccattgt acactgtcaa ggctatgagt tacagagaca atgctattct acctgtttcg     480
aaccccggtc tttgtacgga tgagacacat accttgattg gttcactagt ggctactgag     540
gccaaggagc tggctattga atctggcttg ccaattctgg atgcctttat gccttatgag     600
gctcaggctc tttggcttat cttaaaggtg gatttgaaag gctgcaagc attgaagaca       660 acgcctgaag aattttgtaa gaaggtaggt gatatttact ttaggacaaa agttggtttt     720
atagtccatg aaataatttt ggtggcagat gatatcgaca tatttaactt caaagaagtc     780
atctgggcct acgttacaag acatacacct gttgcagatc agatggcttt tgatgatgtc     840
acttcttttc ctttggctcc ctttgtttcg cagtcatcca gaagtaagac tatgaaaggt     900
ggaaagtgcg ttactaactg catatttaga cagcaatatg agcgcagttt tgactacata     960
acttgtaatt tgaaaagggg atatccaaaa ggattagttg acaaagtaaa tgataattgg    1020
aaaaggtacg gatataaata a                                             1041

<210> SEQ ID NO 44
<211> LENGTH: 1542
<212> TYPE: DNA
<213> ORGANISM: Debaryomyces hansenii

<400> SEQUENCE: 44
atgagcaatt taagaccaga gttaagattt agagatttcc ttcaggttct caaaaatgag      60
aatgatttag tagagattac ccacgagtgc gatccaaact tagaggtggg tgctattatg     120
agaaaggtct acgaagaaaa attgccagta cctttattca aaaacttgaa gaaggatcct     180
aaaaatccag accctagtaa tttgttcaat attgtcggct gtcttggtgg tttaagagat     240
gcaaaaaaag acaatgatca tgctagaatt gctcttcatt tggggttgga ttcacaaact     300
cctatgacga agattattga ctacttgata gaagccaata ccaagaagcc acttccacca    360
```

```
gtcttgcttg aagatgcatc gggagcacca tgcaaaaaaa acaagatttc tggagatgtt    420
attaggttga acgcattacc tgcacctacg ttgcatcatg gggatggtgg aagtatatt     480 cagacttacg gaatgtttgt gttacaaaca gcagacaaga cctggacaaa ttggtcaatt    540
gccagaggaa tgatttatga tgataagcat ttaactggtt tggttatgaa tccgcagcat    600
attagaaggg ttgcagacac atgggctgaa attggtatgg gtgatagcgt cccatttgca    660
ttatgtttcg gtgtaccacc agcatcaatt ttagtgagtt ctatgcctat tccagatggt    720
gctacagaag ctgactatat tggtgcttta gtcggtgaac ctttaagtgt tgttaagtgt    780
gagaccaatg atttacacgt tcctgccgat tctgaaatgg ttttcgaagg taccttgaat    840
ttgaataaga tggttgaaga aggtccattt ggtgaaatgc atggttactg tttccctgga    900
catggtcacc cttgtccatt atatactgtt gatactataa cgtacagaga tgatgctata    960
ttaccagttt caaacccagg tttatgtact gatgagacac atacattaat cggtggatta   1020
gtcagtgccg aatgcaagca aatggcctta gaacatccaa aattaaaaag tgttattatg   1080
gaagcattta ctccacatga gggtgtggcc ttatggctcg ctcttaaagt gaataccaaa   1140
gaactcgcta aattgaatac taatagtgaa gatttctgta aacttattgg tgactattat   1200
tatagttcaa aacctggctt catacttcaa gaaattgtct tagttggaga tgatgtcgat   1260
attttcgact tcagaaaatt attttgggct tatgctacga gacatacgcc aggtgatgac   1320
caatatatgt tcaatgacta ccgtgctttc ccattggcgc cattcatcgg ccaaggacca   1380
agaattaaaa ccttaagggg cggaaattgt gttacagact gcttgtttcc taaacagtac   1440
gaacctgaag tgttgatttt cgttacttgt gattttgacg gctatgatga agccataaag   1500
gaaaaggtaa gaaaaaactg gtctgcgtac ggatataaat ag                      1542

<210> SEQ ID NO 45
<211> LENGTH: 1536
<212> TYPE: DNA
<213> ORGANISM: Zygosaccharomyces rouxii

<400> SEQUENCE: 45
atggcaccaa aactaacacc agtcctaaaa ttcagagatt ttttggaagc tttgagaaga     60 gaagggatc tagtcgaaat tttccaggaa gttgatcctc atcttgaagt gggggctatt    120
atgaggaaaa tttatgaaaa caaacttcca gtcccattgt ttaaaaattt gaagcaacca    180
aagggaaatg ttgatcctga taacttattc gatattgccg gttgcattgg tggcttaaga    240
gcatttggta tgatcatgc taggattgct caccacctcg gactgagcag cgacaccggt    300
atgaaggaaa ttatagatca tttgttagaa gcaaagaaaa gaaagcctat cccaccagtt    360
aaagtcaata gagactctgc accttgtaag gagaatattt tgaaaggtga tcaaatcaat    420
ttagagcagt tacctgcgcc ctacctacat gatgaggatg gtggaaagta tcttcaaaca    480
tatgggatgt ttgtattaca gactcccgat aaaagctgga ccaactggtc tattgcgagg    540
gcaatgatcc atgacgaaaa acatttgaca ggattagtta tgaatcctca acacattaga    600
cgtgtagctg atcagtggaa aaccgtcggg aaggaaaacg ctgtgccatt tgcactgtgt    660
tttggtgttc ctccagcttc tatccttggtc agttcaatgc ctattccaga aggagtctct    720
gaagcagatt atattggttc tgttgtaggc gaacccattc aagtagtcca agcagagact    780
aatcaacttg aagttcctgc agaatctgaa atagtgctag aggggacttt gaatttagat    840
catatggtcc cggagggccc ctttggagag atgcatgggt atgtgttccc tggtacaggc    900
catccttgtc caacttatac tgtagagaca atttcatatc ggaataatgc aatttttgcct    960
```

```
gtttctaatc cagggctctg tactgatgaa actcatacgc taattgggtc tttagttgca   1020
gcagaagcta agcaaatttg tctgaaccat cctgtccttt caaaaatagt catggatgca   1080
tttatgccat atgagtctca agtgctttgg ttagcattca aaatcaatgt caagaacttt   1140
gtaaaattga atactgacag caagtcccta gctgactttat ttgcaaagga atatatggc   1200
```

```
gtttctaatc cagggctctg tactgatgaa actcatacgc taattgggtc tttagttgca   1020
gcagaagcta agcaaatttg tctgaaccat cctgtccttt caaaaatagt catggatgca   1080
tttatgccat atgagtctca agtgctttgg ttagcattca aaatcaatgt caagaacttt   1140
gtaaaattga atactgacag caagtcccta gctgacttat ttgcaaagga atatatggc    1200
aacaaagtcg gaatgaccac tcaagagata attttagtcg gtgatgatat tgacattttt   1260
aattttaaaa aattaatgtg gcatatgtg  accaggcata ctcctggaga tgatcaatat   1320
ttctatgacg aattcgttgc tttccctcta gcacctttca tcagtcaggg ccctagaatt   1380
aaaacaaaaa ggggtgggaa ttgtgttacc gactgtcttt tccctattca gtacagggat   1440
ccaaatttcc gatttgtcac ctgtgacttt gattcctacg atagtgccat tcgtgataaa   1500
atcaatcaaa actggtccaa ttatggctat cagtag                             1536

<210> SEQ ID NO 46
<211> LENGTH: 1542
<212> TYPE: DNA
<213> ORGANISM: Candida dubliniensis

<400> SEQUENCE: 46
atgtcactta atccagcatt aaaatttcga gattttattc aagttcttaa gaatgaaggg    60
gatttaattg aaattgatac tgaagttgat cccaatttag aagttggagc cataactaga   120
aaagcttatg agaataaact tgctgctcca cttttcaata atttaaagca agatccagag   180
aatatcgacc ctaagaattt atttcgtata ttaggttgtc ctggtggatt aagaggattt   240
ggtaacgatc atgctcgtat tgccttacat ttaggattag attctcaaac acccatgaaa   300
gaaatcattg attttttggt agcaaataga aatcccaaaa agtatatccc accggttctt   360
gttcctaacg atcaatcacc acataaaaaa catcatttga ctaaggaaca aattgattta   420
acaaaattac cagttccctt attacatcac ggtgatggtg ggaaattcat ccaaacgtat   480
ggtatgtggg tgttacaaac ccccgataaa tcatggacta ttggtcaat  tgctcgaggc   540
atggttcatg attcaaaaag tattactggg ttagttatta tcctcaaca  tgtgaaacaa   600
gtttctgatg catgggttgc tgctggaaaa ggtgataaaa tcccatttgc tctttgtttt   660
ggggttccac cagcagcaat tcttgtttcc tcaatgccaa ttccagatgg agcaactgaa   720
gcagagtaca ttggtggatt gtgcaaccaa gctgttcctg ttgttaaatg tgaaaccaac   780
gatttagaag tcccagcaga ttgtgaaatg gtatttgaag ttatttggga tagagacact   840
ttggttaggg aaggaccatt tggggaaatg catggttatt gttttccaaa agatcatcac   900
acccaaacctt tataccgtgt caaccacata tcatatcgtg accaagctat tatgccaata   960
tcaaaccctg ggtatgtac  tgacgagact catactttga ttggaggatt agtctctgcc   1020
gagacaaagt atttaatttc tcaacaccca gtgttatcta aaatcgtgga agatgtattc   1080
actccctatg aagcgcaagc attatggctt gccgtgaaaa tcaacactca cgaattggtt   1140
aagttaaaaa ctaatgcaaa agaattactg aatttagtgg gtgatttctt atttagatcc   1200
aaagaatgct ataaagtttg tctgattctt catgaaatca ttcttgttgg tgatgatatt   1260
gatattttg  actttaaaca actcatttgg gcatacacca cccgtcatac accagttcaa   1320
gatcagctat actttgatga tgttaaacct ttcgcattgg caccatttgc gtcacaaggt   1380
ccattgatca agactcgtca aggtggtaaa tgtgtaacca cctgtatttt ccctaaacaa   1440
tttactgatc cagactttga gtttgtcact tgtaacttta tgggtatcc  agaagaagtg   1500
```
aaaaataaaa tatctcaaaa ttgggataaa tactacaaat ga          1542

<210> SEQ ID NO 47
<211> LENGTH: 1542
<212> TYPE: DNA
<213> ORGANISM: Candida albicans

<400> SEQUENCE: 47
atgtcactta atccagcatt aaaatttaga gattttattc aagttcttaa aaatgaaggg    60
gatttagttg aaattgatac cgaagttgat cccaatttag aagttggtgc catcacaaga   120
aaagcttatg agaataaact tgctgctcca cttttcaata atttgaaaca agatccagga   180
aatgtcgacc ctaagaactt atttcgtata ttaggttgtc ctggtggatt aagagggttt   240
ggtaatgatc atgctcgtat tgcattacat ttaggattgg attcccaaac accaatgaaa   300
gaaatcattg atttcttagt ggcaaataga accccaaaa aatttatccc accagtactt    360
gttcctaatg aaaatcgcc acataaaaag caccatttga ctcatgaaca aattgattta    420
acaaaattgc cagttccatt attacatcat ggtgatggtg gaaatttat tcaaacttat    480
ggtatgtggg tgttacaaac cccagataaa tcatggacta attggtcaat tgctaggggt   540
atggttcatg attcaaaaag tattacgggg ctagttatta atcctcaaca cgtgaaacaa   600
gtttctgatg catgggttgc agctgggaag ggggataaaa tcccatttgc tctttgtttt   660
ggagtcccgc cggcagcgat tcttgtttca tcgatgccaa ttcctgatgg tgcaactgaa   720
gcagagtata ttggtgggtt atgcaaccaa gctgtacctg ttgtaaaatg tgaaaccaat   780
gatttagaag ttccagcaga ttgtgaaatg gtatttgaag gttatttgga tagagatact   840
ttggttaccg aaggtccgtt tggggaaatg cacggttatt gtttcccaca agatcatcac   900
actcaaccgt tatatcgtgt caatcatata tcttaccgtg acgaagcaat catgccaata   960
tcaaacccag ggttatgtac tgatgagact catactttga ttggaggatt agtctctgct  1020
gagacaaagt atttgatttc caacacccta gtgttatcta aaattgtgga agatgtgttt  1080
accccttatg aagcacaagc attatggctt gctgtaaaaa tcaatatcca agaattgatt  1140
aaattgaaaa ctaatgcaaa agaattgctg aacttggtgg gtgatttttt attcaaatcc  1200
aaggaatgct ataaagtttg tctgattctt catgaagtta ttctcgttgg tgatgatatt  1260
gatattttcg atttcaaaca acttatttgg gcatatacta ctcgtcatac tccagttcag  1320
gatcaggtct atttttgatga cgttaaacct tttccattag ccccatttat ttctcaaggt  1380
cccttgatca agactcgtca aggtggtaaa tgtgtaacta gttgtatttt cccgaaacag  1440
tttacggatc cagactttaa atttgttact tgtaacttta atggttatcc cgaagaagtg  1500
aaaaataaag tatttcaaaa ctgggagaaa tattacaaat ga                     1542

<210> SEQ ID NO 48
<211> LENGTH: 1503
<212> TYPE: DNA
<213> ORGANISM: Aspergillus niger

<400> SEQUENCE: 48
atgtctgcgc aacctgctca cctgtgtttc cgctccttcg tcgaagccct caaggtcgac    60
aacgaccttg ttgaaatcaa taccccaatt gaccccaatc tcgaagctgc tgctattacc   120
cgccgagtat gtgagaccaa cgacaaggct cctttattca acaacctcat cggcatgaaa   180
aatggcctct tccgtatact tggggctcct ggctctctca ggaagtcgtc tgctgatcgc   240
tacggccgcc ttgctcgtca cctagccctc ccacctacgg cctcaatgcg tgagattctc   300

```
gataagatgc tctccgccag cgatatgcct cccatccctc cgaccattgt tcccaccggg      360
ccatgcaagg agaacagctt agatgactct gaattcgacc ttaccgaact ccccgttcct      420
cttattcaca aatcggatgg tggtaaatac atccaaacct atggcatgca cattgtgcag      480
tctccggatg gaacctggac caactggtct attgcccgtg cgatggtcca tgacaagaac      540
catctgaccg gcctggttat tcccctcag cacatctggc agattcacca gatgtggaag       600
aaggaaggcc gcagtgacgt tccctgggct ttggcctttg tgtcccacc cgctgccatt       660 atggcctcta gcatgcctat tcccgatggt gtcaccgaag ctgggtacgt gggagctatg      720
acgggatcct ccctggagct tgttaaatgt gatacgaacg atctatatgt ccccgctacc      780
tcagaaatcg ttctcgaggg cacactctct atcagcgaga caggcccaga gggacctttc      840
ggtgagatgc atggttacat cttccccggg gatactcacc tcggcgccaa atacaaggtt      900
aaccggatca cctaccgcaa caacgccatc atgcccatgt cttcttgtgg ccgcttgacg      960
gatgaaacgc acaccatgat cggctctctg gctgcggcgg agatccgtaa gctctgccag     1020
cagaatgacc tccctatcac tgatgccttc gctcctttcg agtctcaagt tacctgggtt     1080
gctctgcggg tcgatactga aagctacg gccatgaaga caacgtctga gggattccgc       1140
aagagagtgg gagacgtcgt cttcaaccac aaggccggat acaccattca tcgtctggtg     1200
ttggtcggtg acgacattga tgtctatgaa ggaaaggatg tgctctgggc gttctccacc     1260
cgttgccgtc ctggtatgga cgagactttg tttgaggatg ttcgtgggtt ccccttgatt     1320
ccgtatatgg gacacgggaa tgggcccgcc caccgcggcg gaaaggttgt gtccgacgct     1380
cttatgccga ctgagtacac cactggtcgc aactgggagg ctgctgactt caaccaatct     1440
tatcccgagg atctgaagca gaaggtgttg gacaactgga cgaagatggg tttcagcaac     1500
taa                                                                  1503
```

<210> SEQ ID NO 49
<211> LENGTH: 729
<212> TYPE: DNA
<213> ORGANISM: Saccharomyces cerevisiae

<400> SEQUENCE: 49

```
atgctcctat ttccaagaag aactaatata gccttttca aaacaacagg catttttgct      60
aattttcctt tgctaggtag aaccattaca acttcaccat ctttccttac acataaactg     120
tcaaaggaag taaccagggc atcaacttcg cctccaagac caaagagaat tgttgtcgca     180
attactggtg cgactggtgt tgcactggga atcagacttc tacaactgct aaaagagttg     240
agcgtagaaa cccatttggt gatttcaaaa tggggtgcag caacaatgaa atatgaaaca     300
gattgggaac cgcatgacgt ggcggccttg caaccaaga catactctgt tcgtgatgtt      360
tctgcatgca tttcgtccgg atctttccag catgatggta tgattgttgt gccctgttcc     420
atgaaatcac tagctgctat tagaatcggt tttacagagg atttaattac aagagctgcc     480
gatgtttcga ttaaagagaa tcgtaagtta ctactggtta ctcgggaaac ccctttatct     540
tccatccatc ttgaaaacat gttgtcttta tgcagggcag gtgttataat ttttcctccg     600
gtacctgcgt tttatacaag acccaagagc cttcatgacc tattgaaaca aagtgttggc     660
aggatcctag actgctttgg catccacgct gacactttc ctcgttggga aggaataaaa      720
agcaagtaa                                                              729
```

<210> SEQ ID NO 50

<211> LENGTH: 729
<212> TYPE: PRT
<213> ORGANISM: Saccharomyces cerevisiae

<400> SEQUENCE: 50

```
Ala Thr Gly Cys Thr Cys Cys Thr Ala Thr Thr Cys Cys Ala Ala
1               5                   10                  15

Gly Ala Ala Gly Ala Ala Cys Thr Ala Ala Thr Ala Thr Gly Cys
                20                  25                  30

Cys Thr Thr Thr Thr Thr Cys Ala Ala Ala Cys Ala Ala Cys Ala
                35                  40                  45

Gly Gly Cys Ala Thr Thr Thr Thr Gly Cys Thr Ala Ala Thr Thr
            50                  55                  60

Thr Thr Cys Cys Thr Thr Thr Gly Cys Thr Ala Gly Gly Thr Ala Gly
65                  70                  75                  80

Ala Ala Cys Cys Ala Thr Thr Ala Cys Ala Ala Cys Thr Cys Ala
                85                  90                  95

Cys Cys Ala Thr Cys Thr Thr Cys Cys Thr Ala Cys Ala Thr
                100                 105                 110

Ala Thr Ala Ala Ala Cys Thr Gly Thr Cys Ala Ala Ala Gly Gly Ala
                115                 120                 125

Ala Gly Thr Ala Ala Cys Cys Ala Gly Gly Thr Ala Thr Cys Ala
                130                 135                 140

Ala Cys Thr Thr Cys Gly Cys Cys Thr Cys Cys Ala Gly Ala Cys
145                 150                 155                 160

Cys Ala Ala Ala Gly Ala Gly Ala Ala Thr Thr Gly Thr Thr Gly Thr
                165                 170                 175

Thr Gly Cys Ala Ala Thr Thr Ala Cys Thr Gly Gly Thr Gly Cys Gly
                180                 185                 190

Ala Cys Thr Gly Gly Thr Gly Thr Thr Gly Cys Ala Cys Thr Gly Gly
                195                 200                 205

Gly Ala Ala Thr Cys Ala Gly Ala Cys Thr Thr Cys Thr Ala Cys Ala
                210                 215                 220

Ala Gly Thr Gly Cys Thr Ala Ala Ala Gly Ala Gly Thr Thr Gly
225                 230                 235                 240

Ala Gly Cys Gly Thr Ala Gly Ala Ala Cys Ala Cys Ala Thr Thr
                245                 250                 255

Thr Gly Gly Thr Gly Ala Thr Thr Cys Ala Ala Ala Thr Gly
                260                 265                 270

Gly Gly Gly Thr Gly Cys Ala Gly Cys Ala Ala Cys Ala Ala Thr Gly
                275                 280                 285

Ala Ala Ala Thr Ala Thr Gly Ala Ala Ala Cys Ala Gly Ala Thr Thr
                290                 295                 300

Gly Gly Gly Ala Ala Cys Cys Gly Cys Ala Thr Gly Ala Cys Gly Thr
305                 310                 315                 320

Gly Gly Cys Gly Gly Cys Cys Thr Gly Gly Cys Ala Ala Cys Cys
                325                 330                 335

Ala Ala Gly Ala Cys Ala Thr Ala Cys Thr Cys Thr Gly Thr Thr Cys
                340                 345                 350

Gly Cys Gly Ala Thr Gly Thr Thr Cys Gly Cys Ala Thr Gly
                355                 360                 365

Cys Ala Thr Thr Thr Cys Gly Thr Cys Cys Gly Gly Ala Thr Cys Thr
                370                 375                 380

Thr Thr Cys Cys Ala Gly Cys Ala Thr Gly Ala Thr Gly Gly Thr Ala
```

```
                385                 390                 395                 400
Thr Gly Ala Thr Thr Gly Thr Thr Gly Thr Gly Cys Cys Thr Gly
                405                 410                 415
Thr Thr Cys Cys Ala Thr Gly Ala Ala Ala Thr Cys Ala Cys Thr Ala
                420                 425                 430
Gly Cys Thr Gly Cys Thr Ala Thr Ala Gly Ala Ala Thr Thr Gly
                435                 440                 445
Gly Thr Thr Thr Ala Cys Ala Gly Ala Gly Ala Thr Thr Thr
                450                 455                 460
Ala Ala Thr Thr Ala Cys Ala Gly Ala Gly Cys Thr Gly Cys Cys
465                 470                 475                 480
Gly Ala Thr Gly Thr Thr Cys Gly Ala Thr Ala Ala Ala Gly
                485                 490                 495
Ala Gly Ala Ala Thr Cys Gly Thr Ala Ala Gly Thr Thr Ala Cys Thr
                500                 505                 510
Ala Cys Thr Gly Gly Thr Thr Ala Cys Thr Cys Gly Gly Gly Ala Ala
                515                 520                 525
Ala Cys Cys Cys Cys Thr Thr Thr Ala Thr Cys Thr Thr Cys Cys Ala
                530                 535                 540
Thr Cys Cys Ala Thr Cys Thr Thr Gly Ala Ala Ala Ala Cys Ala Thr
545                 550                 555                 560
Gly Thr Thr Gly Thr Cys Thr Thr Ala Thr Gly Cys Ala Gly Gly
                565                 570                 575
Gly Cys Ala Gly Gly Thr Gly Thr Thr Ala Thr Ala Ala Thr Thr Thr
                580                 585                 590
Thr Thr Cys Cys Thr Cys Cys Gly Gly Thr Ala Cys Cys Thr Gly Cys
                595                 600                 605
Thr Thr Thr Thr Thr Ala Thr Ala Cys Ala Ala Gly Ala Cys Cys Cys
                610                 615                 620
Ala Ala Gly Ala Gly Cys Cys Thr Thr Cys Ala Thr Gly Ala Cys Cys
625                 630                 635                 640
Thr Ala Thr Thr Ala Gly Ala Ala Cys Ala Ala Gly Thr Gly Thr
                645                 650                 655
Thr Gly Gly Cys Ala Gly Gly Ala Thr Cys Cys Thr Ala Gly Ala Cys
                660                 665                 670
Thr Gly Cys Thr Thr Thr Gly Gly Cys Ala Thr Cys Ala Cys Gly
                675                 680                 685
Cys Thr Gly Ala Cys Ala Cys Thr Thr Thr Cys Cys Thr Cys Gly
                690                 695                 700
Thr Thr Gly Gly Gly Ala Ala Gly Gly Ala Ala Thr Ala Ala Ala
705                 710                 715                 720
Ala Gly Cys Ala Ala Gly Thr Ala Ala
                725
```

<210> SEQ ID NO 51
<211> LENGTH: 729
<212> TYPE: DNA
<213> ORGANISM: Saccharomyces cerevisiae

<400> SEQUENCE: 51
atgctcctat ttccaagaag aactaatata gccttttca aacaacagg catttttgct    60 aattttcctt tgctaggtag aaccattaca acttcaccat ctttccttac atataaactg   120 tcaaggaag taaccagggt atcaacttcg cctccaagac caaagagaat tattgttgca   180

```
attactggtg cgactggtgt tgcactggga atcagacttc tacaagtgct aaaagagttg    240
agcgtagaaa cccatttggt gatttcaaaa tggggtgcag caacaatgaa atatgaaaca    300
gattgggaac cgcatgacgt ggcggccttg gcaaccaaga catactctgt tcgcgatgtt    360
tctgcatgca tttcgtccgg atctttccag catgatggta tgattgttgt gccctgttcc    420
atgaaatcac tagctgctat tagaatcggt tttacagagg atttaattac aagagctgcc    480
gatgtttcga ttaaagagaa tcgtaagtta ctactggtta ctcgggaaac ccctttatct    540
tccatccatc ttgaaaacat gttgtcttta tgcagggcag gtgttataat ttttcctccg    600
gtacctgcgt tttatacaag acccaagagc cttcatgacc tattagaaca agtgttggc    660 aggatcctag actgctttgg catccacgct gacactttc ctcgttggga aggaataaaa    720
agcaagtaa                                                            729
```

<210> SEQ ID NO 52
<211> LENGTH: 729
<212> TYPE: DNA
<213> ORGANISM: Saccharomyces cerevisiae
<400> SEQUENCE: 52

```
atgctcctat ttccaagaag aactaatata gccttttca aaacaacagg cattttgct     60 aattttcctt tgctaggtag aaccattaca acttcaccat ctttccttac atataaactg    120
tcaaaggaag taaccagggt atcaacttcg cctccaagac caagagaat tgttgttgca    180 attactggtg cgactggtgt tgcactggga atcagacttc tacaagtgct aaaagagttg    240
agcgtagaaa cacatttggt gatttcaaaa tggggtgcag caacaatgaa atatgaaaca    300
gattgggaac cgcatgacgt ggcggccttg gcaaccaaga catactctgt tcgcgatgtt    360
tctgcatgca tttcgtccgg atctttccag catgatggta tgattgttgt gccctgttcc    420
atgaaatcac tagctgctat tagaattggt tttacagagg atttaattac aagagctgcc    480
gatgtttcga ttaaagagaa tcgtaagtta ctactggtta ctcgggaaac ccctttatct    540
tccatccatg ttgaaaacat gttgtcttta tgcagggcag gtgttataat ttttcctccg    600
gtacctgctt tttatacaag acccaagagc cttcatgacc tattagaaca agtgttggc    660 aggatcctag actgctttgg catccacgct gacactttc ctcgttggga aggaataaaa    720
agcaagtaa                                                            729
```

<210> SEQ ID NO 53
<211> LENGTH: 729
<212> TYPE: DNA
<213> ORGANISM: Saccharomyces cerevisiae
<400> SEQUENCE: 53

```
atgctcctat ttccaagaag aactaatata gccttttca aaacaacagg cattttgct     60 aattttcctt tgctaggtag aaccattaca acttcaccat ctttccttac atataaactg    120
tcaaaggaag taaccagggt atcaacttcg cctccaagac caagagaat tgttgttgca    180 attactggtg cgactggtgt tgcactggga atcagacttc tacaagtgct aaaagagttg    240
agcgtagaaa cacatttggt gatttcaaaa tggggtgcag caacaatgaa atatgaaaca    300
gattgggaac cgcatgacgt ggcggccttg gcaaccaaga catactctgt tcgcgatgtt    360
tctgcatgca tttcgtccgg atctttccag catgatggta tgattgttgt gccctgttcc    420
atgaaatcac tagctgctat tagaattggt tttacagagg atttaattac aagagctgcc    480
gatgtttcga ttaaagagaa tcgtaagtta ctactggtta ctcgggaaac ccctttatct    540
```

```
tccatccatg ttgaaaacat gttgtcttta tgcagggcag gtgttataat ttttcctccg     600
gtacctgctt tttatacaag acccaagagc cttcatggcc tattagaaca aagtgttggc     660
aggatcctag actgctttgg catccacgct gacactttc ctcgttggga aggaataaaa     720
agcaagtaa                                                             729

<210> SEQ ID NO 54
<211> LENGTH: 729
<212> TYPE: DNA
<213> ORGANISM: Saccharomyces cerevisiae

<400> SEQUENCE: 54
atgtttaagt taccaagcaa agttaactta gcttctttca aggtaaagg tcatttagct      60 aagtttccct tgcggagcag aagcatttca aactcttcgt taccccttc atatatgaca    120 ccaaaggagg tttcaaatgt atcagcttct cctccaagac caaagagaat tgttgtggcg   180
attactggtg ctactggggt tgcattaggg attaaacttc ttcagatact aaaagaattg   240
agcgtcgaaa ctcatttgat aatatcgaaa tggggtgcag caaccatgaa gtatgaaacg   300
gactgggaac acacatgatgt ggcggccttg gcatccaaaa cgtactctgt tcgggatgtt  360
tccgcgtgca tttcatccgg gtcttttcag catgatggaa tgattgtggc accctgttct   420
atgaaaacgt tggctgcgat tagaatcggt tttacagagg atttgattac gagagcggct   480
gatgtttcca ttaaagagaa ccgaaagtta ctactagtta ctcgagaaac acctctgtcc  540
gctattcacc ttgaaaacat gctattccta cgcaggactg gtgttataat ttttcctccg   600
gtacctgcat attatacaaa acccaaaagc atgaatgacc tgttggaaca gagtgccggc   660
agaatcctag attgctttgg tattcatgct gatactttc ctcgatggga aggtataaag   720
attaagtag                                                            729

<210> SEQ ID NO 55
<211> LENGTH: 693
<212> TYPE: DNA
<213> ORGANISM: Saccharomyces cerevisiae

<400> SEQUENCE: 55
atgctcctat ttccaagaag aactaatata gccttttca aaacaacagg cattttttgct    60 aattttcctt tgctaggtag aaccattaca acttcaccat ctttccttac atataaactg   120
tcaaaggaag taaccagggt atcaacttcg cctccaagac caaagagaat tgttgttgca   180
attactggtc gactggtgt tgcactggga atcagacttc tacaagtgct aaaagagttg    240
agcgtagaaa cacatttggt gatttcaaaa tggggtgcag caacaatgaa atatgaaaca   300
gattgggaac gcatgacgt ggcggccttg gcaaccaaga catactctgt tcgcgatgtt   360
tctgcatgca tttcgtccgg atcttttcag catgatggta tgattgttgt gccctgttcc  420
atgaaatcac tagctgctat tagaattggt tttacagagg atttaattac aagagctgcc   480 gatgttcga ttaaagagaa tcgtaagtta ctactggtta ctcgggaaac ccctttatct   540
tccatccatg ttgaaaacat gttgtcttta tgcagggcag gtgttataat ttttcctccg    600
gtacctgctt tttatacaa acccaagag ccttcatgrc ctattagaac aaagtgttgg    660
caggatccta gactgctttg gcatccacgc tga                                 693

<210> SEQ ID NO 56
<211> LENGTH: 747
<212> TYPE: DNA
```

<213> ORGANISM: Debaryomyces hansenii

<400> SEQUENCE: 56

| | | | | | |
|---|---|---|---|---|---|
| atgaagtcta | gttctatggg | acacagatca | ataaggatat | ctaattatat | gtttaggcct | 60 |
| ttctcaatat | catcgacaat | cagaaacaag | aatccgatta | gcgactatga | acaggtttcc | 120 |
| aacgatatat | accagaatca | gtcaacagga | ttgtatctta | caagacctaa | gaggatagtc | 180 |
| gtggcaataa | ctggggctac | aggtattgca | atcggtgtaa | gggtattgga | attattaaag | 240 |
| caatgtaaag | ttgagacaca | tttaattatg | tccaaatggg | gtatggcaac | aatgaaatat | 300 |
| gaaacagatt | atcatatgga | cgacataatg | gcacttgcgt | caaggtgta | cactgccaga | 360 |
| gacgtgagtg | cgccgatttc | gtcaggatct | ttccaacacg | atggtatgat | tgtcgtgcca | 420 |
| tgttcgatga | agacattggc | tgggattagg | atgggattca | cagaggatct | tatcgtaagg | 480 |
| gccgctgatg | ttacattgaa | ggaaagaaga | aagttattat | tagttaccag | agaaacaccg | 540 |
| ttatctgaca | tacatttgga | taatatgtta | tatttatcaa | gaatggggac | aattatcttc | 600 |
| cccccagtac | ctgcattta | tacaaaacct | agaacggtag | aggatatcat | gaacaaagt | 660 |
| agtggaaggg | tattggattg | ttttgggatt | gatacaaata | ctttcccacg | ttgggaaggt | 720 |
| gttaaagata | caaaaacact | taaatag | | | | 747 |

<210> SEQ ID NO 57
<211> LENGTH: 744
<212> TYPE: DNA
<213> ORGANISM: Zygosaccharomyces rouxii

<400> SEQUENCE: 57

| | | | | | |
|---|---|---|---|---|---|
| atgcttggaa | tgcaattctt | ctccagagca | ttgtgtgtcg | gaggccacgt | taggtctttt | 60 |
| tgtttctcac | aagtccgggg | tccggtaaaa | ttacgctcat | ttggcacaaa | cctggcaaag | 120 |
| agaaattctt | cttcaagtag | tttgacagaa | aaacaagtgt | gtaatgggac | agttgcacca | 180 |
| aagcctaaaa | gaattgtcgt | atctattaca | ggcgctacag | ggatagctct | cggggtgcgt | 240 |
| atcttacaga | tattaaaaga | attaaatgtt | gaaacacatc | ttatcatttc | caagtgggga | 300 |
| atggcaacga | tgaagtatga | aactgatttt | actttggaag | atttacgttc | cattgcaacg | 360 |
| cacacttatc | cggctaaaaa | tgtagcggca | gctgtttctt | ctggatcatt | ccttcatgat | 420 |
| ggtatgatag | ttgttccgtg | ctcgatgaaa | actttagcgg | ctatcagatg | tggatatacg | 480 |
| gaagatttga | ttgtaagggc | agcggatgtg | actctcaaag | agaaacgaaa | acttctcgtt | 540 |
| gttcctaggg | agactccatt | gtctgaaatc | catttagaaa | atatgctttc | tctagcgaga | 600 |
| atgggagtta | ttatctttcc | acctgttcct | gcttttata | caaaacctac | ttccctggat | 660 |
| gacattatag | aacaatcctg | cggaagaatt | tggactgct | ttggaattca | tacgaataat | 720 |
| ttttcccgat | gggatggatt | ttaa | | | | 744 |

<210> SEQ ID NO 58
<211> LENGTH: 690
<212> TYPE: DNA
<213> ORGANISM: Candida dubliniensis

<400> SEQUENCE: 58

| | | | | | |
|---|---|---|---|---|---|
| atgattgcaa | gagtttgttt | gaaaagacca | aatgctttac | ccattttct | gatttcatcg | 60 |
| agaaagtatt | ccattgatta | tgaaaaagtc | aataactcgg | tatataacaa | tgtcatcata | 120 |
| cccaaaagaa | tagtcttggc | aattactggt | gccacgggaa | cccaaatagg | agtgagatta | 180 |
| ttagaaatat | tgaaagaact | aggagtggaa | acccatttgg | tgatgtctaa | atgggggatt | 240 |

```
gccactttga aatatgaaac tgattatcaa gttgattatg tcacgtcctt agctacaaaa      300
acatattctg caagggatgt aacagcacca atatcttcag ggtcatttgt tcacgacgga      360
atgattgttg ctccttgttc aatgaaatca ctttcagcta ttagaactgg tttcactgaa      420
gatttgatag tcagagcagc tgatgtttcc ttaaaggaaa gacgtaaatt gttattggtt      480
gctcgagaaa ctcctctttc cgatattcat ttggataata tgctttattt actgcgaatg      540
ggggtgataa tattcccgcc agtaccagca ttttatacaa aaccaaaaac tgttgatgat      600
attattgagc aaacatgtgg aagaatatta gataatttcg gaattaacat agacacgttt      660
gagagatggg atggaatcaa tcataaatag                                      690

<210> SEQ ID NO 59
<211> LENGTH: 690
<212> TYPE: DNA
<213> ORGANISM: Candida albicans

<400> SEQUENCE: 59
atgattgcga gagattgttt gagaagacag aatgttttac ccattttca gattccatcg       60 agaaagtatt ctattaatta tgaaaagtg aataactcaa tatataacaa tgtgatcaaa      120
cccaaaagaa tagttttagc aatcaccggt gccacgggga ctcaaatagg ggtaaggtta      180
ttagaaatat tgaaagaatt gggtgtggaa actcatttgg tcatgtcaaa atgggggatt      240
gctactttga aatacgaaac tgattatcaa gttgattatg tcacttcatt ggctacaaaa      300
acatactctg caagggatgt aacagcacca atatcttcag ggtcatttgt tcatgatgga      360
atgattgttg ccccttgttc aatgaaatca ctttcagcta tcagaactgg ttttacggaa      420
gatttgatag ttagagctgc tgatgtttct ttaaagaaa ggcgtaaatt gttattagtt       480
gctcgagaaa ctcctctttc agatattcat ttggataata tgctatattt actgcgaatg      540
ggggtgacaa tattcccacc tgtgccagca ttttatacaa aaccaaaaac tattgatgat      600
attgtggaac aaacctgtgg aagaatatta gatattttg gaattaatat agacacgttc      660
gagagatggg atggaattaa ccatagatag                                      690
```

METHODS FOR PREPARING A HYDROCARBON

CROSS-REFERENCE TO RELATED APPLICATIONS

The present application claims the benefit of priority from European Application. No. 12171463.8 filed Jun. 11, 2012, the disclosure of which is incorporated by reference in its entirety.

REFERENCE TO A "SEQUENCE LISTING"

The Sequence Listing written in file TS7857-US-NP_ST25.TXT, created on Jun. 10, 2013 is hereby incorporated by reference in its entirety.

FIELD OF THE INVENTION

Embodiments of the invention relate to improved methods for the production of alkenes useful in the production of biofuels and/or biochemicals, and expression vectors and host cells useful in such methods.

BACKGROUND TO THE INVENTION

With the diminishing supply of crude mineral oil, use of renewable energy sources is becoming increasingly important for the production of liquid fuels and/or chemicals. These fuels and/or chemicals from renewable energy sources are often referred to as biofuels. Biofuels and/or biochemicals derived from non-edible renewable energy sources are preferred as these do not compete with food production.

Hydrocarbons such as alkenes are important constituents in the production of fuels and/or chemicals. It would therefore be desirable to produce alkenes (sometimes also referred to as bio-alkenes) from non-edible renewable energy sources.

SUMMARY OF THE INVENTION

A first aspect of the invention provides a method for preparing a mono-unsaturated alkene, comprising contacting an aliphatic mono-unsaturated carboxylic acid with an Fdc1 polypeptide (herein also referred to as ferulic acid decarboxylase polypeptide or ferulic acid decarboxylase enzyme) comprising an amino acid sequence with at least 21% sequence identity to SEQ ID NO: 1 and a Pad1 polypeptide (herein also referred to as phenacrylate decarboxylase polypeptide or phenacrylate decarboxylase enzyme) comprising an amino acid sequence with at least 17% sequence identity to SEQ ID NO: 2.

In a preferred embodiment, the invention provides a method for preparing a terminal mono-unsaturated alkene, comprising contacting an aliphatic $\alpha,\beta$-mono-unsaturated carboxylic acid with a first polypeptide having ferulic acid decarboxylase activity, which first polypeptide comprises a first amino acid sequence with at least 21%, preferably at least 30% sequence identity, more preferably at least 50% sequence identity, to the amino acid sequence set out in SEQ ID NO: 1, and with a second polypeptide having phenacrylate decarboxylase activity, which second polypeptide comprises a second amino acid sequence with at least 17%, preferably at least 37% sequence identity, more preferably at least 60% sequence identity, to the amino acid sequence set out in SEQ ID NO: 2.

Without wishing to be bound by any kind of theory it is believed that decarboxylation of carboxylic acids by biological catalysts working under ambient conditions often requires the use of co-factors (for example thiamine; biotin; metals) that act as transient electron acceptors. It is believed that the heterolytic bond breakage of the C—C bond that gives rise to $CO_2$ may result in carbanion species that are highly unstable, unless the electron pair can be delocalised. There have been reports of enzymes that do not require cofactors, but such enzymes often have very strict substrate requirements.

The so-called Fdc1/Pad1 enzyme system belongs to a family of enzymes that broadly catalyses the reversible decarboxylation of aromatic groups. The co-factor requirement, mechanism or individual properties of the family members have not been reported in any detail to date.

The yeast Fdc1 and Pad1 enzymes have been implicated in decarboxylation of aromatic substrates (see the article of Mukai N et al. (2010) J. Biosci. Bioeng. 109, 564-569). Pad1 enzyme also has been singly implicated in decarboxylation of sorbic acid (see the article of Stratford M et al. (2007) Appl. Environ. Microbiol. 73, 6534-6542). All these substrates have a minimum of two double bonds adjacent to the carboxylic group in common, which would have been expected to be key to the enzyme mechanism. Surprisingly, it has now been found that generation of terminal alkenes by decarboxylation of an aliphatic mono-unsaturated carboxylic acid with a carbon double bond between the $\alpha$ and $\beta$ positions is possible using a combination of Fdc1 and Pad1.

Other features of embodiments of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Embodiments of the invention may be better understood by reference to the drawing in combination with the detailed description of specific embodiments presented herein.

FIG. 4 shows the results of a high-throughput pH-based screening of enzymatic activity of purified Fdc1/Pad1;

FIGS. 6A and 6B show 1-pentene identification by GC-MS.

DETAILED DESCRIPTION OF THE PREFERRED EMBODIMENTS

Figure 1:
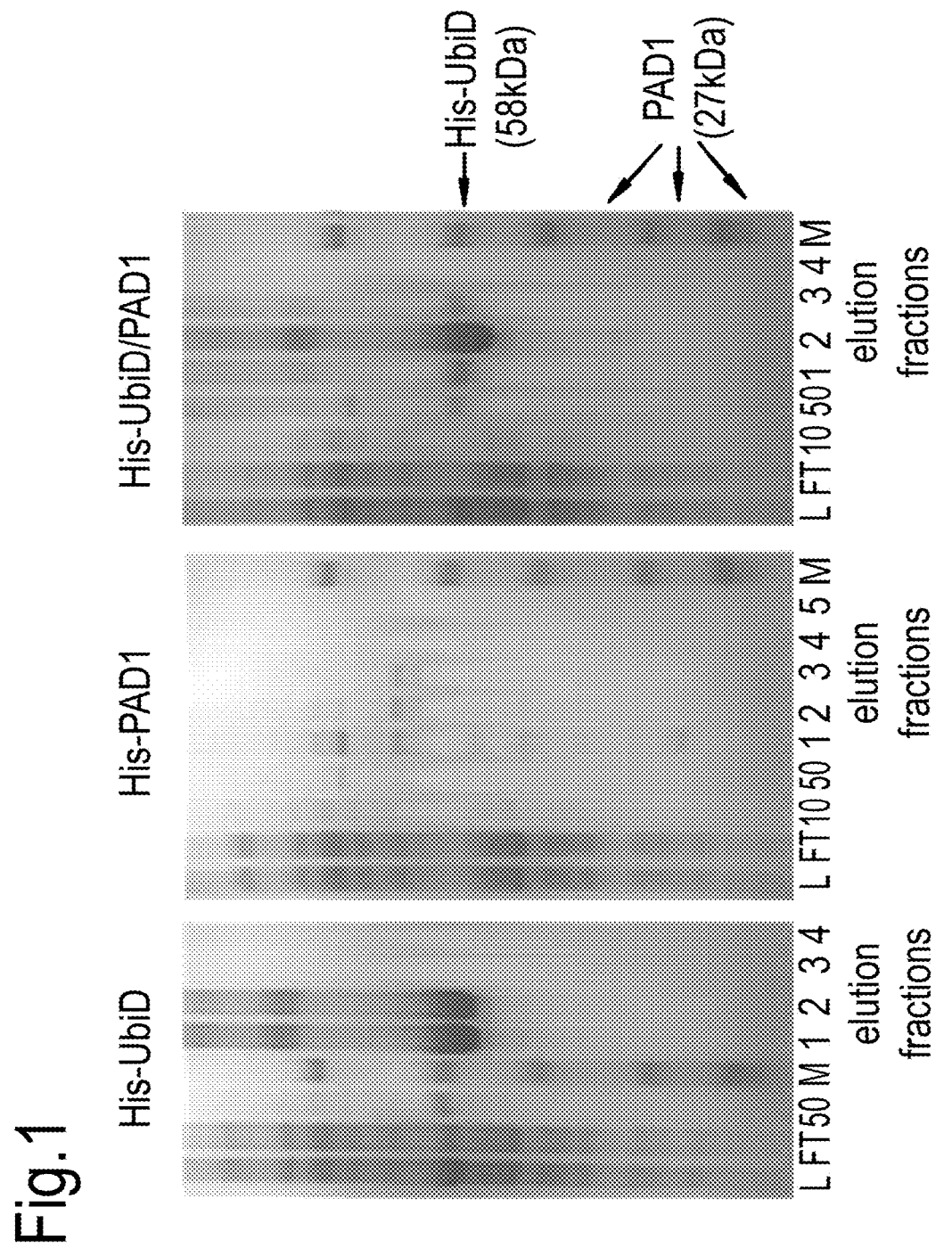
FIG. 1 shows a series of SDS-PAGE gels of protein purification expression trials: for samples containing Fdc1.

Unless otherwise defined herein, scientific and technical terms used herein will have the meanings that are commonly understood by those of ordinary skill in the art.

Generally, nomenclatures used in connection with techniques of biochemistry, enzymology, molecular and cellular biology, microbiology, genetics and protein and nucleic acid chemistry and hybridization, described herein, are those well known and commonly used in the art.

Conventional methods and techniques mentioned herein are explained in more detail, for example, in Sambrook et al.

(Molecular Cloning, a laboratory manual [second edition] Sambrook et al. Cold Spring Harbor Laboratory, 1989).

The identity of amino acid sequences and nucleotide sequences referred to in this specification is as set out in Table 3 at the end of the description. The terms "polynucleotide", "polynucleotide sequence" and "nucleic acid sequence" are used interchangeably herein. The terms "polypeptide", "polypeptide sequence" and "amino acid sequence" are, likewise, used interchangeably herein. Other sequences encompassed by the invention are provided in the Sequence Listing and listed in Tables 4 and 5 with reference to GenBank accession numbers.

Enzyme Commission (EC) numbers (also called "classes" herein), referred to throughout this specification, are according to the Nomenclature Committee of the International Union of Biochemistry and Molecular Biology (NC-IUBMB) in its resource "Enzyme Nomenclature" (1992, including Supplements 6-17) This is a numerical classification scheme based on the chemical reactions catalysed by each enzyme class (Enzyme nomenclature 1992: recommendations of the Nomenclature Committee of the International Union of Biochemistry and Molecular Biology on the nomenclature and classification of enzymes. Webb, E. C. (1992). San Diego: Published for the International Union of Biochemistry and Molecular Biology by Academic Press. ISBN 0-12-227164-5). The skilled person can readily determine whether an enzyme falls within any particular enzyme class as referred to herein, for example using methods obtainable from the International Union of Biochemistry and Molecular Biology (IUBMB).

The term "Fdc1 polypeptide" indicates a ferulic acid decarboxylase enzyme in class EC No. 4.1.1. The term "Fdc1 polypeptide" is used interchangeably herein with the terms "Fdc1 enzyme" and "Fdc1 protein". The "first polypeptide having ferulic acid decarboxylase activity" is preferably a "Fdc1 polypeptide". The "Fdc1 polypeptide" or "first polypeptide having ferulic acid decarboxylase activity" may comprise the amino acid sequence SEQ ID NO: 1 (*Saccharomyces cerevisiae* Fdc1 protein) or a variant amino acid sequence, which is at least 21% identical, more preferably at least 30%, even more preferably at least 50% or at least 55% identical, to SEQ ID NO: 1 (for example, a sequence listed in Table 4, such as SEQ ID NOS:1 and 16-26). More preferably the "Fdc1 polypeptide" or "first polypeptide having ferulic acid decarboxylase activity" consists essentially of the amino acid sequence SEQ ID NO: 1 or a variant amino acid sequence, which is at least 21% identical, more preferably at least 30%, even more preferably at least 50% or at least 55% identical, to SEQ ID NO: 1. Most preferably the "Fdc1 polypeptide" or "first polypeptide having ferulic acid decarboxylase activity" consists of the amino acid sequence SEQ ID NO: 1 or a variant amino acid sequence, which is at least 21% identical, more preferably at least 30%, even more preferably at least 50% or at least 55% identical, to SEQ ID NO: 1.

The term "Pad1 polypeptide" indicates a phenacrylate decarboxylase enzyme in class EC No. 4.1.1. The term "Pad1 polypeptide" is used interchangeably herein with the terms "Pad1 enzyme" and "Pad1 protein". The "second polypeptide having phenacrylate decarboxylase activity" is preferably a "Pad1 polypeptide". The "Pad1 polypeptide" or "second polypeptide having phenacrylate decarboxylase activity" may comprise the amino acid sequence SEQ ID NO: 2 (*Saccharomyces cerevisiae* Pad1 protein) or a variant amino acid sequence, which is at least 17% identical, more preferably at least 37%, even more preferably at least 60% or at least 65% identical, to SEQ ID NO: 2 (for example, a sequence listed in Table 5, such as SEQ ID NOS:2 and 27-37). More preferably the "Pad1 polypeptide" or "second polypeptide having phenacrylate decarboxylase activity" consists essentially of the amino acid sequence SEQ ID NO: 2 or a variant amino acid sequence, which is at least 17% identical, more preferably at least 37%, even more preferably at least 60% or at least 65% identical, to SEQ ID NO: 2. Most preferably the "Pad1 polypeptide" or "second polypeptide having phenacrylate decarboxylase activity" consists of the amino acid sequence SEQ ID NO: 2 or a variant amino acid sequence, which is at least 17% identical, more preferably at least 37%, even more preferably at least 60% or at least 65% identical, to SEQ ID NO: 2.

When an aliphatic mono-unsaturated carboxylic acid is contacted by both the Fdc1 polypeptide and the Pad1 polypeptide, respectively by both the first polypeptide having ferulic acid decarboxylase activity and the second polypeptide having phenacrylate decarboxylase activity, it is possible to generate an alkene, which alkene comprises only one unsaturated carbon-to-carbon bond. Advantageously, generation of a terminal alkene is possible from an aliphatic carboxylic acid with a carbon double bond between the α and β positions. That is, the invention advantageously allows for the generation of a mono-unsaturated terminal alkene, by contacting an aliphatic mono-unsaturated carboxylic acid, with a carbon double bond between the α and β positions, by both the Fdc1 polypeptide and the Pad1 polypeptide, respectively by both the first polypeptide having ferulic acid decarboxylase activity and the second polypeptide having phenacrylate decarboxylase activity.

By an "alkene" is herein understood an unsaturated aliphatic hydrocarbon compound comprising at least one carbon-to-carbon double bond. "Hydrocarbon compounds" are herein also referred to as "hydrocarbons". By a "hydrocarbon compound" is herein understood a compound consisting of hydrogen and carbon. Examples of suitable alkenes that can be prepared (i.e. produced) using the method of the invention have in the range from equal to or more than 4 to equal to or less than 30 carbon atoms in linear or branched formation and comprise one or more double bonds. Particular examples of alkenes that can be prepared using the method of the invention include straight- or branched-chain alkenes having up to 2, 3, 4, 5, 6, 7, 8, 9, 10, 11, 12, 13, 14, 15, 16, 17, 18, 19 or up to 20 carbon atoms.

The one or more alkenes prepared using the method of the invention are mono-unsaturated alkenes. By a "mono-unsaturated alkene" is herein understood an alkene comprising only one unsaturated carbon-to-carbon bond, which one unsaturated carbon-to-carbon bond is a carbon-to-carbon double bond.

In a preferred embodiment, the one or more alkenes prepared (i.e. produced) are terminal alkenes. Such a "terminal alkene" may herein also be referred to as for example an "1-alkene", an "alpha-alkene", an "α-alkene" or an "α-olefin". By a "terminal alkene" is herein understood an alkene comprising a carbon-to-carbon double bond between a terminal carbon atom and its adjacent carbon atom in the alkene. That is, in a preferred embodiment the one or more alkenes prepared using the method of the invention are terminal mono-unsaturated alkenes. By an "aliphatic unsaturated carboxylic acid" is herein understood an aliphatic carboxylic acid comprising an unsaturated carbon-to-carbon bond. By an "aliphatic mono-unsaturated carboxylic acid" is herein understood an aliphatic unsaturated carboxylic acid having only one unsaturated carbon-to-carbon bond. Preferably the unsaturated carbon-to-carbon bond is a so-called carbon-to-carbon double bond. Hence, preferably the aliphatic unsaturated carboxylic acid is an aliphatic unsaturated carboxylic acid comprising a single carbon-to-carbon double bond.

Thus, preferably the aliphatic mono-unsaturated carboxylic acid is an alkenoic acid. Alkenoic acids are herein also referred to as "enoic acids". By an alkenoic acid is herein understood an unsaturated aliphatic carboxylic acid comprising a carbon-to-carbon double bond. More preferably the aliphatic mono-unsaturated carboxylic acid is an alpha-alkenoic acid (also sometimes referred to as for example α-alkenoic acid or 2-alkenoic acid). By an alpha-alkenoic acid is herein understood an unsaturated aliphatic carboxylic acid that comprises a carbon-to-carbon double bond between the α and β positions of the carbon chain (relative to the carboxyl group). When the aliphatic mono-unsaturated carboxylic acid is such an alpha-alkenoic acid, the alkene prepared in the method according to the invention may advantageously be a terminal alkene.

In an especially preferred embodiment, the aliphatic mono-unsaturated carboxylic acid is an aliphatic α,β-mono-unsaturated carboxylic acid. By such an "aliphatic α,β-mono-unsaturated carboxylic acid" is herein understood an aliphatic carboxylic acid, comprising any one single unsaturated carbon-to-carbon bond, which single unsaturated carbon-to-carbon bond is located between the α-carbon and the β-carbon of the carboxylic acid. Preferably the aliphatic α,β-mono-unsaturated carboxylic acid, is an aliphatic α,β-mono-unsaturated carboxylic acid with a single carbon-to-carbon double bond. Such an aliphatic α,β-mono-unsaturated carboxylic acid with a single carbon-to-carbon double bond may herein also be referred to as an "α,β-mono-unsaturated alkenoic acid". Hence, preferably the aliphatic mono-unsaturated carboxylic acid is an aliphatic α,β-mono-unsaturated alkenoic acid. As explained above, the alkene prepared when using such an aliphatic α,β-mono-unsaturated alkenoic acid may advantageously be a terminal mono-unsaturated alkene.

More than one type of carboxylic acid may be contacted with the Fdc1 and Pad1 polypeptides in a single step, resulting in the production of a mixture of alkenes, dependent on the carboxylic acids initially present, before an embodiment of the invention is carried out. In a preferred embodiment a mixture of alkenes, comprising at least one or more terminal mono-unsaturated alkenes, is prepared by contacting a mixture of aliphatic unsaturated carboxylic acids comprising at least one or more α,β-mono-unsaturated alkenoic acids.

Embodiments of the invention may subsequently comprise isolating the alkene and/or mixture of alkenes. The term "isolating the alkene" indicates that the alkene, or mixture of alkenes, is separated from other non-hydrocarbon components. This may indicate that, for example, at least about 50% by weight of a sample after separation is composed of the alkene(s), for example, at least about 60%, 70%, 75%, 80%, 85%, 90%, 95%, 96%, 97%, 98% 99% or 100%. The alkene produced during the working of the invention can be separated (i.e., isolated) by any known technique. One exemplary process is a two-phase (bi-phasic) separation process, involving conducting the method for a period and/or under conditions sufficient to allow the alkene(s) to collect in an organic phase and separating the organic phase from an aqueous phase. This may be especially relevant when, for example, the method is conducted within a host cell such as a micro-organism, as described below. Bi-phasic separation uses the relative immiscibility of hydrocarbons to facilitate separation. "Immiscible" refers to the relative inability of a compound to dissolve in water and is defined by the compound's partition coefficient, as will be well understood by the skilled person.

In an embodiment of the invention, the Fdc1 and/or Pad1 polypeptides (respectively the "first polypeptide having ferulic acid decarboxylase activity" and/or "second polypeptide having phenacrylate decarboxylase activity") are expressed by a recombinant host cell, such as a recombinant microorganism. Therefore, an aspect of the invention may take place within a host cell, i.e., the method may be at least partially an in vivo method. The host cell may be recombinant and may, for example, be a genetically modified microorganism. Therefore, a micro-organism may be genetically modified, i.e., artificially altered from its natural state, to express at least one of the Fdc1 and/or Pad1 polypeptides (respectively the "first polypeptide having ferulic acid decarboxylase activity" and/or "second polypeptide having phenacrylate decarboxylase activity") and, preferably, both of these. Other enzymes described herein may also be expressed by a micro-organism. Preferably, the enzymes are exogenous, i.e., not present in the cell prior to modification, having been introduced using microbiological methods such as are described herein. Furthermore, in the method of the invention, the enzymes may each be expressed by a recombinant host cell, either within the same host cell or in separate host cells. The hydrocarbon may be secreted from the host cell in which it is formed.

The host cell may be genetically modified by any manner known to be suitable for this purpose by the person skilled in the art. This includes the introduction of the genes of interest, such as one or more genes encoding the Fdc1 and/or Pad1 polypeptides (respectively the "first polypeptide having ferulic acid decarboxylase activity" and/or "second polypeptide having phenacrylate decarboxylase activity"), on a plasmid or cosmid or other expression vector which reproduces within the host cell. Alternatively, the plasmid or cosmid DNA or part of the plasmid or cosmid DNA or a linear DNA sequence may integrate into the host genome, for example by homologous recombination. To carry out genetic modification, DNA can be introduced or transformed into cells by natural uptake or mediated by processes such as electroporation. Genetic modification can involve expression of a gene under control of an introduced promoter. The introduced DNA may encode a protein which could act as an enzyme or could regulate the expression of further genes.

Such a host cell may comprise a nucleic acid sequence encoding a Fdc1 and/or Pad1 polypeptide (respectively the "first polypeptide having ferulic acid decarboxylase activity" and/or "second polypeptide having phenacrylate decarboxylase activity"). For example, the cell may comprise at least one nucleic acid sequence comprising at least one of the polynucleotide sequences SEQ ID NOS:3-7 or 38-59 or a complement thereof, or a fragment of such a polynucleotide encoding a functional variant or fragment of either of the enzymes Fdc1 and/or Pad1, for example enzymes as described herein. The nucleic acid sequences encoding the enzymes may be exogenous, i.e., not naturally occurring in the host cell. In a second aspect of the invention the recombinant host cell, such as a micro-organism, preferably comprises at least one polypeptide which is a Fdc1 enzyme, for example, having an amino acid sequence which is at least 21% identical to SEQ ID NO: 1 and in EC class 4.1.1.—(for example any of SEQ ID NOS: 16, 17, 18, 19, 20, 21, 22, 23, 24, 25 and/or 26); and/or preferably comprises at least one polypeptide which is a Pad1 enzyme, for example, having an amino acid sequence which is at least 17% identical to SEQ ID NO: 2 and in EC class 4.1.1.—(for example, any of SEQ ID NOS: 27, 28, 29, 30, 31, 32, 33, 34, 35, 36, and/or 37), or a functional variant or fragment of any of these sequences. For example, the recombinant host cell may comprise a polynucleotide encoding a polypeptide which is at least 21% identical to SEQ ID NO: 1 or encoding a polypeptide which is at least 17% identical to SEQ ID NO: 2, or a functional variant or fragment of either of these. The polynucleotide may, therefore, comprise at least one of the polynucleotide sequences SEQ ID NOS: 3, 4, 5, 6 and/or 7 and/or 38, 39, 40, 41, 42, 43, 44, 45, 46, 47, 48, 49, 50, 51, 52, 53, 54, 55, 56, 57, 58 and/or 59. In one embodiment, the recombinant host cell comprises a polypeptide comprising an amino acid sequence which is at least 21% identical to SEQ ID NO: 1 (for example, selected from the sequences specified in Table 4 herein, such as SEQ ID NOS: 1 and 16, 17, 18, 19, 20, 21, 22, 23, 24, 25 and 26) and a polypeptide comprising an amino acid sequence which is at least 17% identical to SEQ ID NO: 2 (for example, selected from the sequences specified in Table 5 herein, such as SEQ ID NOS:2 and 27, 28, 29, 30, 31, 32, 33, 34, 35, 36 and 37). The recombinant host cell may comprise a polypeptide comprising both of SEQ ID NOS: 1 and 2 and/or an amino acid sequence at least 21% identical to SEQ ID NO: 1 (e.g., any of the sequences in Table 4, such as SEQ ID NOS: 16, 17, 18, 19, 20, 21, 22, 23, 24, 25 or 26) and an amino acid sequence at least 17% identical to SEQ ID NO: 2 (e.g., any of the sequences in Table 5, such as SEQ ID NOS: 27, 28, 29, 30, 31, 32, 33, 34, 35, 36 or 37). Such a polypeptide may be, for example, a fusion protein. In exemplary embodiments, the recombinant host cell may comprise one or more of the polynucleotide sequences SEQ ID NOS: 3, 4, 5, 6 and/or 7. In other embodiments, the recombinant host cell may comprise one or more of the polynucleotide sequences SEQ ID NOS: 38, 39, 40, 41, 42, 43, 44, 45, 46, 47, 48, 49, 50, 51, 52, 53, 54, 55, 56, 57, 58 and/or 59.

In a third aspect of the invention, a suitable polynucleotide may preferably be introduced into the cell by homologous recombination and/or may form part of an expression vector comprising at least one of the polynucleotide sequences SEQ ID NOS: 3, 4, 5, 6 and/or 7 (or SEQ ID NOS: 38, 39, 40, 41, 42, 43, 44, 45, 46, 47, 48, 49, 50, 51, 52, 53, 54, 55, 56, 57, 58 and/or 59) or a complement thereof. Suitable vectors for construction of such an expression vector are well known in the art (examples are mentioned above) and may be arranged to comprise the polynucleotide operably linked to one or more expression control sequences, so as to be useful to express the required enzymes in a host cell, for example a micro-organism as described above.

In some embodiments, the recombinant or genetically modified host cell, as mentioned throughout this specification, may be any micro-organism or part of a micro-organism selected from the group consisting of fungi (such as members of the genus *Saccharomyces*), protists, algae, bacteria (including cyanobacteria) and archaea. The bacterium may comprise a gram-positive bacterium or a gram-negative bacterium and/or may be selected from the genera *Escherichia, Bacillus, Lactobacillus, Rhodococcus, Pseudomonas* or *Streptomyces*. The cyanobacterium may be selected from the group of *Synechococcus elongatus, Synechocystis, Prochlorococcus marinus, Anabaena variabilis, Nostoc punctiforme, Gloeobacter violaceus, Cyanothece* sp. and *Synechococcus* sp. The selection of a suitable micro-organism (or other expression system) is within the routine capabilities of the skilled person. Particularly suitable micro-organisms include *Escherichia coli* and *Saccharomyces cerevisiae*, for example.

In another embodiment, a Fdc1 and/or Pad1 polypeptide or functional variant or fragment of either of these may be expressed in a non-micro-organism cell such as a cultured mammalian cell or a plant cell or an insect cell. Mammalian cells may include CHO cells, COS cells, VERO cells, BHK cells, HeLa cells, Cvl cells, MDCK cells, 293 cells, 3T3 cells, and/or PC12 cells.

The recombinant host cell or micro-organism may be used to express the enzymes mentioned above and a cell-free extract then obtained by standard methods, for use in the method according to the first aspect of the invention.

Embodiments of the present invention also include variants of the polypeptides as defined herein. As used herein, a "variant" means a polypeptide in which the amino acid sequence differs from the base sequence from which it is derived in that one or more amino acids within the sequence are substituted for other amino acids. For example, a variant of SEQ ID NO: 1 has similar or identical ferulic acid decarboxylase characteristics as SEQ ID NO: 1, being classified in enzyme class EC 4.1.1.—by the Enzyme Nomenclature of NC-IUBMB as mentioned above. It may have an amino acid sequence at least about 21% identical to SEQ ID NO: 1, for example, at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% or about 100% identical. Suitable variants may include the proteins listed in Table 4, with particular examples being any of SEQ ID NOS: 16-26. The variants are functional variants in that the variant sequence has similar or, preferably, identical functional enzyme activity characteristics to the enzyme having the non-variant amino acid sequence specified herein (and this is the meaning of the term "functional variant" as used throughout this specification). The similar or identical ferulic acid decarboxylase characteristics as SEQ ID NO: 1, mentioned above, may be assessed, for example, by comparing the rate of conversion of cinnamic acid to styrene by a variant (in the presence of SEQ ID NO: 2) to the rate achieved by SEQ ID NO: 1 in the presence of SEQ ID NO: 2. For a functional variant, this rate may be the same or similar, for example at least about 60%, 70%, 80%, 90% or 95% the rate achieved by SEQ ID NO: 1 (*S. cerevisiae* Fdc1 protein).

Likewise, a variant of SEQ ID NO: 2 has similar or identical phenacrylate decarboxylase characteristics as SEQ ID NO: 2 and is classified in enzyme class EC 4.1.1.—. It may have an amino acid sequence at least about 17% identical to SEQ ID NO: 2, for example, at least about 20%, 25%, 30%, 35%, 37%, 40%, 45%, 50%, 55%, 60%, 65%, 70%, 75%, 80%, 85%, 90%, 91%, 92%, 93%, 94%, 95%, 96%, 97%, 98%, 99% or about 100% identical. Suitable variants may include the proteins listed in Table 5, with particular examples being any of SEQ ID NOS: 27-37. Again, the activity of a variant of SEQ ID NO: 2 may be determined by measuring the rate of conversion of cinnamic acid to styrene by a variant (in the presence of SEQ ID NO: 1) to the rate achieved by SEQ ID NO: 2 in the presence of SEQ ID NO: 1.

Amino acid substitutions may be regarded as "conservative" where an amino acid is replaced with a different amino acid with broadly similar properties. Non-conservative substitutions are where amino acids are replaced with amino acids of a different type.

By "conservative substitution" is meant the substitution of an amino acid by another amino acid of the same class, in which the classes are defined as follows:

| Class | Amino acid examples |
|---|---|
| Nonpolar: | A, V, L, I, P, M, F, W |
| Uncharged polar: | G, S, T, C, Y, N, Q |
| Acidic: | D, E |
| Basic: | K, R, H. |

As is well known to those skilled in the art, altering the primary structure of a polypeptide by a conservative substitution may not significantly alter the activity of that polypeptide because the side-chain of the amino acid which is inserted into the sequence may be able to form similar bonds and contacts as the side chain of the amino acid which has been substituted out. This is so even when the substitution is in a region which is critical in determining the polypeptide's conformation.

In the present invention, non-conservative substitutions are possible provided that these do not interrupt the enzyme activities of the polypeptides, as defined elsewhere herein.

Broadly speaking, fewer non-conservative substitutions than conservative substitutions will be possible without altering the biological activity of the polypeptides. Determination of the effect of any substitution (and, indeed, of any amino acid deletion or insertion) is wholly within the routine capabilities of the skilled person, who can readily determine whether a variant polypeptide retains the enzyme activity according to the invention, as discussed above. For example, when determining whether a variant of the polypeptide falls within the scope of the invention (i.e., is a "functional variant or fragment" as defined above), the skilled person will determine whether the variant or fragment retains the substrate converting enzyme activity which is at least about 60%, preferably at least about 70%, more preferably at least about 80%, yet more preferably about 90%, about 95%, about 96%, about 97%, about 98%, about 99% or about 100% the activity of the non-variant polypeptide. In some cases, the variant may have enzyme activity which is greater than 100% the activity of the non-variant polypeptide, i.e., the variant may have improved enzyme activity compared to the non-variant and increase the rate of conversion of the substrate relevant to the particular enzyme compared to the rate achieved by the non-variant under the same conditions (e.g., substrate concentration, temperature). All such variants are within the scope of the invention.

Using the standard genetic code, further nucleic acid sequences encoding the polypeptides may readily be conceived and manufactured by the skilled person, in addition to those disclosed herein. The nucleic acid sequence may be DNA or RNA and, where it is a DNA molecule, it may for example comprise a cDNA or genomic DNA. The nucleic acid may be contained within an expression vector, as described elsewhere herein.

Embodiments of the invention, therefore, encompass variant nucleic acid sequences encoding the polypeptides of the invention. The term "variant" in relation to a nucleic acid sequence means any substitution of, variation of, modification of, replacement of, deletion of, or addition of one or more nucleic acid(s) from or to a polynucleotide sequence, providing the resultant polypeptide sequence encoded by the polynucleotide exhibits at least the same or similar enzymatic properties as the polypeptide encoded by the basic sequence. The term therefore includes allelic variants and also includes a polynucleotide (a "probe sequence") which substantially hybridises to the polynucleotide sequence of the present invention. Such hybridisation may occur at or between low and high stringency conditions. In general terms, low stringency conditions can be defined as hybridisation in which the washing step takes place in a 0.330-0.825 M NaCl buffer solution at a temperature of about 40-48° C. below the calculated or actual melting temperature ($T_m$) of the probe sequence (for example, about ambient laboratory temperature to about 55° C.), while high stringency conditions involve a wash in a 0.0165-0.0330 M NaCl buffer solution at a temperature of about 5-10° C. below the calculated or actual $T_m$ of the probe sequence (for example, about 65° C.). The buffer solution may, for example, be SSC buffer (0.15M NaCl and 0.015M tri-sodium citrate), with the low stringency wash taking place in 3×SSC buffer and the high stringency wash taking place in 0.1×SSC buffer. Steps involved in hybridisation of nucleic acid sequences have been described for example in Sambrook et al. (10).

Suitably, nucleic acid sequence variants have about 55% or more of the nucleotides in common with the nucleic acid sequence of the present invention, more suitably 60%, 65%, 70%, 80%, 85%, or even 90%, 95%, 98% or 99% or greater sequence identity.

Variant nucleic acids of the invention may be codon-optimised for expression in a particular host cell.

Sequence identity between amino acid sequences can be determined by comparing an alignment of the sequences using the Needleman-Wunsch Global Sequence Alignment Tool available from the National Center for Biotechnology Information (NCBI), Bethesda, Md., USA, for example via http://blast.ncbi.nlm.nih.gov/Blast.cgi, using default parameter settings (for protein alignment, Gap costs Existence:11 Extension:1). Sequence comparisons and percentage identities mentioned in this specification have been determined using this software. When comparing the level of sequence identity to, for example, SEQ ID NO: 1, this suitably can be done relative to the whole length of SEQ ID NO: 1 (i.e., a global alignment method is used), to avoid short regions of high identity overlap resulting in a high overall assessment of identity. For example, a short polypeptide fragment having, for example, five amino acids might have a 100% identical sequence to a five amino acid region within the whole of SEQ ID NO: 1, but this does not provide a 100% amino acid identity according to the present definitions, unless the fragment forms part of a longer sequence which also has identical amino acids at other positions equivalent to positions in SEQ ID NO: 1. When an equivalent position in the compared sequences is occupied by the same amino acid, then the molecules are identical at that position. Scoring an alignment as a percentage of identity is a function of the number of identical amino acids at positions shared by the compared sequences. When comparing sequences, optimal alignments may require gaps to be introduced into one or more of the sequences, to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties. As mentioned above, the percentage sequence identity may be determined using the Needleman-Wunsch Global Sequence Alignment tool, using default parameter settings. The Needleman-Wunsch algorithm was published in J. Mol. Biol. (1970) vol. 48:443-53.

Polypeptide and polynucleotide sequences for use in the methods, vectors and host cells according to the invention are shown in the Sequence Listing and in Tables 4 and 5.

According to a fourth aspect of the invention, there is provided a method of producing an alkane, comprising hydrogenation of an isolated alkene produced in a method according to the first aspect of the invention.

In a preferred embodiment the present invention therefore provides a method for producing an alkane comprising or consisting of:

a) contacting one or more aliphatic unsaturated carboxylic acid(s), preferably comprising at least one α,β-mono-unsaturated alkenoic acid, with an Fdc1 polypeptide comprising an amino acid sequence with at least 21% sequence identity to SEQ ID NO: 1 and a Pad1 polypeptide comprising an amino acid sequence with at least 17% sequence identity to SEQ ID NO: 2 to produce one or more alkene(s), preferably comprising at least one terminal mono-unsaturated alkene;

b) isolating the one or more alkene(s), preferably comprising at least one terminal mono-unsaturated alkene to produce one or more isolated alkene(s), preferably comprising at least one isolated terminal mono-unsaturated alkene;

c) hydrogenating the one or more isolated alkene(s), preferably comprising at least one isolated terminal mono-unsaturated alkene, to produce one or more alkane(s).

Preferences for steps a) and b) are as described above for the first, second and third aspect of the invention.

The unsaturated bonds in the isolated alkene can be hydrogenated to produce the alkane. The hydrogenation may be carried out in any manner known by the person skilled in the art to be suitable for hydrogenation of unsaturated compounds. The hydrogenation catalyst can be any type of hydrogenation catalyst known by the person skilled in the art to be suitable for this purpose. The hydrogenation catalyst may comprise one or more hydrogenation metal(s), for example, supported on a catalyst support. The one or more hydrogenation metal(s) may be chosen from Group VIII and/or Group VIB of the Periodic Table of Elements. The hydrogenation metal may be present in many forms; for example, it may be present as a mixture, alloy or organometallic compound. The one or more hydrogenation metal(s) may be chosen from the group consisting of Nickel (Ni), Molybdenum (Mo), Tungsten (W), Cobalt (Co) and mixtures thereof. The catalyst support may comprise a refractory oxide or mixtures thereof, for example, alumina, amorphous silica-alumina, titania, silica, ceria, zirconia; or it may comprise an inert component such as carbon or silicon carbide.

The temperature for hydrogenation may range from, for example, 300° C. to 450° C., for example, from 300° C. to 350° C. The pressure may range from, for example, 50 bar absolute to 100 bar absolute, for example, 60 bar absolute to 80 bar absolute.

A fifth aspect of the invention provides a method of producing a branched alkane, comprising hydroisomerization of an isolated alkene produced in a method according to the first aspect of the invention, or an alkane produced in a method according to the fourth aspect of the invention. Hydroisomerization may be carried out in any manner known by the person skilled in the art to be suitable for hydroisomerization of alkanes. The hydroisomerization catalyst can be any type of hydroisomerization catalyst known by the person skilled in the art to be suitable for this purpose. The one or more hydrogenation metal(s) may be chosen from Group VIII and/or Group VIB of the Periodic Table of Elements. The hydrogenation metal may be present in many forms, for example it may be present as a mixture, alloy or organometallic compound. The one or more hydrogenation metal(s) may be chosen from the group consisting of Nickel (Ni), Molybdenum (Mo), Tungsten (W), Cobalt (Co) and mixtures thereof. The catalyst support may comprise a refractory oxide, a zeolite, or mixtures thereof. Examples of catalyst supports include alumina, amorphous silica-alumina, titania, silica, ceria, zirconia; and zeolite Y, zeolite beta, ZSM-5, ZSM-12, ZSM-22, ZSM-23, ZSM-48, SAPO-11, SAPO-41, and ferrierite.

Hydroisomerization may be carried out at a temperature in the range of, for example, from 280 to 450° C. and a total pressure in the range of, for example, from 20 to 160 bar (absolute).

In one embodiment, hydrogenation and hydroisomerization are carried out simultaneously.

A sixth aspect of the invention provides a method for the production of a biofuel and/or a biochemical comprising combining an alkene produced in a method according to the first aspect of the invention with one or more additional components to produce a biofuel and/or biochemical.

According to a seventh aspect of the invention, there is provided a method for the production of a biofuel and/or a biochemical comprising combining an alkane produced according to the fourth or fifth aspects of the invention with one or more additional components to produce a biofuel and/or biochemical.

In the sixth and seventh aspects, the alkane and/or alkene can be blended as a biofuel component and/or a biochemical component with one or more other components to produce a biofuel and/or a biochemical. By a biofuel or a biochemical, respectively, is herein understood a fuel or a chemical that is at least partly derived from a renewable energy source. Examples of one or more other components with which alkane and/or alkene may be blended include anti-oxidants, corrosion inhibitors, ashless detergents, dehazers, dyes, lubricity improvers and/or mineral fuel components, but also conventional petroleum derived gasoline, diesel and/or kerosene fractions.

A further aspect of the invention provides the use of a host cell according to the second aspect of the invention as a biofuel/biochemical hydrocarbon precursor source. A "biofuel/biochemical hydrocarbon precursor" is a hydrocarbon, suitably an alkene or mixture of alkenes, which may be used in the preparation of a biofuel and/or a biochemical, for example in a method according to the sixth or seventh aspects of the invention. The use of a host cell as the source of such a precursor indicates that the host cell according to the second aspect of the invention produces hydrocarbons suitable for use in the biofuel/biochemical production methods, the hydrocarbons being isolatable from the recombinant host cell as described elsewhere herein.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

Figure 2A:
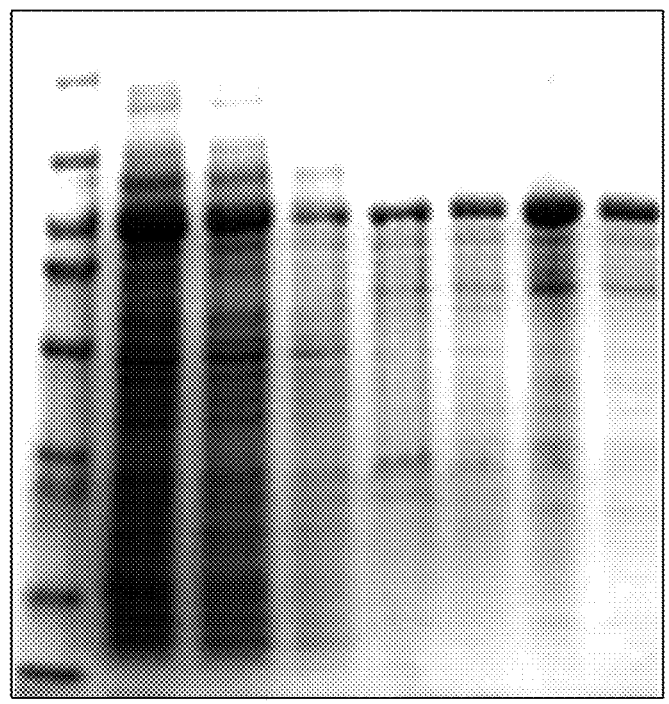
FIGS. 2A and 2B show heterologous expression of a Pad1-TF fusion protein.
Figure 2B:
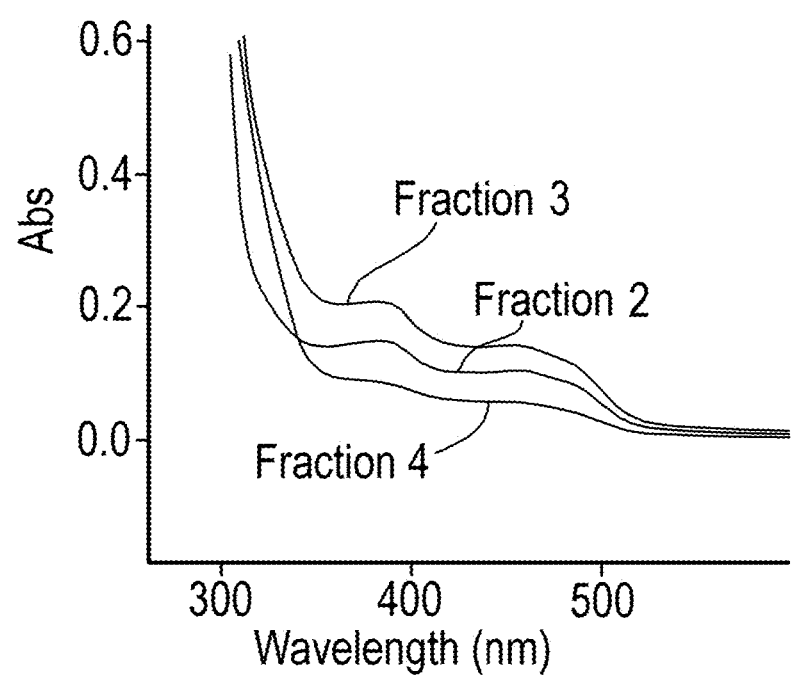
Figure 3:
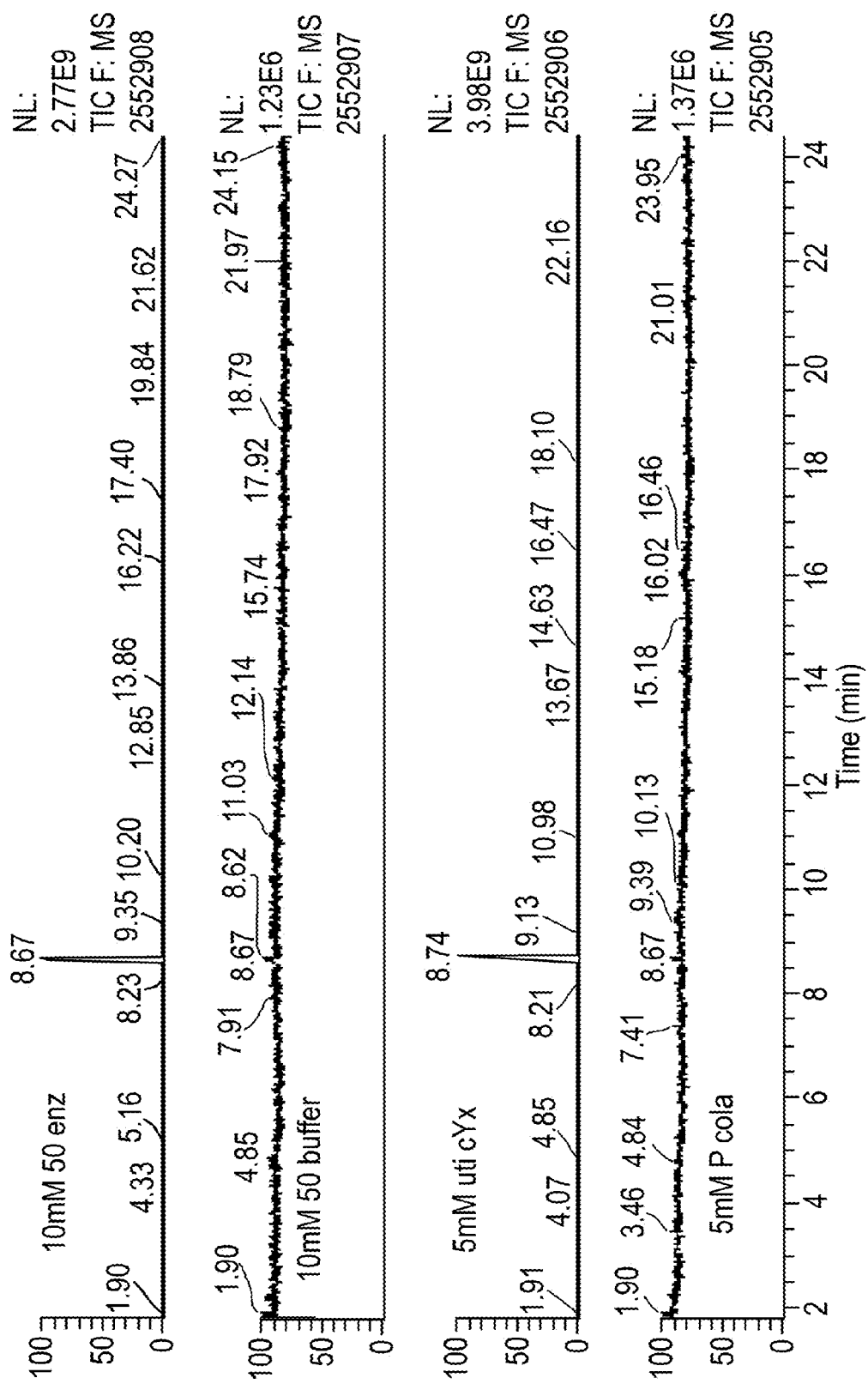
FIG. 3 shows GC-MS analysis of headspace samples from cells expressing Fdc1/Pad1.
Figure 5A:
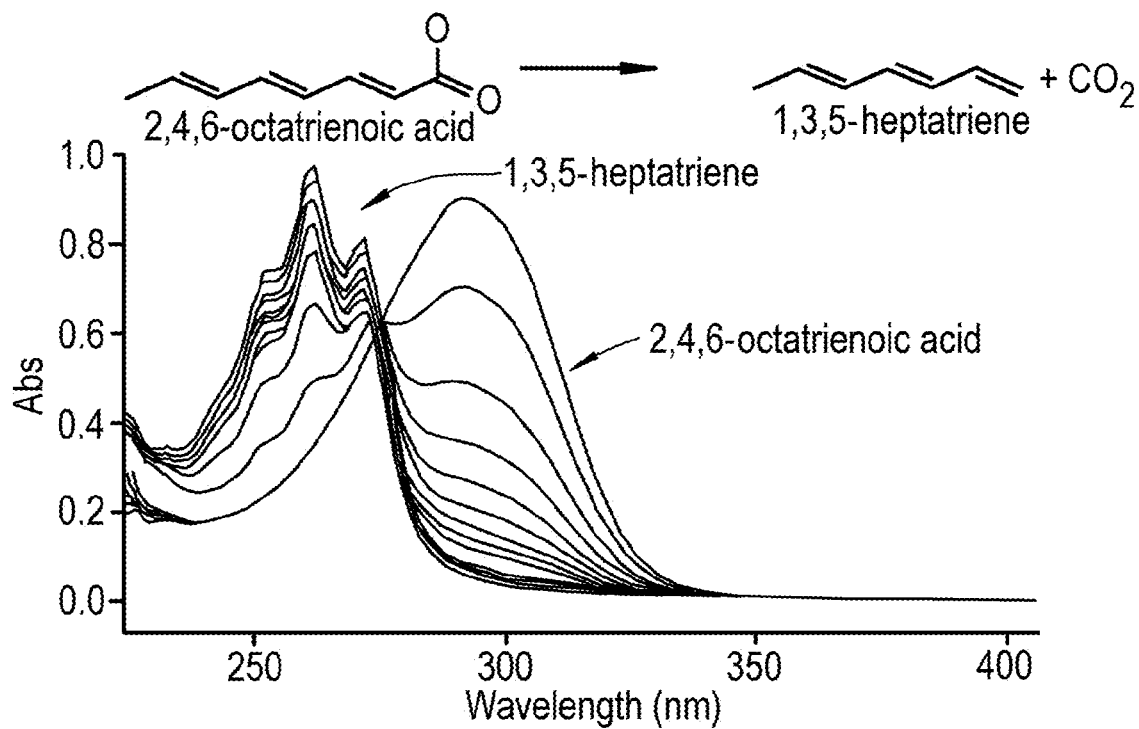
FIGS. 5A and 5B show direct monitoring of enzyme reactivity using UV-VIS spectroscopy.
Figure 5B:
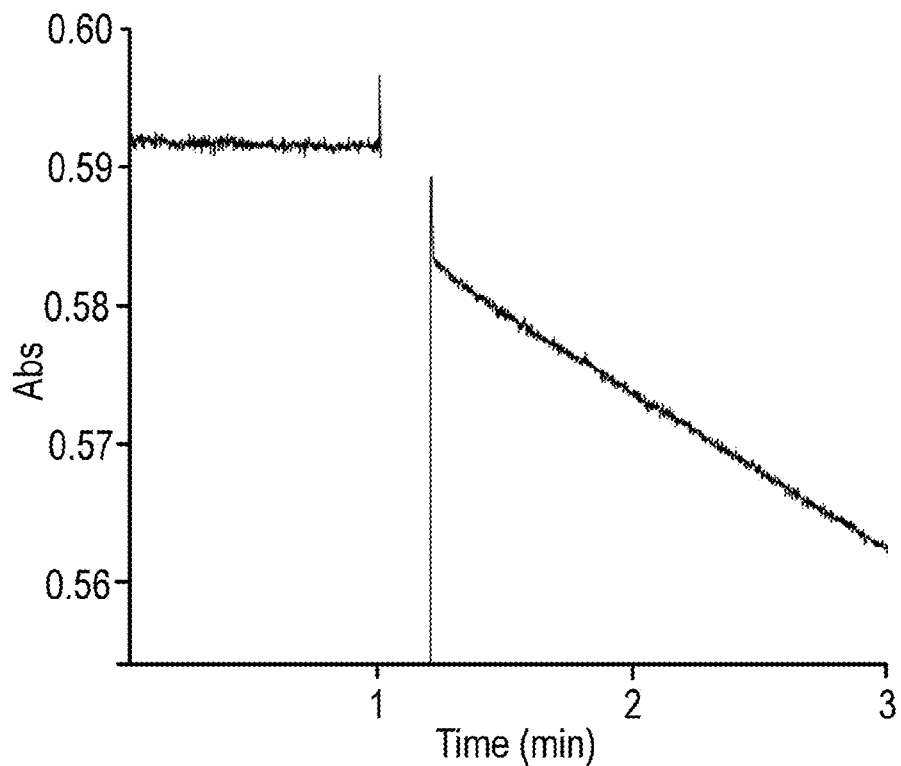

Embodiments of the invention will now be shown, by way of example only, which is not intended to limit embodiments of the invention, with reference to FIGS. 1-6. In FIG. 1, there is a series of SDS-PAGE gels of protein purification expression trials. For samples containing Fdc1, a band can be readily observed corresponding to the 58 kDa his-tagged Fdc1; in contrast, Pad1 expression levels are very low. FIGS. 2A and 2B show heterologous expression of a Pad1-TF fusion protein. The fusion protein is soluble and can be purified using affinity chromatography; the fusion protein binds flavin, indicative of Pad1 being folded. FIG. 3 shows GC-MS analysis of headspace samples from cells expressing Fdc1/Pad1 (third trace from top) and from pure protein extracts (top trace), confirming styrene production following incubation with cinnamic acid. The second trace from the top is a buffer only sample and the final trace is an empty pCOLAduet plasmid sample. FIG. 4 shows the results of a high-throughput pH-based screening of enzymatic activity of purified Fdc1/Pad1. FIGS. 5A and 5B show direct monitoring of enzyme reactivity using UV-VIS spectroscopy. FIG. 5A shows the enzyme catalysed conversion of octotrienoic acid monitored over a 230-400 nm range. FIG. 5B shows the linear decrease in absorbance at a single wavelength observed following enzyme addition. FIGS. 6A and 6B show 1-pentene identification by GC-MS, indicating enzyme-catalysed production of 1-pentene from 2-hexenoic acid (FIG. 6A) compared to an enzyme-free control (FIG. 6B).

EXAMPLES

Unless indicated otherwise any solutions and/or concentrations are in distilled water.
Heterologous Expression
fdc1 gene and pad1 gene were codon optimised for expression in *E. coli* and synthesised as detailed within this text. The codon optimized fdc1 and pad1 genes were both cloned into a pCOLAduet-1 vector (commercially available from Merck Millipore) using polymerase chain reaction (PCR), to ensure high expression of both subunits of the enzyme. The pCOLADuet-1 vector carries the COLA replicon, lad gene and kanamycin resistance gene. Primers were used to complement the codon optimised gene sequences. The fdc1 and pad1 genes were cloned using In-fusion Advantage PCR Cloning Kit (commercially obtained from Clontech, In-fusion is a trademark). The primers used were as shown in Table 1 below.

TABLE 1

Primers

| Primer | Sequence | SEQ ID NO: |
|---|---|---|
| pad1F SacI | 5'-GGATCCGAATTCGAGCTCGATGCTGCTGTTCCCGC GTCGC-3' | 8 |
| pad1R AflII | 5'-TTCTGTTCGACTTAAGCTATTTGCTTTTGATACCT TCCCAGCGCGG-3' | 9 |
| pad1F NdeI | 5'-GAAGGAGATATACATATGCTGCTGTTCCCGCGTCG CACC-3' | 10 |
| pad1R XhoI | 5'-CTTTACCAGACTCGAGCTATTTGCTTTTGATACCT TCCCAGCGCGG-3' | 11 |
| fdc1F SacI | 5'-CAGGATCCGAATTCGAGCTCGATGCGCAAACTGAA CCCGGCTC-3' | 12 |
| fdc1R AflII | 5'-TTCTGTTCGACTTAAGCTATTTGTAACCATAGCGT CAGTT-3' | 13 |

Versions of yeast fdc1 gene (genbank accession number NM_001180847.1) and yeast pad1 gene (genbank accession number NM_001180846) that were codon optimized for expression in *E. coli* (SEQ ID NOS: 3 & 4, respectively) were commercially obtained from GenScript and provided in pUC57 constructs.

For expression of each enzyme individually the fdc1 gene and pad1 gene respectively were amplified from the pUC57 constructs by polymerase chain reaction (PCR) using a Pfu Ultra II fusion HS DNA polymerase (commercially obtainable from Agilent). Template was removed by DpnI (*Diplococcus pneumonia* nuclease-I) digestion (commercially obtainable from New England Biolabs) and the gene was cloned into the SacI/AflII sites of Multiple Cloning Site 1 (MCS1) in a pCOLAduet-1 vector (commercially available from Merck Millipore) using an In-fusion Advantage PCR Cloning Kit as described below (commercially obtained from Clontech, In-fusion is a trademark).

For expression of each enzyme individually the fdc1 gene and pad1 gene respectively were individually cloned into the SacI/AflII sites of Multiple Cloning Site 1 (MCS1) in the pCOLAduet-1 vector (commercially available from Merck Millipore). For co-expression of both genes, fdc1 gene was cloned into the SacI/AflII sites of MCS1 first and then pad1 gene was cloned into the NdeI/XhoI sites of Multiple Cloning Site 2 (MCS2) of the pCOLAduet-1 vector.

To clone into the pCOLAduet-1 vector (also sometimes referred to as expression vector), the pCOLAduet-1 vector was linearized by digestion with the two relevant restriction enzymes (i.e. SacI/AflII respectively NdeI/XhoI), and both the PCR product and the linearized pCOLAduet-1 vector were purified using a Qiaquick PCR purification kit (commercially obtainable from Qiagen). The purified PCR product and purified linearized pCOLAduet-1 vector were added in a 2:1 ratio (of PCR product to vector) to 2 ml of the 5× In-fusion buffer and 1 ml In-fusion enzyme in a 10 ml reaction volume (obtained from the In-fusion Advantage PCR Cloning Kit, Clontech). The reaction was incubated at 37° C. for 15 minutes, followed by 15 minutes at 50° C. Hereafter the reaction mixture was diluted to 50 mL with a 10 mM Tris (tris(hydroxymethyl)methylamino)propane)/Cl pH 8.5 buffer and 2.5 ml transformed into 50 ml chemically competent *E. coli* NEB5a (commercially obtainable from New England Biolabs). Plasmid from a number of transformants was purified using a Qiaprep miniprep kit (commercially obtainable from Qiagen). The insertion of the gene into the pCOLAduet-1 vector was confirmed by restriction digest (as described above) and sequencing.

Fdc1 and/or Pad1 polypeptides were expressed in *E. coli* Bl21(DE3) grown at 37° C. in Luria-Bertani (LB) supplemented with 40 μg/ml (microgram/milliliter) kanamycin. At mid-log phase cells were induced with 0.25 mM (millimolair, in distilled water) Isopropyl-β-D-1-thiogalactopyranoside (IPTG) and grown at 25° C. overnight.

To purify Fdc1 and/or Pad1 polypeptides, cell pellets were resuspended in a purification buffer (200 mM NaCl, 50 mM Sodium Phosphate (NaPi) in distilled water, pH 7.5) supplemented with about 1 mg/ml (milligrams/milliliter) hen egg white lysozyme (commercially obtainable from Sigma), 10 μg/ml (micrograms/milliliter) Deoxyribonuclease I (commercially obtainable from Sigma), 10 μg/ml Ribonuclease A (commercially obtainable from Sigma) and complete EDTA free protease inhibitor cocktail (commercially obtainable from Roche). Cells were lysed by French press and about 48384 grams of lysate was centrifuged to produce a supernatant and a pellet residue. Imidazole was added to the clarified supernatant until a 10 mM (millimolair) imidazole final concentration was obtained. Subsequently the imidazole containing supernatant was applied to a 5 ml nickel-nitrilotriacetic (Ni-NTA) agarose (also referred to as $Ni^{2+}$-agarose, commercially obtainable from Qiagen). The column was washed with 3 column volumes of purification buffer supplemented with 10 mM imidazole and consequently another 3 column volumes of purification buffer with 50 mM imidazole, and the polypeptide eluted with 4×1 ml purification buffer containing 250 mM imidazole. Fractions were analysed by SDS-PAGE (Sodium dodecyl-sulphate-polyacrylamide gel electrophoresis) to detect the presence of Fdc1/Pad1 polypeptides. Fractions containing the desired polypeptides were pooled and buffer exchanged into 200 mM NaCl, 50 mM NaPi pH 7.5 using an Econo-Pac 10DG (i.e. comprising 10 ml Bio-GelP-6DG gel) desalting column (BioRad) to remove imidazole.

Analysis of the Fdc1 and/or Pad1 polypeptide yield under a variety of expression conditions/*E. coli* strains revealed that significant amounts of Fdc1 polypeptide can easily be achieved (FIG. 1). In contrast, the Pad1 protein is not visible as a distinct band using SDS-PAGE, indicating low levels of expression. Polypeptide purification of Fdc1 polypeptide (from fdc1 gene containing cells grown with or without the pad1 gene present) is straightforward, giving rise to large amounts of pure Fdc1 polypeptide. The presence of Pad1 polypeptide can be detected, either through western blotting with anti-histidine(His)-tag antibodies, or via direct detection of Pad1 polypeptides following an in-gel tryptic digest (not shown). Pad1 levels were found to be <5% of the corresponding Fdc1 levels.

The inventors have found that Pad1 levels can be increased through fusion of the protein to a trigger factor type chaperone. Cloning and expression of Pad1 trigger factor was achieved using amplification primers:

```
Pad1TFF (SEQ ID NO: 14):
5'-TCGAAGGTAGGCATATGCTGCTGTTCCCGCGTCGCACC-3'

Pad1TFR (SEQ ID NO: 15):
5'-ATTCGGATCCCTCGAGCTATTTGCTTTTGATACCTTCCCAGCGCGG-3'
```

The Pad1 gene was amplified from the codon optimized gene in pUC57 vector by PCR using the Phusion DNA polymerase (NEB) reaction. Template was removed by DpnI digestion and the gene inserted into the NdeI/XhoI sites of linearized pCold TF vector (commercially obtainable from Takara Bio Inc.) using infusion HD cloning kit (commercially obtainable from Clontech). Takara's pColdTF DNA Vector is a fusion cold shock expression vector that expresses Trigger Factor (TF) chaperone as a soluble fusion tag. Trigger Factor is an *E. Coli* originated prokaryotic ribosome-associated chaperone protein (48 kDa). The pCold TF DNA Vector consists of the cspA promoter plus additional downstream sequences including a 5' untranslated region (5' UTR), a translation enhancing element (TEE), a His-Tag sequence, and a multicloning site (MCS). A lac operator is inserted downstream of the cspA promoter to ensure strict regulation of expression. Additionally, recognition sites for HRV 3C Protease, Thrombin and Factor Xa are located between TF-Tag and the MCS and function to facilitate tag removal from the expressed fusion protein.

pad1 pCold TF in *E. coli* Bl21(DE3) was grown in LB broth supplemented with 50 µg/ml ampicillin at 37° C. to $OD_{600}$ of 0.6-0.8. Expression was induced by addition of 0.25 mM ITPG and the cultures grown overnight at 15° C.

Cell pellets were resuspended in purification buffer (400 mM NaCl, 50 mM NaPi pH 7.5) supplemented with lysozyme, DNase, RNase and EDTA free complete protease inhibitor cocktail (Roche). Cells were lysed by French press and the lysate centrifuged. The clarified supernatant was supplemented with 10 mM imidazole and applied to a 5 ml $Ni^{2+}$-agarose (Qiagen). The column was washed with 3 column volumes of purification buffer supplemented with 10 mM imidazole and consequently another 3 column volumes of purification buffer with 50 mM imidazole, and the protein eluted with 4×1 ml purification buffer supplemented with 250 mM imidazole. Fractions were analysed by SDS-PAGE to confirm the presence of trigger factor-Pad1 fusion protein (FIG. 2A).

Enzyme Activity Studies

In vivo enzyme activity assays were carried out using exogenous supplied substrates in the media (i.e. sorbic acid). Significant enzyme activity leaded to a measurable pH increase (alkalinification through $CO_2$ release and $H^+$ take-up).

For in vivo pH assays, LB agar plates were supplemented with 40 mg/ml kanamycin, 6 mM sorbic acid and 0.004% w/v phenol red in distilled water and buffered to pH 6.2. *E. coli* Bl21(DE3) cells containing either the co-expression plasmid or empty pCOLAduet-1 were inoculated onto the plate and grown overnight at 37° C. Using phenol red as a pH indicator, the inventors could establish that substrate dependent alkalinification in vivo (i.e., yellow to red colour change observed) is clearly linked to the presence of the fdc1/pad1 genes. This allows rapid visual indication of enzyme activity levels.

For in vitro pH assays, the activity of purified His-Fdc1/Pad1 was assayed in 96 well plates containing 200 µl 50 mM KCl, 0.06-1 mM Hepes (4-(2-hydroxyethyl)-1-piperazineethanesulfonic acid), 0.002% Phenol red and 0-50 mM substrate pH 6.8. Rates of alkalinification were followed by the increase in Absorbance at 560 nm wavelength ($A_{560}$) using a synergy High throughput (HT)plate reader (commercially obtainable from BioTek).

Following positive indication of in vitro enzyme activity, direct product analysis of volatile alkenes was performed using head space Gas Chromatography-Mass Spectrometry (GC-MS) analysis. For in vivo analysis, fdc1/pad1 in pCOLAduet and empty pCOLAduet in *E. coli* Bl21(DE3) were grown in LB supplemented with 40 µg/ml kanamycin at 37° C. to an $OD_{600}$ of about 0.7 and induced with 0.25 mM IPTG. 11.5 ml induced culture and a solution of 3.5 ml 20 mM substrate in distilled water with a pH of about 7.5 were placed in 20 ml head space vials with crimp top seals. Cultures were incubated in shaking incubator at 25° C. for about 12-48 hours.

For in vitro analysis, purified His-Fdc1/Pad1 polypeptide was buffer exchanged into a solution of 150 mM NaCl and 50 mM NaPi in water with pH 7.5. Subsequently solutions of 11.5 ml 150 mM NaCl and 50 mM NaPi with pH 7.5, of 3.5 ml 20 mM substrate with pH 7.5 and of 150 µl 30 mg/ml enzyme in water or buffer were added to 20 ml head space vials with crimp top seals. Reactions were incubated with shaking at 25° C. for about 12-48 hours.

Samples were analysed by GC-MS using a Thermofisher DSQ II. Vials were incubated for 3 minutes at 80° C. with agitation. 0.5 ml headspace was injected with a 105° C. syringe and a split ratio of 1/10. Analytes were separated on a 30 m 0.25 mm 0.25µ ZB5-MS (commercially obtainable from Zebron) column run (alternatively a 30 m×0.25 mm i.d.×0.1µ Varian VF-5HT column may be used) with a flow of 1.5 ml/min He. Oven temperature was held at 35° C. for 2 minutes before being ramped up to 250° C. at 10° C./min. Products were identified by searching for the corresponding mass peak.

These GC-MS studies verified the presence of the anticipated decarboxylation products of sorbic acid, cinnamic acid and ferulic acid (i.e. 1,3-pentadiene, styrene and 4-vinylguaiacol) using in vivo enzymatic conversions (FIG. 3).

The inventors then turned to purification and in vitro assaying of enzyme activity. Using standard Ni-affinity chromatography purification (where needed combined with gel-filtration), Fdc1(/Pad1) can easily be purified. Unfortunately, Pad1 levels are <5% of Fdc1 level (FIG. 1). The (indirect) enzyme activity pH-test used for in vivo studies is easily extended to in vitro-studies on purified protein (FIG. 4). In this case, purified Fdc1(/Pad1) was shown to lead to substrate dependent alkalinification of a range of substrates in absence of any externally added cofactors.

A direct observation of enzyme activity is possible by recording UV-VIS spectra of the solution. Aromatic substrates and aliphatic substrates with two or more double bonds conjugated to the acidic group absorb in the UV region. The activity of purified His-Fdc1/Pad1 was assayed against varying concentrations of these substrates in 400 µl 50 mM KCl, 50 mM NaPi pH 6 in a 1 mm pathlength cuvette at 20° C. Substrate consumption was monitored using a Cary 50 Bio spectrophotometer (varian) either in scanning mode, or at a specific wavelength for kinetic experiments. The rate of cinnamic acid consumption was monitored at 270 nm, ferulic acid at 312 nm, 2,4-pentadienoic acid at 242 nm, sorbic acid at 260 nm, 2,4,6-octatrienoic acid at 290 nm and 2,4-nonadienoic acid at 260 nm.

Most substrates displayed a spectrum distinct from the corresponding products. Enzyme dependent spectral changes can easily be monitored over time, and have confirmed the activity of the enzyme with a wide range of enolate-type substrates (FIG. 5). This is, at present, the most rigorous and efficient method for enzyme activity studies.

Finally, GC-MS product analysis (see above) has confirmed product formation using in vitro methods for standard substrates sorbic acid, cinnamic acid and ferulic acid (i.e. 1,3-pentadiene, styrene and 4-vinylguaiacol; FIG. 3). The UV-vis method was used to assess Michaelis Menten parameters for a variety of substrates (sorbic acid, cinnamic acid, ferulic acid, octatrienoic acid), most of which have a $K_M$ in the sub-mM range (see Table 2 below).

Mechanistic Studies of Fdc1/Pad1

The data herein points to Fdc1 being responsible for catalysis, with the role of Pad1 remaining unclear. Nevertheless, specific activity of Fdc1 is significantly higher when Pad1 is present in the solution/cell, albeit at sub-stoichiometric levels.

Fdc1/Pad1 Substrate Range

To assess what limit the enzyme imposes on the extent of unsaturation, the inventors tested a wide range of saturated and unsaturated substrates, both in vivo and in vitro. Under no conditions was decarboxylation with saturated fatty acids observed and the enzyme clearly does not support alkane production. However, mono-unsaturated acids (mono unsaturated alkenoic acids) were found to give rise to corresponding α-olefine (terminal alkene) compounds. The activity observed with the latter compounds could only be detected following prolonged incubation with high enzyme concentrations and using product detection, as follows.

GC-MS Detection of Terminal Alkenes

As described above, for in vivo studies, Fdc1/Pad1 in pCOLAduet-1 and empty pCOLAduet-1 vector were transformed into E. coli Bl21(DE3). Cultures were grown in LB supplemented with 40 µg/ml kanamycin at 37° C. to $OD_{600}$~0.7 and induced with 1 mM IPTG. 11.5 ml of induced culture was added to 3.5 ml 20 mM substrate pH ~7.5 per tube in a sealed headspace vial.

For in vitro reactions, Fdc1/Pad1 partially purified by $Ni^{2+}$ affinity and buffer exchanged into 150 mM NaCl, 50 mM NaPi pH 7.5. 11.5 ml 300 mM NaCl, 100 mM NaPi pH 7.5, 3.5 ml 20 mM substrate pH 7.5 and 150 µl 30 mg/ml enzyme or enzyme free buffer were added to a sealed headspace vial.

All Fdc1/Pad1 reactions were incubated in a shaking incubator at 25° C. for ~36 hours.

Samples were analysed by GC-MS using a Thermofisher DSQ II. Vials were incubated for 3 minutes at 80° C. with agitation. 0.5 ml headspace was injected with a 105° C. syringe and a split ratio of 1/10. Analytes were separated on a 30 m 0.25 mm 0.25µ ZB5-MS (or 30 m×0.25 mm i.d.×0.1µ Varian VF-5HT) column run with a flow of 1.5 ml/min He. Oven temperature was held at 35° C. for 2 minutes before being raised to 250° C. at 10° C./min. Products were identified by searching for the corresponding mass peak.

A split ratio of 1/100 was used with aromatic and di/tri-unsaturated aliphatic substrates as the quantities of product produced from these were far higher. FIG. 6 shows that 1-pentene product has been detected with 2-hexenoic acid in vitro; it has also been detected in vivo. Activity with 2-heptenoic and 2-octenoic has so far only been detected in vivo.

In summary, high in vitro and in vivo activity was observed with 2,4-pentadienoic-, sorbic (2,4-Hexadienoic)-, 2,4,6-octatrienoic-, 2,4-nonadienoic-, cinnamic-, and ferulic acids. Lower level activity was observed with 2-hexenoic acid. In vivo activity has also been detected with 2-heptenoic or 2-octenoic acids. No activity was observed for saturated carboxylic acids. Direct identification of 1,3-butadiene, 1,3-pentadiene, 1,3,5-heptatriene, 1,3-octadiene, styrene, 4-vinylguaiacol (3-methoxy-4-vinylphenol), 1-pentene, 1-hexene and 1-heptene products have been observed by GC-MS.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the embodiments of the invention. Changes may be made in the elements described herein without departing from the spirit and scope of the invention as described in the claims.

TABLE 2

| Substrate | Expected product | Activity Detected | | | Kinetics | |
|---|---|---|---|---|---|---|
| | | pH assay | UV-Vis | GC-MS | Km (mM) | Kcat (s⁻¹) |
| A: Aromatic substrates | | | | | | |
| Ferulic acid | 4-vinyl guaiacol | ✓ | ✓ | ✓ | 0.203 (±0.033) | 30.774 (±1.996) |
| Sinapinic acid | 2,6-dimethoxy-4-vinylphenol | | ✓ | | | |
| Cinnamic acid | styrene | ✓ | ✓ | ✓ | 0.021 (±0.003) | 34.394 (±1.206) |
| α-Methyl cinnamic acid | 2-methyl styrene | | ✓ | | | |
| α-Fluoro cinnamic acid | 2-fluoro styrene | | ✓ | | | |
| β-Methyl cinnamic acid | 1-methyl styrene | | ✓ | | | |
| 1,2,3,4,5-Pentafluoro cinnamic acid | 1,2,3,4,5-Pentafluoro styrene | | ✓ | | | |
| 4-Nitro cinnamic acid | 4-nitrostyrene | | ✓ | | | |
| trans-3-Indole acrylic acid | 3-vinylindole | | ✓ | | | |
| B: Aliphatic substrates | | | | | | |
| 2,4-Pentadienoic acid | 1,3-butadiene | ✓ | ✓ | ✓ | 0.109 (±0.044) | 0.336 (±0.049) |
| 2-Hexenoic acid | 1-pentene | x* | | ✓ | | |
| Sorbic acid | 1,3-pentadiene | ✓ | ✓ | ✓ | 0.081 (±0.011) | 2.793 (±0.091) |
| 2-Heptenoic acid | 1-hexene | | | ✓ | | |
| 2-Octenoic acid | 1-heptene | x* | | ✓ | | |
| 2,4,6-Octatrienoic acid | 1,3,5-heptatriene | ✓ | ✓ | ✓ | 0.213 (±0.058) | 99.001 (±9.987) |
| 2,4-Nonadienoic acid | 1,3-octadiene | ✓ | ✓ | ✓ | 0.221 (±0.044) | 0.588 (±0.037) |

*pH assays were non-positive as the method was not sensitive enough to measure the lower levels present.

TABLE 3

Identity of sequences included in application

| SEQ ID NO | Description of sequence |
|---|---|
| 1 | *Saccharomyces cerevisiae* Fdc1 protein |
| 2 | *Saccharomyces cerevisiae* Pad1 protein |
| 3 | Codon-optimised cDNA encoding Fdc1 (SEQ ID NO: 1) |
| 4 | Codon-optimised cDNA encoding Pad1(SEQ ID NO: 2) |
| 5 | *Saccharomyces cerevisiae* DNA encoding Fdc1 and Pad1 |
| 6 | *Saccharomyces cerevisiae* cDNA encoding Fdc1 |
| 7 | *Saccharomyces cerevisiae* DNA encoding Pad1 |
| 8 | Pad1F SacI amplification primer |
| 9 | Pad1R AflII amplification primer |
| 10 | Pad1F XhoI amplification primer |
| 11 | Pad1R SacI amplification primer |
| 12 | Fdc1F SacI amplification primer |
| 13 | Fdc1R AflII amplification primer |
| 14 | Pad1TFF amplification primer |
| 15 | Pad1TFR amplification primer |
| 16 | GenBank accession no. BAG32392.1 *S. cerevisiae* Fdc1 homologue |
| 17 | GenBank accession no. EHN07793.1 *S. cerevisiae* × *S. kudriavzevii* VIN7 Fdc1 homologue |
| 18 | GenBank accession no. EDN60854.1 *S. cerevisiae* Fdc1 homologue |
| 19 | GenBank accession no. EGA83279.1 *S. cerevisiae* Fdc1 homologue |
| 20 | GenBank accession no. EHN02917.1 *S. cerevisiae* × *S. kudriavzevii* VIN7 Fdc1 homologue |
| 21 | GenBank accession no. GAA22747.1 *S. cerevisiae* Kyokai No. 7 Fdc1 homologue |
| 22 | GenBank accession no. XP_461563.1 *Debaryomyces hansenii* CBS767 Fdc1 homologue |
| 23 | GenBank accession no. XP_002499372.1 *Zygosaccharomyces rouxii* Fdc1 homologue |

TABLE 3-continued

Identity of sequences included in application

| SEQ ID NO | Description of sequence |
|---|---|
| 24 | GenBank accession no. XP_002421128.1 *Candida dubliniensis* CD36 Fdc1 homologue |
| 25 | GenBank accession no. EEQ46648.1 *Candida albicans* WO-1 Fdc1 homologue |
| 26 | GenBank accession no. XP_001390534.1 *Aspergillus niger* CBS 513.88 Fdc1 homologue |
| 27 | GenBank accession no. AAA20484.1 *S. cerevisiae* Pad1 homologue |
| 28 | GenBank accession no. EDN60853.1 *S. cerevisiae* YJM789 Pad1 homologue |
| 29 | GenBank accession no. BAG32352.1 *S. cerevisiae* Pad1 homologue |
| 30 | GenBank accession no. BAG32360.1 *S. cerevisiae* Pad1 homologue |
| 31 | GenBank accession no. BAG32371.1 *S. cerevisiae* Pad1 homologue |
| 32 | GenBank accession no. EHN02916.1 *S. cerevisiae* × *S. kudriavzevii* VIN7 Pad1 homologue |
| 33 | GenBank accession no. EGA79325.1 *S. cerevisiae* Vin13 Pad1 homologue |
| 34 | GenBank accession no. XP_461564.2 *Debaryomyces hansenii* CBS767 Pad1 homologue |
| 35 | GenBank accession no. XP_002499371.1 *Zygosaccharomyces rouxii* Pad1 homologue |
| 36 | GenBank accession no. XP_002421129.1 *Candida dubliniensis* CD36 Pad1 homologue |
| 37 | GenBank accession no. EEQ46647.1 *Candida albicans* WO-1 Pad1 homologue |
| 38 | GenBank accession no. AB368818.1 *S. cerevisiae* DNA encoding SEQ ID NO: 16 |
| 39 | GenBank accession no. AGVY01000015.1 *S. cerevisiae* × *S. kudriavzevii* VIN7 DNA encoding SEQ ID NO: 17 |
| 40 | GenBank accession no. AAFW02000145.1 *S. cerevisiae* YJM789 DNA encoding SEQ ID NO: 18 |
| 41 | GenBank accession no. ADVV01000025.1 *S. cerevisiae* DNA encoding SEQ ID NO: 19 |
| 42 | GenBank accession no. AGVY01000185.1 *S. cerevisiae* × *S. kudriavzevii* VIN7 DNA encoding SEQ ID NO: 20 |
| 43 | GenBank gi|34956838 *S. cerevisiae* Kyokai No. 7 DNA encoding SEQ ID NO: 21 |
| 44 | GenBank accession no. XM_461563.1 *Debaryomyces hansenii* CBS767 mRNA encoding SEQ ID NO: 22 |
| 45 | GenBank accession no. XM_002499327.1 *Zygosaccharomyces rouxii* mRNA encoding SEQ ID NO: 23 |
| 46 | GenBank accession no. XM_002421083.1 *Candida dubliniensis* CD36 mRNA encoding SEQ ID NO: 24 |
| 47 | GenBank accession no. CM000312.1 *Candida albicans* DNA encoding SEQ ID NO: 25 |
| 48 | GenBank accession no. XM_001390497.1 *Aspergillus niger* CBS 513.88 mRNA encoding SEQ ID NO: 26 |
| 49 | GenBank accession no. L09263.1 *S. cerevisiae* DNA encoding SEQ ID NO: 27 |
| 50 | GenBank accession no. AAFW02000145.1 *S. cerevisiae* YJM789 DNA encoding SEQ ID NO: 28 |
| 51 | GenBank accession no. AB368778.1 *S. cerevisiae* DNA encoding SEQ ID NO: 29 |
| 52 | GenBank accession no. AB368786.1 *S. cerevisiae* DNA encoding SEQ ID NO: 30 |
| 53 | GenBank accession no. AB368797.1 *S. cerevisiae* DNA encoding SEQ ID NO: 31 |
| 54 | GenBank accession no. AGVY01000185.1 *S. cerevisiae* × *S. kudriavzevii* VIN7 DNA encoding SEQ ID NO: 32 |
| 55 | GenBank accession no. ADXC01000024.1 *S. cerevisiae* Vin13 DNA encoding SEQ ID NO: 33 |
| 56 | GenBank accession no. XM_461564.2 *Debaryomyces hansenii* CBS767 mRNA encoding SEQ ID NO: 34 |
| 57 | GenBank accession no. XM_002499326.1 *Zygosaccharomyces rouxii* mRNA encoding SEQ ID NO: 35 |
| 58 | GenBank accession no. XM_002421084.1 *Candida dubliniensis* CD36 mRNA encoding SEQ ID NO: 36 |
| 59 | GenBank accession no. CM000312.1 *Candida albicans* WO-1 DNA encoding SEQ ID NO: 37 |

TABLE 4

Fdc1 homologue polypeptides

| GenBank Accession No. | Overall % sequence identity with SEQ no. 1 |
|---|---|
| NP_010828.1 | 100% |
| BAG32392.1 | 99% |
| BAG32381.1 | 99% |
| EHN07793.1 | 99% |
| EDN60854.1 | 99% |
| EGA83279.1 | 99% |
| EHN02917.1 | 89% |
| GAA22747.1 | 68% |
| XP_461563.1 | 60% |
| XP_002499372.1 | 59% |
| XP_002421128.1 | 59% |
| EEQ46648.1 | 59% |
| XP_718068.1 | 58% |
| XP_003195517.1 | 47% |
| XP_002564382.1 | 47% |
| XP_001261424.1 | 47% |
| EFX01410.1 | 47% |
| XP_001818650.1 | 47% |
| EGU80878.1 | 45% |
| EHK48809.1 | 46% |
| XP_001218695.1 | 46% |
| EFZ02049.1 | 46% |
| XP_003195387.1 | 45% |
| GAA90861.1 | 47% |
| CCD33957.1 | 46% |
| EDZ72732.1 | 46% |
| XP_001390534.1 | 46% |
| XP_001545682.1 | 46% |
| EHK20699.1 | 44% |
| XP_003039530.1 | 44% |
| EGU86506.1 | 43% |
| EHK46069.1 | 42% |
| EFX01795.1 | 43% |
| XP_384845.1 | 41% |
| EFY97969.1 | 41% |
| EDZ72739.1 | 37% |
| XP_003041887.1 | 40% |
| XP_003044170.1 | 40% |
| EGZ23463.1 | 41% |
| XP_386610.1 | 37% |
| AC072979.1 | 37% |
| EGU82090.1 | 42% |
| EHK21882.1 | 40% |
| EHK42408.1 | 38% |
| EFY85845.1 | 39% |
| CAK45837.1 | 40% |
| EHA28102.1 | 41% |
| XP_001395986.1 | 36% |
| GAA87759.1 | 35% |
| XP_002374905.1 | 38% |
| XP_001819606.1 | 38% |
| EHA25577.1 | 35% |
| ZP_07797950.1 | 37% |
| AEO72739.1 | 37% |
| YP_001345734.1 | 38% |
| YP_788405.1 | 37% |
| ZP_06876238.1 | 37% |
| NP_248945.1 | 37% |
| YP_002437859.1 | 37% |
| EGM13823.1 | 37% |
| ZP_01363161.1 | 37% |
| ZP_04936675.1 | 37% |
| ZP_09387347.1 | 36% |
| XP_001393328.2 | 39% |
| GAA19696.1 | 37% |
| XP_572217.1 | 35% |
| YP_003114400.1 | 37% |
| ZP_06711456.1 | 35% |
| BAG32388.1 | 30% |
| XP_001217436.1 | 37% |
| YP_004902842.1 | 35% |
| ZP_09000373.1 | 35% |
| YP_003111840.1 | 36% |
| ZP_03780130.1 | 35% |
| ZP_09425197.1 | 34% |

TABLE 4-continued

Fdc1 homologue polypeptides

| GenBank Accession No. | Overall % sequence identity with SEQ no. 1 |
|---|---|
| BAG32384.1 | 28% |
| XP_664768.1 | 27% |
| AAO72071.1 | 29% |
| YP_004828050.1 | 32% |
| YP_001535961.1 | 31% |
| ZP_09054416.1 | 28% |
| ABI94382.1 | 32% |
| ZP_05967166.1 | 32% |
| ZP_07293769.1 | 31% |
| YP_001007209.1 | 30% |
| CBY26238.1 | 30% |
| YP_004297415.1 | 30% |
| XP_002397336.1 | 23% |
| YP_001703500.1 | 27% |
| ADJ93893.1 | 28% |
| ADJ93969.1 | 31% |
| CAC12690.1 | 28% |
| ADJ93946.1 | 30% |
| YP_158784.1 | 28% |
| ADJ94002.1 | 25% |
| BAL27017.1 | 27% |
| ADJ93979.1 | 30% |
| CBX30514.1 | 27% |
| CBX73487.1 | 21% |

TABLE 5

Pad1 homologue polypeptides

| GenBank Accession No. | Overall % sequence identity with SEQ no. 2 |
|---|---|
| NP_010827.1 | 100% |
| AAA20484.1 | 99% |
| EDN60853.1 | 99% |
| BAG32352.1 | 98% |
| BAG32360.1 | 98% |
| BAG32371.1 | 98% |
| EHN02916.1 | 80% |
| EGA79325.1 | 85% |
| XP_461564.2 | 56% |
| XP_002499371.1 | 58% |
| XP_002421129.1 | 56% |
| XP_718069.1 | 56% |
| EEQ46647.1 | 56% |
| EFY97970.1 | 50% |
| XP_002374906.1 | 51% |
| XP_001819605.2 | 49% |
| XP_386611.1 | 48% |
| EHK46071.1 | 48% |
| EFZ02050.1 | 48% |
| XP_002380060.1 | 48% |
| XP_001818651.1 | 48% |
| EHK20701.1 | 47% |
| XP_002564375.1 | 47% |
| XP_001261423.1 | 45% |
| GAA90863.1 | 47% |
| XP_001390532.1 | 47% |
| XP_001545681.1 | 44% |
| EGU80879.1 | 45% |
| XP_001218694.1 | 17% |
| XP_001393326.1 | 46% |
| YP_004828051.1 | 42% |
| EHK21881.1 | 47% |
| XP_003195392.1 | 44% |
| EFX01028.1 | 38% |
| ZP_07293770.1 | 42% |
| EGU86507.1 | 41% |
| EFY85844.1 | 42% |
| NP_388245.1 | 44% |
| ZP_05227335.1 | 39% |
| YP_077665.1 | 42% |

TABLE 5-continued

Pad1 homologue polypeptides

| GenBank Accession No. | Overall % sequence identity with SEQ no. 2 |
|---|---|
| YP_004206319.1 | 43% |
| AEP89434.1 | 43% |
| EHA29008.1 | 43% |
| BAI83837.1 | 43% |
| YP_003944634.1 | 41% |
| YP_003868777.1 | 41% |
| AET58676.1 | 41% |
| YP_004517954.1 | 41% |
| YP_001211446.1 | 42% |
| ZP_08624297.1 | 42% |
| YP_004875917.1 | 43% |
| ZP_06875184.1 | 42% |
| CAD19476.1 | 40% |
| YP_174133.1 | 40% |
| ABV91288.1 | 40% |
| AEB22516.1 | 40% |
| ABI94381.1 | 39% |
| YP_003192438.1 | 42% |
| YP_003918919.1 | 41% |
| EHM06418.1 | 40% |
| CCF03850.1 | 41% |
| YP_001703499.1 | 40% |
| YP_003975944.1 | 41% |
| YP_004497687.1 | 40% |
| ZP_09000374.1 | 42% |
| ZP_08499357.1 | 40% |
| YP_001420010.1 | 41% |
| ZP_08113998.1 | 40% |
| XP_003306895.1 | 37% |
| ZP_06355238.1 | 40% |
| AEG59431.1 | 41% |
| EGA75335.1 | 42% |
| ZP_08273725.1 | 39% |
| YP_003211671.1 | 40% |
| YP_002330491.1 | 40% |
| YP_428976.1 | 40% |
| XP_001395985.1 | 40% |
| YP_217838.1 | 40% |
| NP_461842.1 | 40% |
| YP_002227663.1 | 40% |
| YP_003614566.1 | 40% |
| CBK86407.1 | 40% |
| YP_001354955.1 | 41% |
| ZP_09039132.1 | 40% |
| YP_001464062.1 | 39% |
| ZP_05970041.1 | 40% |
| EGA83277.1 | 41% |
| ZP_02667593.1 | 39% |
| YP_002413752.1 | 40% |
| NP_457310.1 | 39% |
| ZP_06541550.2 | 40% |
| EHP66767.1 | 40% |
| YP_002216887.1 | 39% |
| YP_004953406.1 | 40% |
| EFW76961.1 | 40% |
| ZP_02884445.1 | 41% |
| YP_001101250.1 | 40% |
| YP_002638497.1 | 39% |
| YP_145845.1 | 39% |

The invention claimed is:

1. A method for preparing a mono-unsaturated alkene comprising:
contacting an aliphatic alpha, beta-mono-unsaturated carboxylic acid with an Fdc1 polypeptide comprising an amino acid sequence with at least 21% sequence identity to SEQ ID NO: 1 and ferulic acid decarboxylase activity and a Pad1 polypeptide comprising an amino acid sequence with at least 37% sequence identity to SEQ ID NO: 2 and phenacrylate decarboxylase activity.

2. The method of claim 1, wherein the alkene is a terminal alkene.

3. The method of claim 1, wherein the alkene is a straight chain or branched chain alkene.

4. The method of claim 1, wherein the alkene comprises between 4 and 30 carbon atoms.

5. The method of claim 1, wherein the Fdc1 polypeptide has an amino acid sequence with at least 50% sequence identity to SEQ ID NO: 1.

6. The method of claim 5, wherein the Fdc1 polypeptide has an amino acid sequence with at least 55% sequence identity to SEQ ID NO: 1.

7. The method of claim 1, wherein the Pad1 polypeptide has an amino acid sequence with at least 60% sequence identity to SEQ ID NO: 2.

8. The method of claim 7, wherein the Pad1 polypeptide has an amino acid sequence with at least 65% sequence identity to SEQ ID NO: 2.

9. The method of claim 1, wherein at least one of the Fdc1 polypeptide and Pad1 polypeptide is expressed by a recombinant host cell.

10. The method of claim 9 wherein the Fdc1 polypeptide has an amino acid sequence selected from SEQ ID NOS: 1 and 16-26 and sequences shown in Table 4.

11. The method of claim 9 wherein the Pad1 polypeptide has an amino acid sequence selected from SEQ ID NOS: 2 and 27-37 and sequences shown in Table 5.

12. The method of claim 9 wherein the recombinant host cell is a microorganism genetically modified to express at least one exogenous polypeptide selected from sequences SEQ ID NOS: 1, 2 and 16-37 and sequences shown in Tables 4 and 5.

13. The method of claim 12 wherein the host cell comprises at least one nucleic acid sequence encoding one or more of the amino acid sequences SEQ ID NOS: 1, 2 and 16-37 and sequences shown in Tables 4 and 5.

14. The method of claim 13 wherein the nucleic acid sequence is selected from one or more sequences SEQ ID NOS: 3-7 and 38-59.

15. The method of claim 9 wherein the recombinant host cell comprises at least one of a yeast and a bacterium.

16. The method according of claim 15 wherein the yeast is *Saccharomyces cerevisiae* and the bacterium is *Escherichia coli*.

17. The method of claim 1 further comprising:
combining the mono-unsaturated alkene with one or more additional components to generate a biofuel and/or biochemical.

18. The method of claim 1 further comprising:
isolating the mono-unsaturated alkene; and
performing at least one of hydrogenating and hydroisomerizing the isolated mono-unsaturated alkene to produce an alkane.

19. The method according to claim 18 further comprising combining the alkane with one or more additional components to generate a biofuel and/or biochemical.

20. The method of claim 1, wherein the Fdc1 polypeptide has an amino acid sequence with at least 30% sequence identity to SEQ ID NO: 1.

\* \* \* \* \*